United States Patent
Strobel et al.

(10) Patent No.: US 11,285,120 B2
(45) Date of Patent: *Mar. 29, 2022

(54) VOLATILE ORGANIC COMPOUND FORMULATIONS HAVING ANTIMICROBIAL ACTIVITY

(71) Applicant: ECOPLANET ENVIRONMENTAL LLC, Belgrade, MT (US)

(72) Inventors: Gary A. Strobel, Bozeman, MT (US); Bryan Blatt, Manhattan, MT (US)

(73) Assignee: ECOPLANET ENVIRONMENTAL LLC, Belgrade, MT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/179,370

(22) Filed: Nov. 2, 2018

(65) Prior Publication Data

US 2019/0269634 A1   Sep. 5, 2019

Related U.S. Application Data

(63) Continuation of application No. 14/322,757, filed on Jul. 2, 2014, now Pat. No. 10,117,841.

(51) Int. Cl.
| | |
|---|---|
| *A61K 31/19* | (2006.01) |
| *A01N 37/02* | (2006.01) |
| *A01N 37/12* | (2006.01) |
| *A61K 31/22* | (2006.01) |
| *A61K 36/062* | (2006.01) |
| *A61K 47/44* | (2017.01) |

(52) U.S. Cl.
CPC .............. *A61K 31/19* (2013.01); *A01N 37/02* (2013.01); *A01N 37/12* (2013.01); *A61K 31/22* (2013.01); *A61K 36/062* (2013.01); *A61K 47/44* (2013.01); *A23V 2002/00* (2013.01); *Y02A 50/30* (2018.01)

(58) Field of Classification Search
CPC ........ A01N 37/02; A01N 63/04; A01N 25/08; A01N 37/12; A61K 2300/00; A61K 31/19; A61K 31/22; A61K 36/062; A61K 47/44

See application file for complete search history.

(56) References Cited

U.S. PATENT DOCUMENTS

| | | | |
|---|---|---|---|
| 3,898,328 A | 8/1975 | Biegler et al. | |
| 3,914,131 A | 10/1975 | Hutchison | |
| 5,210,083 A | 5/1993 | Pfirrmann | |
| 8,453,604 B2 | 6/2013 | Matsuo et al. | |
| 8,728,462 B2 | 5/2014 | Gandhi et al. | |
| 8,741,625 B2 | 6/2014 | Tada et al. | |
| 2002/0034568 A1 | 3/2002 | Blyth et al. | |
| 2009/0075919 A1 | 3/2009 | Einbond et al. | |
| 2010/0272690 A1 | 10/2010 | Gandhi et al. | |
| 2013/0302480 A1 | 11/2013 | Gandhi et al. | |
| 2014/0323572 A1 | 10/2014 | Pimentel et al. | |

FOREIGN PATENT DOCUMENTS

| | | |
|---|---|---|
| WO | 96/24247 A1 | 8/1996 |
| WO | 9624247 A1 | 8/1996 |
| WO | 2011/153470 A2 | 12/2011 |
| WO | 2011153470 A2 | 12/2011 |
| WO | 2013081777 A1 | 6/2013 |
| WO | 2014/032090 A1 | 3/2014 |
| WO | 2014032090 A1 | 3/2014 |

OTHER PUBLICATIONS

Beppler et al. When more is less: Emergent suppressive interactions in three-drug combinations. BMC Microbiology (2017) 17:107. (Year: 2017).*
Kaur et al. "Nonpathogenic Fusarium as Biological control Agent"; Plant Pathology Journal 9(3):79-91; 2010.
Bicknell, EJ et al. "Neonatal Calf Diarrhea", Animal Care and Health Maintenance, pp. 19-24.
Storer, AJ et al, 1998, "Association of the pitch canker fungus, *Fusarium subglutinans* f.sp. *pini*, with Monterey pine seeds and seedlings in California", Plant Pathology, vol. 46, pp. 649-656.
Gianneechini, R. et al., 2002, "Occurence of Clinical and Sub-clinical Mastitis in Dairy Herdsin the West Littoral Region in Uruguay", Acta Veterinaria Scandinavia, vol. 43, pp. 221-330.
Bicknell, EJ et al., 1983, "Neonatal Calf Diarrhea", Animal Care and Health Maintenance, pp. 19-24.
Storer, AJ et al., 1988, "Association of the pitch canker fungus, *Fusarium subglutinans* f sp *pini*, with Monterey pine seeds and seedlings in California", Plant Pathology, vol. 46, pp. 649-656.
Gianneechini, R. et al., 2020, "Occurrence of Clinical and Sub-Clinical Mastitis in Dairy Herds in the West Littoral Region in Uruguay", Acta Veterinaria Scandinavica, vol. 43, pp. 221-330.
Anschau et al., 2011, Enzymatic Synthesis Optimization of Isoamyl Butyrate', Journal of the Brazilian Chemical Society, vol. 22, No. 11, pp. 2148-2156.
Kaur et al. Nonpathogenic Fusarium as Biological control Agent. Plant Pathology Journal 9(3):79-91. (Year:2010).
"Balance Refuel + Recover", Edited and Issued by Balance Sports Nutrition; Oct. 11, 2014; New Zealand; 2 pages; Description of Product now discontinued.

* cited by examiner

*Primary Examiner* — Robert A Wax
*Assistant Examiner* — Olga V. Tcherkasskaya
(74) *Attorney, Agent, or Firm* — Nath, Goldberg & Meyer; Joshua B. Goldberg; Scott H. Blackman

(57) ABSTRACT

The present invention includes novel chemical formulations having antimicrobial activity and their methods of use thereof. In some embodiments, the formulation further comprises at least one fungus.

20 Claims, 28 Drawing Sheets

Specification includes a Sequence Listing.

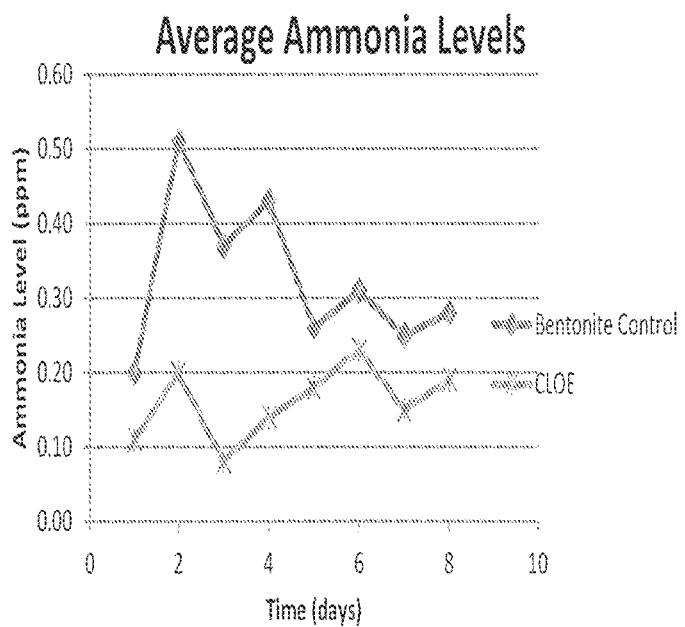
Figure 14A
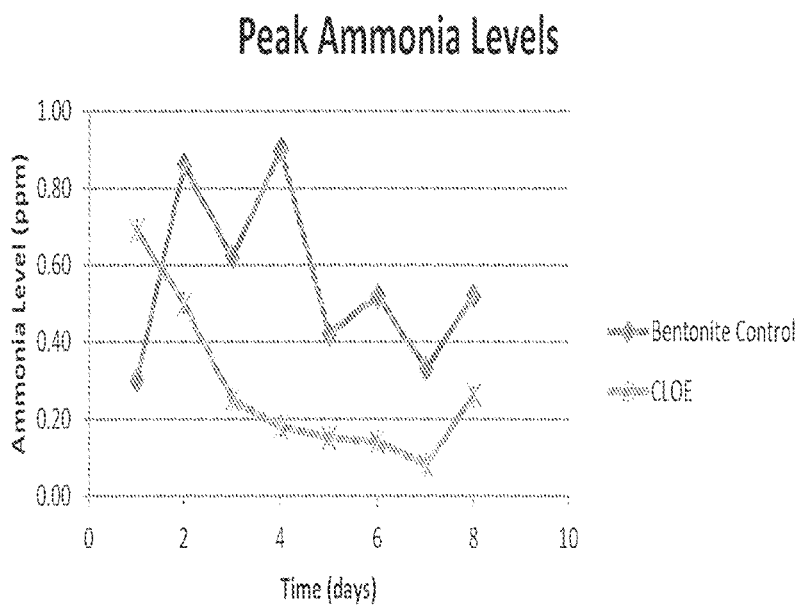
Figure 14B
Figure 14

Figure 15A                     Figure 15B

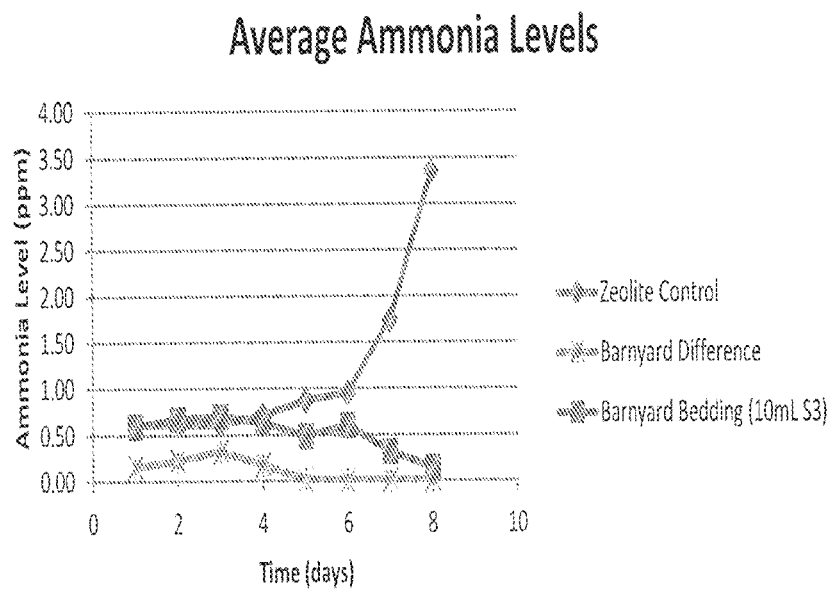
Figure 17A
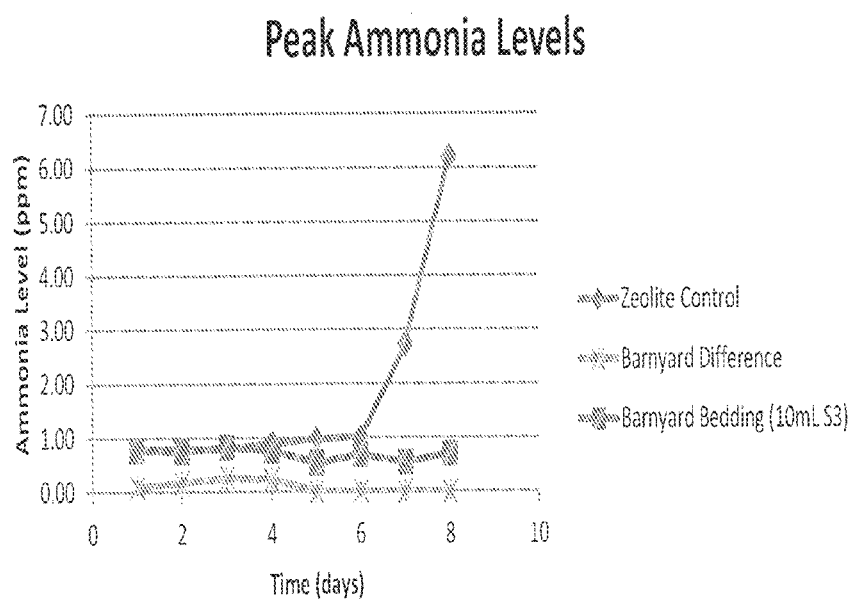
Figure 17B
FIGURE 17

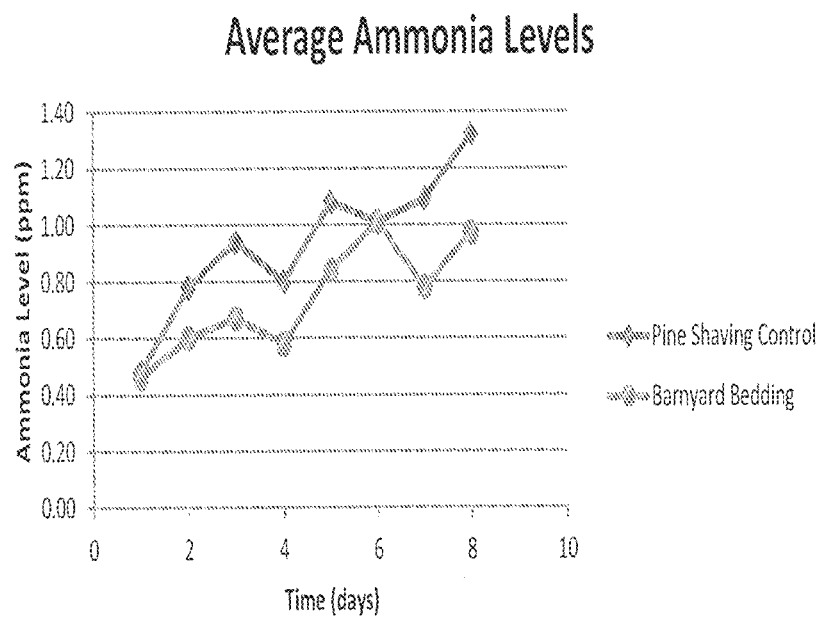
Figure 19A
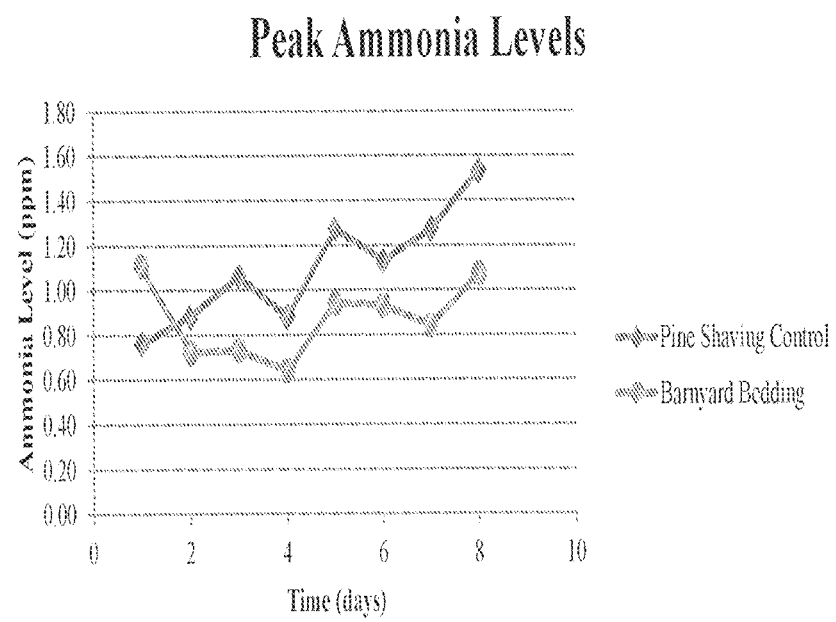
Figure 19B
Figure 19

 
Figure 20A　　　　Figure 20B
Figure 20

 
Figure 21A					Figure 21B
Figure 21

 
Figure 23A　　　　Figure 23B
Figure 23

 
Figure 24A     Figure 24B
Figure 24

 
Figure 25A  Figure 25B
Figure 25

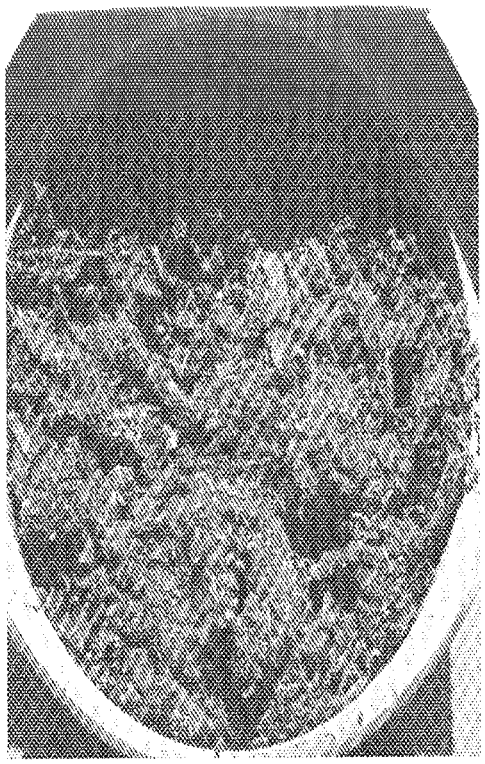 
Figure 27A　　　　　　　　Figure 27B
Figure 27

VOLATILE ORGANIC COMPOUND FORMULATIONS HAVING ANTIMICROBIAL ACTIVITY

CROSS-REFERENCE TO RELATED APPLICATIONS

This is a Continuation Application of U.S. patent application Ser. No. 14/322,757, filed Jul. 2, 2014, an application claiming the benefit from to U.S. Provisional Application No. 61/842,362, filed Jul. 2, 2013, and U.S. Provisional Application No. 61/948,902, filed Mar. 6, 2014, each of which applications are incorporated by reference herein in their entireties.

The Sequence Listing submitted in text format (.txt) filed on May 10, 2019, named "14322,757.txt", (created on Apr. 24, 2019, 6.37 KB), is incorporated herein by reference.

BACKGROUND OF THE INVENTION

The importance of safely disposing billions of pounds of human and animal excrement each day so as to avoid the myriad of health problems associated with such wastes cannot be overstated. In reality, only a fraction of this massive amount of material is safely treated, while the remainder is untreated and poses a threat to human and animal health. For instance, it is well known that the complex of bacterial and other agents causing gastrointestinal diseases is the world's largest single cause of mortality. It is also well known that these types of diseases impact primarily infants and children, as well as livestock. It is estimated that over the next ten years, at least twenty million people will die as a result of poor or inadequate sanitation facilities.

One of the reasons for this is that approximately 2.4 billion people live in areas without adequate sanitation facilities. Nearly 4000 children die each day from conditions such as diarrhea. In addition, people suffering from waterborne diseases occupy about half of the world's hospital beds. In several Asiatic countries, twice as many people are dying from diarrhea-related diseases as from AIDS. Essentially, the poor sanitation conditions are resulting from or related to the inability of homes, communities and in some instances, entire countries, to adequately treat and dispose of human and animal wastes, which bear and promote the growth and development of disease-causing microorganisms.

Without question, the unwanted effects of microorganisms in industrial settings are numerous. For example, safer and more effective means for treating microbe-laden surfaces in medical or hospital environments are needed. Safer and more effective means for treating agricultural crops for unwanted microbial growth are needed. Further, a means for reducing the unwanted odors produced in the breakdown of fecal matter in industrial farming operations is desperately needed.

There is an urgent need for the replacement of antibiotics with other types of compounds that also exhibit antimicrobial activity. Continued use of most of the commonly used antibiotics for animals and agriculture has resulted in acquired resistance in microbial populations, especially microbes that are capable of being pathogenic. Every year, at least 23,000 people in the United States die due to infections caused by drug resistant bacteria, and the number is increasing.

Thus, there is a need in the art for antimicrobial compositions suitable for reducing microorganisms and the effects of microbial outgrowth in a wide range of industrial settings, as well as for formulas and methods of human and animal waste treatment. The present invention satisfies this need.

BRIEF SUMMARY OF THE INVENTION

In one embodiment, the present invention relates to a chemical formulation having antimicrobial activity comprising propanoic acid, isobutyric acid, and at least one ester. In another embodiment, the at least one ester is isoamyl hexanoates. In another embodiment, the formulation further includes at least one carrier selected from the group consisting of bentonite, zeolite and perlite. In another embodiment, the ratio of propanoic acid:isobutryic acid:isoamyl hexanoates is about 3.5:3.5:2 v/v/v. In another embodiment, the ratio of propanoic acid, isobutryic acid and isoamyl hexanoates is about 7 parts of the two acids and 2 parts of isoamyl butyrate. In another embodiment, the formulation further includes at least one endophyte. In another embodiment, the endophyte is of the genus *Fusarium*.

In another embodiment, the present invention relates to a chemical formulation consisting essentially of propanoic acid, isobutyric acid, isoamyl hexanoates and a carrier selected from the group consisting of bentonite, zeolite, and perlite.

In another embodiment, the present invention relates to a chemical formulation comprising propanoic acid and at least one 6-12 carbon (acid) component ester, wherein the chemical formulation has a ratio of propanoic acid:ester component of about 7:2 v/v. In another embodiment, the at least one ester is isoamyl hexanoates. In another embodiment, the formulation further includes at least one nutritional supplement and at least one salt. In another embodiment, formulation comprises glucose, whey protein, potassium chloride, magnesium sulfate, and sodium chloride. In another embodiment, the formulation comprises glucose, glycine, potassium chloride, sodium chloride, and magnesium acetate. In another embodiment, the formulation comprises glucose, glycine, potassium chloride, sodium chloride, magnesium acetate, and monopotassium phosphate. In another embodiment, the formulation further includes at least one carrier. In another embodiment, the formulation consists essentially of propanoic acid and isoamyl hexanoates at a ratio of propanoic acid:isoamyl hexanoates of about 7:2 v/v. In another embodiment, the formulation includes at least one endophyte. In another embodiment, the endophyte is of the genus *Fusarium*.

In another embodiment, the present invention relates to a method of treating an animal having a disease or disorder associated with a microbial infection, comprising administering to the animal an effective amount of a composition comprising at least one organic acid and at least one ester. In another embodiment, the present invention relates to a composition comprising propanoic acid and at least one 6-12 carbon (acid) component ester, wherein the chemical formulation has a ratio of propanoic acid:ester component of about 7:2 v/v.

BRIEF DESCRIPTION OF THE DRAWINGS

The following detailed description of embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 17B depicts the peak ammonia levels taken from 5-minute interval tests every 24 hours.

FIG. 19, comprising FIGS. 19A-19B, depicts ammonia levels taken over 5-minute intervals every 24 hours. FIG. 19A depicts the average ammonia levels taken over 5-minute intervals every 24 hours. FIG. 19B is a graph depicting that the peak ammonia levels displayed a similar trend, with S-1 treated bedding showing the lowest ammonia production levels. FIG. 19B depicts peak ammonia levels taken from 5-minute interval tests every 24 hours.

FIG. 20, comprising FIGS. 20A-20B, depicts images of a scoured calf prior to and after treatment. FIG. 20A depicts the scoured calf prior to any treatment with S-X solution. FIG. 20B depicts the calf of FIG. 20A after two rounds of treatment with S-X solution.

FIG. 21, comprising FIGS. 21A-21B, depicts images of a scoured calf prior to and after treatment. FIG. 21A depicts the scoured calf prior to any treatment with S-X solution. FIG. 21B depicts the calf of FIG. 21A 24 hours after treatment with S-X solution

FIG. 23, comprising FIGS. 23A-23B, depicts images of a scoured calf prior to and after treatment. FIG. 23A depicts the typical creamy yellow scours exhibited on calf 919. FIG. 23B depicts calf 919 fully recovered after treatment with S-X solution FIG. 24, comprising FIGS. 24A-24B, depicts images of calf 166 of Ranch 9 prior to and after treatment. FIG. 24A depicts calf 166 suffering with scours in the winter of 2014. FIG. 24B depicts the calf one day after treatment with S-X solution, wherein the animal recovered and yellow diarrhea subsided.

FIG. 25, comprising FIGS. 25A-25B, depicts images of a sheep suffering from mastitis and administration of treatment. FIG. 25A depicts the sheep suffering from mastitis. FIG. 25B depicts administration of the S-3 formula to the animal via syringe.

FIG. 26A depicts raspberries treated with control bentonite in the center well. FIG. 26B depicts raspberries treated with the S-3 1:10 mixture. Both sets of raspberries were stored for 1 week at room temperature. The berries treated with S-3 were edible and had no decay.

FIG. 27, comprising FIGS. 27A-27B, depicts soil treated with *P. ultimatum* or S-3. FIG. 27A is a photograph of soil treated with *P. ultimatum* alone with seeds of red beet. Only one or two seeds were observed to germinate. FIG. 27B is a photograph of soil treated with S-3 on bentonite in the presence of *P. ultimatum* and red beet seeds. Many of the seeds were observed to germinate.

FIG. 28A is an image of an agar plate with red beet seed, bentonite, S-3 (1 part to 10 g bentonite), and *P. ultimum*. S-3 was found to control the growth of *P. ultimum*. FIG. 28B is an image of an agar plate with red beet seed and *P. ultimum*. FIG. 28C is an image of an agar plate with red beet seed alone. FIG. 28D is an image of an agar plate demonstrating that S-3 was not harmful to the red beet seed.

DETAILED DESCRIPTION

Figure 1:
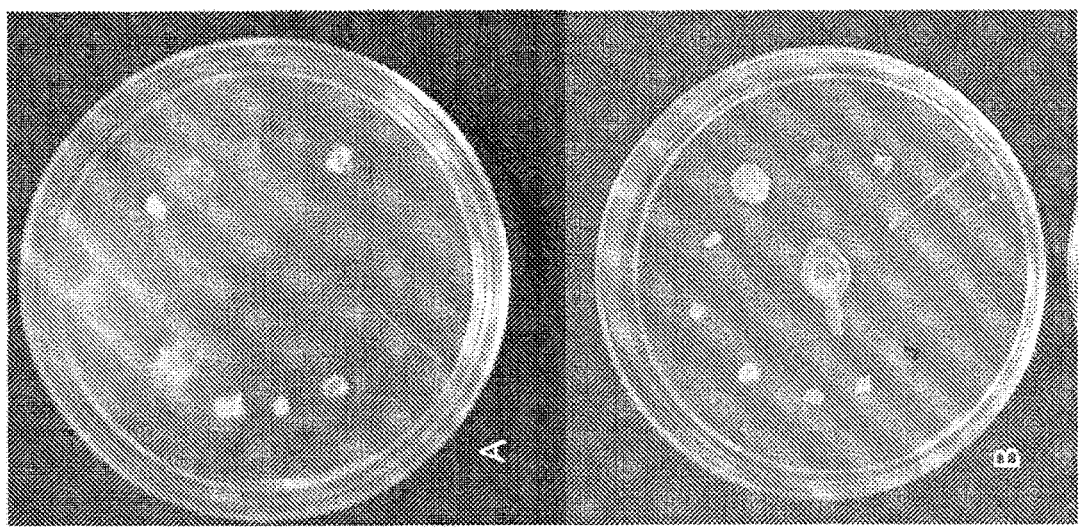
FIG. 1 illustrates a plate bioassay to determine the bioactivity of various esters when combined with a 1:1 mix of the two organic acids as per Table 2. The test organisms were as follows—*Cercospora* (dark-lower left bottom) then clockwise—*Phytophthora*, *Verticillium*, *Sclerotinia*, *Pythium*. *Fusarium*, *Trichoderma*, *Rhizoctonia*, and *Aspergillus*. The streaks were *Saccharomyces* (far right bottom) then *Candida*, *E coli* and *Bacillus* (left bottom). A=control plate, and B=plate with System 1 after incubation for 30 hr.
Figure 2:
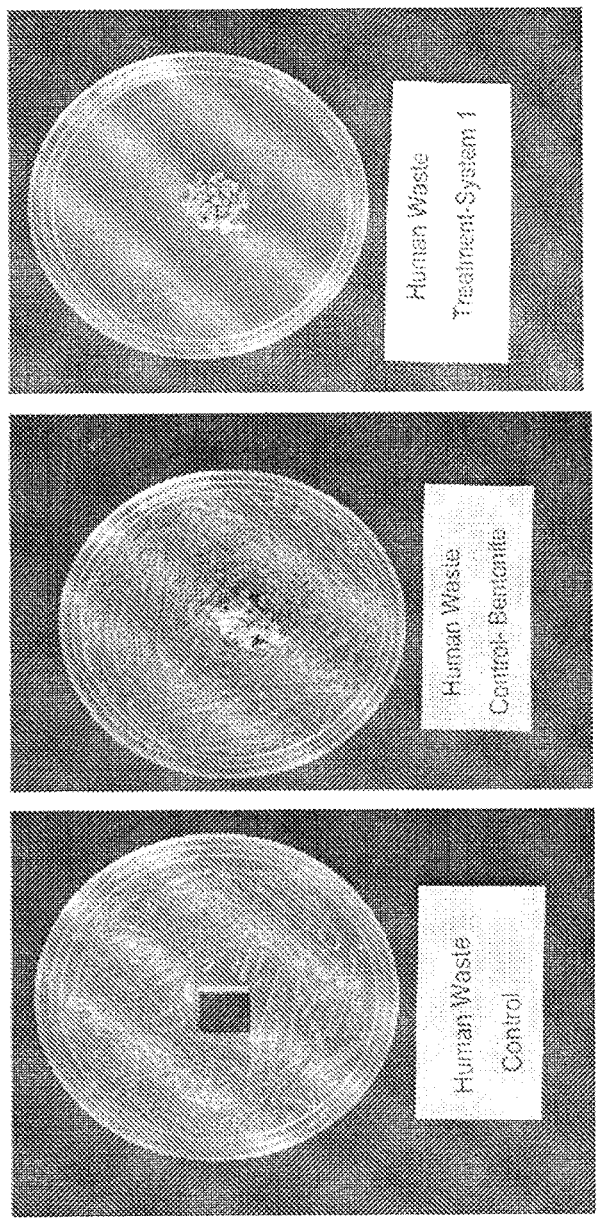
FIG. 2 illustrates the effects of System 1 on the growth of bacteria from human wastes. About 5 mg of fresh human waste was spread over the surface of a Petri plate with potato dextrose agar. Then plugs were removed from the center and bentonite was placed in the well ca. 0.5 g. The bentonite in the center well did not have the ingredients in System 1 on it (center) but the well on the far right had System 1 at the rate of 1 ml System 1 per 10 g of bentonite. The plates were incubated for 48 hr at 22° C. and then photographed. There was no detectable bacterial growth in the System 1 treated plate, but the control plates had ample bacterial colonies.
Figure 3:
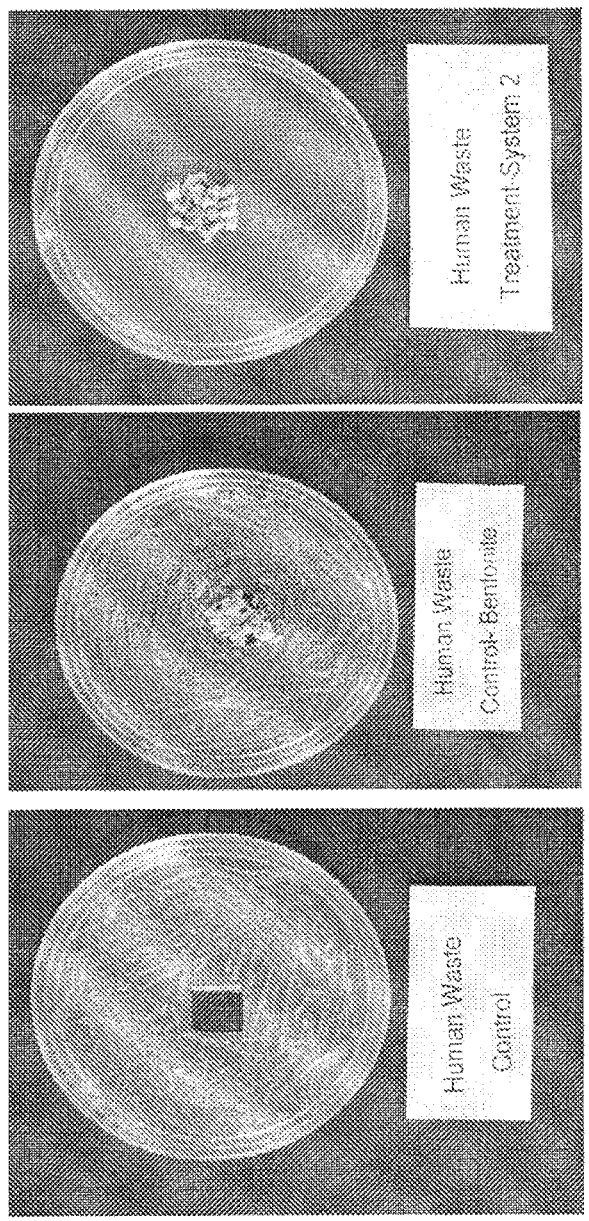
FIG. 3 illustrates the effects of System 2 on the growth of bacteria from human wastes. About 5 mg of fresh human waste was spread over the surface of a Petri plate with potato dextrose agar. Plugs were removed from the center and bentonite was placed in the well ca, 0.5 g. The bentonite in the center well did not have the ingredients in System 1 on it (center) but the well on the far right had system 1 at the rate of 1 ml System 1 per 10 g of bentonite. The plates were incubated for 48 hr at 22° C. and then photographed. There was no detectable bacterial growth in the System 2 treated plate.
Figure 4:
FIG. 4 illustrates two cat litter boxes with cat fecal matter each from 5 different cats ca. 140 g. The box on the right had been treated with System 1 on bentonite with (0.5 ml/100 g bentonite). After 5 days the ammonia readings were 14 ppm on the control (left) and 0 ppm on the treated right. The overall odor was significantly reduced in the treated box.
Figure 5:
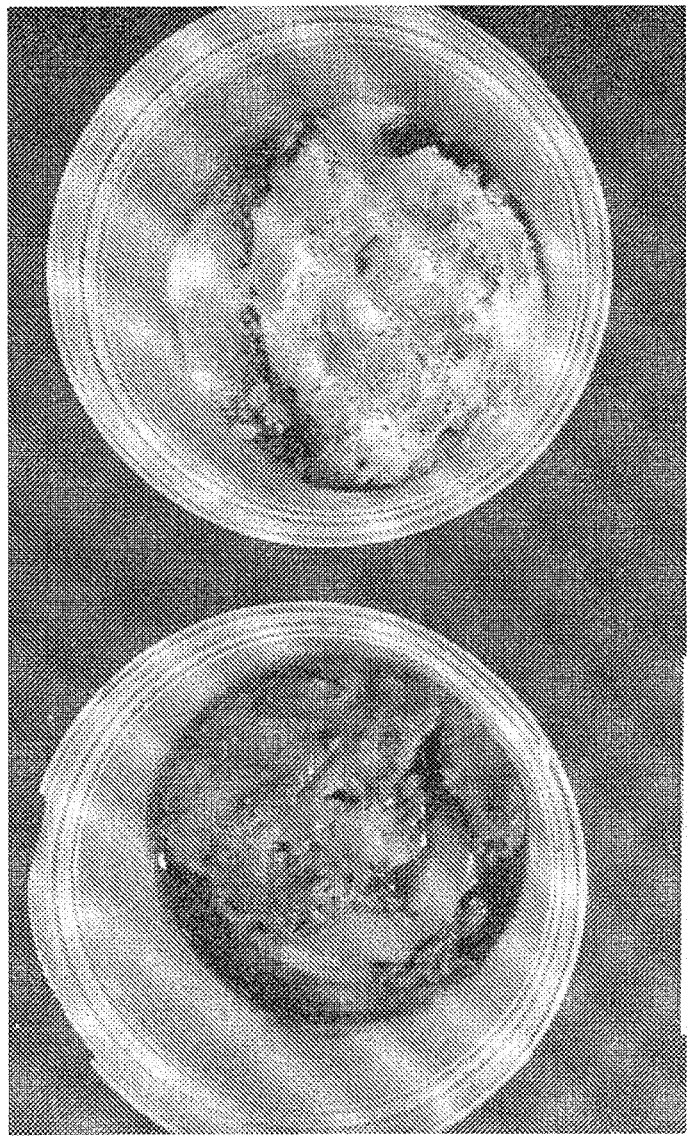
FIG. 5 illustrates treatment of ca. 140 g of human waste in the presence of urine with *Fusarium subglutinans* 06-1 in the presence of System 2 (1 ml on 10 g of zeolite). After 3 weeks there was substantial growth of the *F. subglutinans* (white mycelium in the right container). The ammonia level was 71.4 in the control on the left and 12.1 in the treated container on the right. No fungal growth and no degradation of the wastes occ ammonia production levels.

It is to be understood that the figures and descriptions of the present invention have been simplified to illustrate elements that are relevant for a clear understanding of the present invention, while eliminating, for the purpose of clarity, many other elements found in typical antimicrobial formulations. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

"S-1" as used herein refers to any and all formulations of System 1.

"S-2" as used herein refers to any and all formulations of System 2.

"S-3" as used herein refers to any and all formulations of System 3.

"S-4" as used herein refers to any and all formulations of System 4.

"S-5" as used herein refers to any and all formulations of System 5.

"S-X" as used herein refers to any and all formulations of System X, which may include one or more of Systems 1-5 therein.

As used herein, the term "CLOE" refers to a formulation comprising S-1 or S-5.

As used herein, the term "Barnyard Bedding" refers to a formulation comprising S-1 or S-5.

As used herein, the term "pharmaceutical composition" refers to a mixture of at least one composition of the invention with other chemical components, such as carriers, stabilizers, diluents, dispersing agents, suspending agents, thickening agents, and/or excipients. The pharmaceutical composition facilitates administration of the composition to an organism. Multiple techniques of administering a composition exist in the art including, but not limited to, intravenous, oral, aerosol, parenteral, ophthalmic, pulmonary and topical administration.

As used herein, the term "pharmaceutically acceptable" refers to a material, such as a carrier or diluent, which does not abrogate the biological activity or properties of the composition, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a composition useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the composition useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyllaurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the composition useful within the invention, and are physiologically acceptable to the patient. Supplementary active compositions may also be incorporated into the compositions. The "pharmaceutically acceptable carrier" may further include a pharmaceutically acceptable salt of the composition useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.).

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

The present invention relates to the discovery of effective and useful chemical formulae that, either alone or in combination with certain endophytic fungi, such as *Fusarium* spp, have strong antimicrobial activity and may be particularly suitable for a variety of uses, such as to reduce microbial growth from medical facility surfaces or instruments, reduce microbial growth on agricultural plant surfaces, or to decontaminate, degrade and deodorize human and animal wastes. For example, the formulae of the present invention are suitable for the treatment of wastes in any location, such as in latrines, cat litter boxes, animal stalls, barns, chicken raising facilities, pig barns, pet stations in homes, zoos and a host of other locations.

In a preferred embodiment, the appropriate combination of the harmless formulae containing ingredients that are on the FDA-GRAS list and an appropriate fungi, such as an endophytic fungi *Fusarium* spp, such as *F. subglutinans*, are placed together into a container, such as a biodegradable plastic bag. Also contained in the bag is an appropriate amount of a urine-absorbing polymer that is compatible with the endophytic *Fusarium subglutinans*. This combination of agents represents a safe, rapid and novel treatment process for the recycling of ingredients found in human and animal wastes. The presence of these two ingredients in the bag effectively kills many of the harmful bacteria in the human wastes and at the same time begins the process of recycling the organic consteatuents of the wastes back to a harmless soil additive.

The present invention can be employed in connection with such activities as national emergencies, military maneuvers, marine-related activities, natural disasters, outdoor sporting activities (camping, hiking, canoeing, hunting, biking, etc.) and other activities in which human wastes need to be properly and safely disposed. It also relates to the development of much safer facilities for all livestock and even household pets. As an example, it has been recently noted that proper and safe disposal of human waste is an important concern for the appropriate management of wildland areas of the world. Aesthetics, as well as health concerns, are the major issues facing managers of these areas. Accordingly, the present invention may be suitable for human and animal surfaces, plant surfaces, industrial surfaces, machine tools and a host of other uses.

In one embodiment of the present invention, the formulations of System 1 (S-1), System 2 (S-2), System 3 (S-3), System 4 (S-4) and/or System 5 (S-5), and optionally using bentonite, zeolite or perlite as a carrier (depending on application), are combined together in the container and the processes of bacterial killing and/or waste degradation begin immediately. In another embodiment, the present invention may be used in animal bedding and stall treatments, wherein the chemical mixture (with the carrier) can be applied directly to the areas housing the animals, resulting in the almost immediate killing of bacteria that cause harmful odors such as ammonia. In another embodiment, the present invention may be applied to a surface, such as an agricultural plant surface, a medical facility surface, a medical or industrial tool, or the like, to eliminate or otherwise reduce the microbial count on the treated surface.

Antibiotics are compounds that either kill or inhibit the growth of bacteria. A frequent misconception is that antibiotics are effective against other microorganisms, such as fungi and viruses, when in fact antifungal and antiviral compounds are needed for such purposes. Antibiotics work by interfering with key steps in the metabolism and growth of bacteria and can be broadly grouped into two main categories, bacteriocides and bacteriostatics, depending on whether they kill bacteria or simply inhibit their growth, respectively. Antibiotics are generally safe for use in humans because the steps they target are either unique to certain types of bacteria or are effective against bacteria at very low concentrations considered safe for humans. Other classes of chemicals, such as certain alcohols, acids, and peroxides may have broad inhibitory and/or killing power because they affect fundamental elements of biochemistry common to many forms of life. These kinds of compounds are classified as antiseptics, sterilants, disinfectants, and sanitizers, and preservatives depending on their specific effects on microbial life, modes of effective application, and toxicity to humans. The systems of the present invention, such as S1, are mixtures consisting primarily of short chain organic acids and esters, mostly notably propanoic acid and isoamyl hexanoates. Neither of these molecules is classified as an antibiotic, but both possess antimicrobial properties and can be either bactericidal or bacteriostatic depending on the concentration and length of application.

The systems of the present invention do not work by the same mechanisms as antibiotics. Whereas antibiotics target very specific steps, often by recognizing very specific structural motifs, the systems of the present invention kill bacteria and inhibit their growth by effecting fundamental biochemical properties required to sustain life. Moreover, the components of the systems of the present invention act synergistically such that the effect of the overall mixture is greater than sum of its parts. The mechanism of the synergistic effect seen with these systems is not understood, but other acid/ester mixtures display the same sort of exaggerated combined effect.

One major component of the systems of the present invention, propanoic acid, is a short chain organic acid with an established use as a preservative in the food and agricultural industries. Most organisms, including humans and many bacterial species, have metabolic pathways that facilitate the use of propanoic acid as nutrient and in fact, one group of bacteria can even produce the molecule. Thus, at low concentrations propanoic acid is essentially harmless to almost all organisms, but at higher concentrations it cannot be degraded fast enough and begins to accumulate within the cell. As its concentration within the cell increases, so too does the acidity of the cell. When the acidity inside the cell is too high, enzymes cannot function properly, DNA and other biological molecules are destroyed, and the cell dies. Recent studies indicate that although effects on intracellular acidity are a major antimicrobial mechanism of weak organic acids, it is by no means the only mechanism. As acids dissociate and release protons inside the cell, they become negatively charged. High concentrations of negatively charged molecules inside the cell present a host of detrimental effects on osmolarity, nutrient storage, and metabolism.

At lower concentrations acids may be inhibitory, but not lethal. Increases in acidity occur when an acid dissociates and releases a proton. When the acidity inside a cell becomes too great, the cell can export protons to the outside in an attempt to maintain proper pH levels. Although effective, this strategy requires the consumption of a large amount of energy and can occur without lethality only at low acid concentrations. Because smaller organisms are more sensitive to smaller amounts of propanoic acid, a concentration that is harmless to humans may be fatal or inhibitory to bacteria. Propanoic acid is not the only organic acid in S1, but the antimicrobial effects of other similarly sized organic acids can be presumed to arise from essentially the same mechanism.

The antimicrobial mechanism of esters remains largely unknown. Although not wishing to be bound by any particular theory, one possible clue comes from the observation that for a given set of esters, those that are able to incorporate more effectively into the bacterial cell membrane tend to have increased antimicrobial properties. Incorporation of any molecule into the cell membrane changes the chemical and physical properties of the membrane, which leads to changes in nutrient uptake, waste export, energy generation, and other essential cellular processes. Although not wishing to be bound by any particular theory, this observation has led to the suggestion that incorporation of certain esters into the cell membrane changes its chemical and physical properties in a way that is detrimental to the organism. Alteration of the cell membrane is also a mechanism by which longer chain organic acids are thought to work.

As antibiotics began to be applied on a massive scale during the 20th century, the problem of antibiotic resistance emerged as a major clinical issue. In the 21st century, as the consequences of antibiotic resistance became more visible and widespread, the term entered the public consciousness and was finally recognized for the immense problem that it is. In a bacterial population exposed to antibiotics, resistance is either existent in a very small number of individuals or initially emerges because of natural mutations and is subsequently selected for because individuals resistant to the antibiotic have a survival advantage over non-resistant individuals. Antibiotic resistance spreads by both vertical transmission from a resistant cell to its progeny and by horizontal transmission (direct transfer of resistance genes from a resistant cell to a non-resistant cell). In this way, resistance spreads rapidly and increased antibiotic usage consteatutes a selective pressure that increases the survival advantage of antibiotic resistance.

Bacteria can acquire resistance to a given antibiotic via four primary mechanisms: evolving enzymes that inactive the antibiotic, altering the structure of the target so the antibiotic can no longer bind, rerouting metabolic pathways to skip antibiotic inhibited steps, and developing efflux pumps that pump the antibiotic outside the cell. Each mechanism has a genetic basis and can thus be transferred from the cell that initially developed resistance to non-resistant cells. In some cases, a bacterial cell can acquire resistance to several different kinds of antibiotics. This is how so called "super-bugs" arise and as the usage of antibiotics increases in the agricultural, veterinary, and medical industries, so too will the prevalence of multi-drug resistant bacterial strains. In addition, combinations of small organic molecules, such as acids and esters, that act in a synergistic manner to yield virtually the same antimicrobial effect as antibiotics have been identified. Organic molecules that possess these properties may be referred to as "synergistans."

The mechanisms of antibiotics, as well as resistance to them, can be summed up by one word-specificity. Antibiotics work by targeting specific structural features, enzymes, and macromolecules. Likewise, antibiotic resistance occurs when bacteria develop an efflux pump specific for a given antibiotic or alter a particular structural feature, enzyme, or macromolecule. If antibiotics are specific, the components of the systems of the present invention are general. Organic acids and esters lack specific targets, instead they exert their antimicrobial effects by changing the biochemical environment of bacterial cells. They are effective against a much wider range of organisms and they interfere with multiple cellular processes.

Organic acids are abundant in nature. Any given bacterial cell will invariably be exposed to organic acids at some point in its lifetime and as a result, many bacterial species possess innate genetic mechanisms that, upon induction, help them cope with the stresses brought about by natural organic acid exposure. Perhaps the best studied of these is the *Salmonella* acid tolerance response. Essentially when a *salmonella* cell is exposed to a high, but sub-lethal acid concentration, it induces the expression of a number of genes such that the next time it is exposed to acidic conditions, its chances for survival are much greater. This has been demonstrated experimentally by inoculating an acidic medium with previously exposed and unexposed *salmonella* cells. In almost every case, the previously exposed cells are afforded a much higher tolerance to the acid. *Escherichia coli* also has a thoroughly studied acid tolerance response and it seems likely that the mechanism is present in many other bacterial species. In the case of pathogenic species like *Escherichia coli* and *salmonella*, there is great concern that induction of the acid tolerance response by exposure to sub-lethal concentrations of organic acid food preservatives could increase bacterial virulence because the bacteria are more likely to survive exposure to acidic gastric fluids during digestion.

Nevertheless, there is an important difference between resistance to antibiotics and resistance to organic acids. Many of the genes for antibiotic resistance lie on mobile genetic elements known as plasmids that are easily transferred between bacterial cells and bacterial species. In this way, it is a relatively simple process for any given bacterial cell to acquire resistance to numerous antibiotics. Acid resistance mechanisms such as the acid tolerance response, on the other hand, are encoded on chromosomal DNA. This kind of genetic information can only be transferred to progeny cells and thus the sudden rise of "super-bugs," as has been observed with multi-drug resistance bacterial strains, does not apply. Moreover, although not wishing to be bound by any particular theory, it is possible that the synergistic effects observed when an organic acid is used in conjunction with organic esters could negate some acid resistance mechanisms.

In one embodiment, to identify a microbe that could grow on human and animal wastes resulting in their degradation, it was essential to formulate a novel antibiotic mixture that would kill the microbial contents of the wastes that normally act to break down urea to ammonia and uric acid. The ammonia is lethal to most fungi that otherwise would degrade the solid constituents of the wastes. Central to this discovery is the known fact that propanoic acid has antibacterial activities but only at the inhibitory level, and the same is true for isobutryic acid. Thus, these two compounds were the starting ingredients for the new and effective antibiotic mixture. What was needed was an additional ingredient to lend microbial lethality to the mix. Then, in a completely unexpected manner it was learned that the addition of certain esters to these small organic acids would lend to them significantly enhanced antimicrobial activities.

Microorganisms living in the world's rainforests, in order to survive, must have evolved biochemical mechanisms to cope with potential competitors. In this regard, they developed an ability to produce molecules that are antimicrobial and compounds that inhibit and destroy other microbes. Because new antibiotics are sought after by mankind, researchers visit rainforests in search of new microbes and the agents that they produce to inhibit and destroy other microbial competitors. Certain rainforest microbes have provided important chemical clues as to which compounds have been chosen for Systems 1-4.

Formulations

In part, the present invention includes a chemical formulation comprising at least one organic acid, such as propanoic acid, isobutyric acid, or butyric acid. In one embodiment, the chemical formulation has antibacterial activity when applied to human or animal waste. In certain embodiments of, the organic acid that is used may contain from 2-5 carbon atoms and each acid used can vary from 0% to 80% of the bioactive mixture. In a preferred embodiment, the organic acid is propanoic acid. In another embodiment, the present invention includes a chemical formulation consisting essentially of an organic acid, such as propanoic acid, isobutyric acid, or butyric acid. In one embodiment, the chemical formulation consists essentially of propanoic acid. In certain embodiments, the chemical formulation comprises two organic acids. In one embodiment, the two organic acids are propanoic acid and isobutyric acid. In one embodiment, the chemical formulation comprises a combination of two organic acids and at least one ester. In one embodiment, the chemical formulation comprises propanoic acid, isobutryic acid, and at least one ester. In another embodiment, the two organic acids are propanoic acid and isobutyric acid and the at least one ester is isoamyl butyrate. In another embodiment, the two organic acids are propanoic acid and isobutyric acid and the at least one ester is isoamyl hexanoates. In another embodiment, the two organic acids are propanoic acid and isobutyric acid and the at least one ester is isoamyl acetate.

As contemplated herein, the chemical formulation may further comprise at least one ester. As contemplated herein, the at least one ester may be any ester listed in Table 1 or elsewhere herein. In certain embodiments, the ester can have from 3 to 10 carbon atoms and any ester or combination thereof may represent at least 20% of the mixture. In one embodiment, the ester is an isoamyl ester. As contemplated herein, embodiments of the present invention may be alternatively formulated using an entire family of isoamyl esters of various acid components ranging from C-6 (hexanoate) to C-12 (laurate) as well as various aromatic (acid) esters of isoamyl alcohol such as cinnamate, benzoate and, phenylacetate. In one embodiment, the ester is isoamyl hexanoates. As used herein, the term "hexanoates" may mean a single type of hexanoate or may include a mixture of the acid form of hexanoates, including branched forms. In another embodiment, the ester is isoamyl formate. In another embodiment, the ester is isoamyl butyrate. In another embodiment, the ester is isoamyl acetate. In one embodiment, the ester is isoamyl acetate. In one embodiment, the ester is selected from the group consisting of allyl acetate, n-decyl acetate, isoamyl acetate, and phenethyl acetate. In one embodiment, the ester is strawberry aldehyde (ethyl 3-methyl-3-phenyl-oxirane-2-carboxylate, an organic ester). In certain embodiments, the at least one ester may be any single carbon (acid) component ester. In one embodiment, the at least one ester is isoamyl formate. In certain embodiments, other compounds can be added as the ester component of the formulations. For example, the octanoate ester of isoamyl alcohol is active and so too is the laurate ester. Accordingly, the formulations of the present invention may include use of the entire spectrum from 6-12 carbon (acid) components of the isoamyl esters. In one embodiment, the ester is the octanoate ester of isoamyl alcohol. In another embodiment, the ester is the laurate ester of isoamyl alcohol. In certain embodiments, benzene components may be used as well as the benzoate ester, the cinnamate, and the salicylate esters. In one embodiment, the chemical formulation comprises propanoic acid and at least one 6-12 carbon (acid) component ester.

In certain embodiments, the formulae of the present invention may include mixtures of at least one organic acid and at least one ester at any ratio. In one embodiment, the ratio of the at least one organic acid to the at least one ester is about 6-7 to about 2-3. In preferred embodiments, the ratio of the at least one organic acid and the at least one ester is about 7:2. In other embodiments, the formulae of the present invention may include mixtures of two organic acids and at least one ester at any ratio. In one embodiment, the ratio of a first organic acid:a second organic acid:at least one ester is about 3.5:3.5:2 v/v/v. In another embodiment, the mixture of a first organic acid:a second organic acid:at least one ester is about 7 parts of the two acids and 2 parts of the selected ester. In one embodiment, the chemical formulation comprises propanoic acid and at least one 6-12 carbon (acid) component ester, wherein the chemical formulation has a ratio of propanoic acid:ester component of about 7:2 v/v.

As contemplated herein, the present invention may include any chemical formulation plus the addition of at least one endophytic fungus. The present invention is not limited to any particular fungus, however and endophytic fungus is preferred, and a fungus from the genus *Fusarium* is more preferred. Most preferred is the endophytic fungus of the species *Fusarium subglutinans*. In another embodiment, the endophytic fungus is a fungus from the genus *Gloeosporium*. As contemplated herein, the fungus may be incorporated into any formulation via inoculated barley, or other suitable carrier for a fungus as is understood by those skilled in the art. In one embodiment, the chemical formulation comprises two organic acids and at least one ester and at least one fungus, wherein the two organic acids and the at least one ester kills or reduces bacteria growth on the human or animal waste, and the at least one fungus increases the rate of decomposition of the human or animal waste. In another embodiment, the formulation comprises propanoic acid, isobutryic acid, at least one ester and at least one fungus. In certain embodiments, the formulation may additionally comprise cineole, valencene, salts or any other additive, excipient or other component desired to produce a formulation having the desired characteristic.

In some embodiments, supplementing a fungal culture with additional compounds may enhance its fungal inhibitory properties to an extent greater than either the agents produced by the fungus or the compound alone. Such activity is deemed synergism. Thus, the present invention also provides chemical formulations comprising at least one fungus and at least one synergistan. As used herein, the term "synergistan" refers to any chemical compound that, when administered in combination with another compound, displays greater microbial inhibitory activity than the activity observed when each compound is administered alone. In a non-limiting example, when a synergistan is combined with a fungal culture, the combined gas phase of the fungus and the synergistans displays increased antimicrobial activity than either the gas phase of the fungus or the synergistan alone.

In certain embodiments, the chemical formulations of the present invention may be used in combination with carriers such as zeolite or bentonite as a cat litter treatment, horse barn, cattle barn, sheep barn, or small animal bedding treatment. In such embodiments, the present invention inhibits microbes that inhabit fecal matter, such as *Escherichia coli*, and break down urea in urine to release ammonia. In another embodiment, the chemical formulations of the present invention may be added to a carrier such as, without limitation, bentonite, zeolite, perlite or other silica based carriers, in amounts that are effective in killing bacteria and reducing harmful and noxious odors.

In certain embodiments, the present invention may be mixed with a foam or other dispersing solution and used as an antimicrobial spray or for surfaces that are contaminated with bacteria or other microbes, such as for the treatment of surfaces in hospitals, home food prep areas, contaminated areas for food processing, including all industrial food processors, fruits, meats, and others in which bacterial contamination is commonly a problem.

In certain embodiments, a composition of the present invention comprises at least one chemical formulation or formula of the present invention. In one embodiment, the compositions of the invention are formulated using one or more pharmaceutically acceptable excipients or carriers. In one embodiment, the pharmaceutical compositions of the invention comprise a therapeutically effective amount of a formula of the invention and a pharmaceutically acceptable carrier. Examples of pharmaceutically acceptable carriers include non-ionic solubilizers and emulsifiers that include a mixture of polyethylene glycol conjugates and are sold under the CREMOPHOR® brand, or any other biological surfactant as would be understood by one skilled in the art. In one embodiment, the pharmaceutically acceptable carrier is a non-ionic solubilizer or emulsifier sold under the trademark CREMOPHOR®.

In certain embodiments, the formulae of the present invention, and preferably S-3, may be used with a carrier (zeolite or bentonite or talc) to treat soil areas that are about to receive either seed or young transplants to reduce or eliminate damping of infections.

In certain embodiments, the formulae of the present invention may be mixed with detergents to be used as a carpet scrubbing and bacterial decontamination agent for animal waste, human waste or other biofouling of carpet surfaces.

In certain embodiments, the formulae of the present invention may be administered as a spray to decontaminate fruits, vegetables, grains and other agricultural products during planting, during growth, during harvest and/or during transport.

In certain embodiments, the formulae of the present invention may be applied to or formulated, embedded or otherwise integrated within baby diapers, bandages or other devices in which bacterial decontamination is desired.

In certain embodiments, the formulae of the present invention may be additionally formulated with a detergent to function as a soap for the decontamination of human and animal skin.

In certain embodiments, the formulae of the present invention may be additionally formulated, embedded or otherwise integrated within a candle wax for area decontamination via vapors when lit.

In particular the chemical formulations of the present invention show remarkable antibiotic activity against bacteria associated with human and animal wastes. These mixture can be specifically delivered to their respective target site via inert carriers such as, without limitation, bentonite, zeolite, perlite or other silica based carriers. In this case, the specific location for use of the carrier and the antibiotic combination may include, for example and without limitation, the bedding locations of all domestic and zoo related animals and animals used as household pets. The mixture can be applied to the stalls, bedding and places where animals live in order to reduce the load of bacteria and harmful gases.

It should be appreciated that the formulations of the present invention may include any additional salts, excipients, nutritional additive or supplement, and the like, such that the final formulation is suitable for topical application, ingestion, inhalation or any other form of administration desired.

System 1

As described elsewhere herein, the chemical formulation may comprise two organic acids and at least one ester. For example, in one embodiment, the formulation includes propanoic acid:isobutryic acid:isoamyl butyrate. In one embodiment, the ratio of propanoic acid:isobutryic acid:isoamyl butyrate is about 3.5:3.5:2 v/v/v. In another embodiment, the mixture of propanoic acid:isobutryic acid:isoamyl butyrate is about 7 parts of the two acids and 2 parts of the selected ester. It should be appreciated that the chemical formulation of System 1 is not limited to any particular ratio of such chemical components. In another embodiment, the chemical formulation of System 1 consists of only two organic acids and a single ester. In such an embodiment, the formulation consists of propanoic acid:isobutryic acid:isoamyl butyrate at the ratios described above. In certain embodiments, the formulation may additionally comprise cineole, valencene, salts or any other additive, excipient or other component desired to produce a formulation having the desired characteristic.

In another embodiment, the chemical formulation of System 1 may be added to a carrier such as, without limitation, bentonite, zeolite, perlite or other silica based carriers, in amounts that are effective in killing bacteria and reducing harmful and noxious odors. This rate is usually 1 ml of System 1 to 224 g of the carrier V/W or in other appropriate ratios that are effective, without limitation.

System 2

As contemplated herein, the present invention may include any chemical formulation of System 1 plus the addition of at least one endophytic fungus. As demonstrated herein, endophytic fungi of the group *F. subglutinans* and others are particularly suited to grow on and degrade human wastes. In addition, the fungus is only able to grow on the liquid and solid waste combination when another antimicrobial mixture such as System 1 is applied and this mixture maximally allows for fungal growth whilst killing bacteria and other microbes. In one embodiment, the fungus is *Fusarium subglutinans*. In one embodiment, the fungus is incorporated into System 2 via inoculated barley. In certain embodiments, the formulation may additionally comprise cineole, valencene, salts or any other additive, excipient or other component desired to produce a formulation having the desired characteristic.

In one embodiment, System 2 includes the chemical formulation of System 1, such as propanoic acid:isobutryic acid:isoamyl butyrate in the ratio of 3.5:3.5:2 v/v/v, or 7 parts of the two acids and 2 parts of the ester, which is then added at the rate of 1/10 V/W of the mixture to the dry weight of the carrier substance such as bentonite, perlite or zeolite etc. It should be appreciated that the chemical formulation of System 2 is not limited to any particular ratio of such chemical components. Barley inoculated with *Fusarium subglutinans* is also added. This mixture is then added as 10 g to each container, such as a plastic bag, used to treat and dispose of human wastes. It allows for the rapid growth of *Fusarium subglutinans* in contrast to System 1 alone, which does not. Other items may also be added to the bag including liquid absorbing polymers in appropriate amounts, as would be understood by those skilled in the art.

System 3

As contemplated herein, the chemical formulation of the present invention may comprise at least one organic acid and at least one ester. In a preferred embodiment, the at least one organic acid is propanoic acid. In one embodiment, the at least one ester is isoamyl hexanoate or a mixture of isoamyl hexanoates. In a preferred embodiment, the at least one ester is isoamyl hexanoates. In one embodiment, the chemical formulation comprises propanoic acid and isoamyl hexanoates. In certain embodiments, the formulation may additionally comprise cineole, valencene, salts or any other additive, excipient or other component desired to produce a formulation having the desired characteristic.

In one embodiment, the ratio of propanoic acid:isoamyl hexanoates is about 7:2 v/v. It should be appreciated that the chemical formulation of System 3 is not limited to any particular ratio of such chemical components. In another embodiment, the chemical formulation of System 3 consists of a single organic acid component and a single ester component. In another embodiment, the chemical formulation of System 3 consists of a single organic acid component and a mixture of isoamyl hexanoates. In such an embodiment, the formulation consists of propanoic acid:isoamyl hexanoates at the ratios described above. In another embodiment, the chemical formulation consists essentially of propanoic acid and isoamyl hexanoates at a ratio of propanoic acid:isoamyl hexanoates of about 7:2 v/v.

In another embodiment, the chemical formulation of System 3 may be added to a carrier such as, without limitation, bentonite, zeolite, perlite or other silica based carriers, in amounts that are effective in killing bacteria and reducing harmful and noxious odors.

This rate is usually between 1.0 to 1.5 ml of System 3 to 224 g of the carrier V/W or in other appropriate ratios that are effective, without limitation, such as between 0.1 to 5 ml of System 3 to 224 g of the carrier V/W, or between 0.5 to 2 ml of System 3 to 224 g of the carrier V/W.

System 4

As contemplated herein, the chemical formulation of the present invention may comprise at least one organic acid and at least one ester. In a preferred embodiment, the at least one acid is propanoic acid. In one embodiment, the at least one ester is isoamyl formate. In another embodiment, the at least one ester may be any single carbon (acid) component ester. In one embodiment, the chemical formulation comprises propanoic acid and isoamyl formate. In certain embodiments, the formulation may additionally comprise cineole, valencene, salts or any other additive, excipient or other component desired to produce a formulation having the desired characteristic.

In one embodiment, the ratio of propanoic acid:isoamyl formate is about 7:2 v/v. It should be appreciated that the chemical formulation of System 4 is not limited to any particular ratio of such chemical components. In another embodiment, the chemical formulation of System 4 consists of a single organic acid component and a single ester component. In such an embodiment, the formulation consists of propanoic acid:isoamyl formate at the ratios described above. In one embodiment, the chemical formulation consists essentially of propanoic acid and isoamyl formate at a ratio of propanoic acid:isoamyl formate of about 7:2 v/v.

As contemplated herein, the present invention may include any chemical formulation of System 4 plus the addition of at least one endophytic fungus. As demonstrated herein, endophytic fungi of the group *F. subglutinans* and others are particularly suited to grow on and degrade human wastes. In addition, the fungus is only able to grow on the liquid and solid waste combination when another antimicrobial mixture such as System 4 is applied and this mixture maximally allows for fungal growth whilst killing bacteria and other microbes. In one embodiment, the fungus is *Fusarium subglutinans*. In yet another embodiment, the present invention includes a chemical formulation comprising a 7:2 mixture of propanoic acid and isoamyl formate, and optionally with the addition of a *Fusarium subglutinans*. In this embodiment, the propanoic acid/isoamyl formate mixture is suitable for killing selected microorganisms without killing the *Fusarium* spp., which can further enhance the recycling of a waste product to which the formulation is applied. In one embodiment, the fungus is incorporated into System 4 via inoculated barley.

In one embodiment, System 4 includes propanoic acid: isoamyl formate in the ratio of 7:2 v/v, which is then added at the rate of 1/10 V/W of the mixture to the dry weight of the carrier substance such as bentonite, perlite or zeolite etc. Barley inoculated with *Fusarium subglutinans* may also be added. This mixture is then added to a container, such as a plastic bag, used to treat and dispose of human wastes. It allows for the rapid growth of *Fusarium subglutinans*. Other items may also be added to the bag including liquid absorbing polymers in appropriate amounts, as would be understood by those skilled in the art.

System 5

As described elsewhere herein, the chemical formulation may comprise two organic acids and at least one ester. For example, in one embodiment, the formulation includes propanoic acid:isobutryic acid:isoamyl hexanoates. In one embodiment, the ratio of propanoic acid:isobutryic acid: isoamyl hexanoates is about 3.5:3.5:2 v/v/v. In another embodiment, the mixture of propanoic acid:isobutryic acid: isoamyl hexanoates is about 7 parts of the two acids and 2 parts of the selected ester. It should be appreciated that the chemical formulation of System 5 is not limited to any particular ratio of such chemical components. In another embodiment, the chemical formulation of System 5 consists of only two organic acids and a single ester. In such an embodiment, the formulation consists of propanoic acid: isobutryic acid:isoamyl hexanoates at the ratios described above. In certain embodiments, the formulation may additionally comprise cineole, valencene, salts or any other additive, excipient or other component desired to produce a formulation having the desired characteristic.

In another embodiment, the chemical formulation of System 5 may be added to a carrier such as, without limitation, bentonite, zeolite, perlite or other silica based carriers, in amounts that are effective in killing bacteria and reducing harmful and noxious odors.

System X

As contemplated herein, the present invention may include any chemical formulation of Systems 1-5 in combination with at least one of a salt, excipient, nutritional additive or supplement. In a preferred embodiment, the chemical formulation is System 3. As demonstrated herein, a chemical formulation comprising System 3, at least one nutritional supplement, and at least one salt is useful for treating diseases and disorders associated with a microbial infection. Examples of nutritional supplements include, but are not limited to, sugars such as glucose, sucrose, or fructose, amino acids such as glycine, and protein sources such as whey protein. Any protein source may be used, as would be understood by one skilled in the art. Non-limiting examples of salts include potassium chloride, sodium chloride, magnesium sulfate, monopotassium phosphate, potassium sulfate, and magnesium acetate. Salts are useful in the formulations of the invention as they enhance electrolyte balance in a subject. Any amount of salt may be used in the compositions of the inventions. It is preferred that the amount of salt is greater than 0%. The presence of System 3 inhibits and kills pathogenic bacteria. In one embodiment, System X includes the chemical formulation of System 3, glucose, whey protein, potassium chloride, magnesium sulfate, and sodium chloride. In another embodiment, System X includes the chemical formulation of System 3, glucose, glycine, potassium chloride, sodium chloride, and magnesium acetate. In another embodiment, System X includes the chemical formulation of System 3, glucose, glycine, potassium chloride, sodium chloride, magnesium acetate, and monopotassium phosphate. It should be appreciated that the chemical formulation of System X is not limited to any particular ratio of such chemical components. In one embodiment, the amount of organic acid is about 100% and the amount of ester is 0%. In another embodiment, the amount of organic acid is about 99% and the amount of ester is about 1%. In another embodiment, the amount of organic acid is about 1% and the amount of ester is about 99%.

In certain embodiments, System X is formulated using one or more pharmaceutically acceptable excipients or carriers. Examples of pharmaceutically acceptable carriers include biological surfactants sold under the trademark CREMOPHOR®, or any other biological surfactant as would be understood by one skilled in the art. In one embodiment, System X includes the chemical formulation of System 3 and a biological surfactant sold under the trademark CREMOPHOR®.

In certain embodiments, Systems 2 and 4 may be used with or without a carrier to treat animal wastes (including human waste) in the presence of *Fusarium subglutinans*. In such embodiments, the present invention inhibits and kills bacteria while at the same time allowing for the growth of the *F. subglutinans* that will eventually break down or cause decay of the solid material in the human waste.

In certain embodiments, the formulae of the present invention are used to fumigate seeds that are contaminated with a microorganism.

In certain embodiments, the formulae of the present invention are administered as a gaseous formula without water or any additional carriers.

Methods

Decontaminating human wastes is only one problem associated with the waste treatment process. An additional problem addressed by the present invention is the need to begin the immediate degradation process of the organic material in the solid and liquid wastes. The biology and biochemistry that occurs when solid and liquid wastes combine is complex. It turns out the urea in urine is immediately attacked by the enzyme urease found in most microbes associated with solid waste with the concomitant production of ammonia gas. The gas itself is harmful and produces an awful odor. Also it is lethal to most fungi as it causes an increase in pH. Thus if one wishes to cause waste degradation, it is essential to stop ammonia production which is desirable for fungal growth and for ammonia remediation in the environment. Each of Systems 1-4 cause killing and inhibition of bacterial growth and subsequent ammonia production, and Systems 2 and 4 further allows for the ready growth of *Fusarium subglutinans* which then degrades the waste. Thus, Systems 1 and 3 are particularly suited to treat animal bedding, wastes etc. with the reduction of ammonia.

The discovery of the appropriate microorganism to bring about the rapid decay of human and animal waste began with the consideration that microbes living within plants (namely, the endophytes) would be an appropriate place to begin the search. Endophytes are the first microbes that are involved in the degradation of a plant when it dies of either natural causes or environmental damage. They have a set of enzymes that degrades the cellulose, lignin and hemicelluloses found in plant materials. These are the same complex organic materials that are found in human solid wastes; therefore, in order to tackle the problem with which the present application is concerned, namely, the degradation of human and animal wastes, a number of endophytic microbes were located and tested for their ability to grow on both solid and liquid human wastes. In order for the microbe to degrade the waste it must either be insensitive to the ammonia that is produced or the ammonia must be eliminated from the equation. Therefore, using Systems 2 and/or 4, which allows for the growth of *Fusarium* spp. and the elimination of ammonia production, it is possible to devise a useable and logical means to treat liquid and solid wastes.

In one aspect, the present invention includes a method of treating human or animal waste. In one embodiment, the method comprises contacting human or animal waste with a composition of the present invention, wherein the composition kills or reduces bacteria growth on the human or animal waste. In one embodiment, the composition comprises a chemical formulation of the present invention. In one embodiment, the chemical formulation further comprises at least one fungus. In another embodiment, the at least one fungus increases the rate of decomposition of the human or animal waste.

In another aspect, the present invention includes a method of eliminating or reducing microbial growth at a treatment site. In one embodiment, the method comprises contacting the treatment site with a composition of the present invention, wherein the composition kills or reduces bacteria growth on the human or animal waste. In one embodiment, the composition comprises a chemical formulation of the present invention. In one embodiment, the chemical formulation further comprises at least one fungus.

In another aspect, the present invention includes a method of eliminating or reducing odor formation at a treatment site. In one embodiment, the method comprises contacting the treatment site with a composition of the present invention, wherein the composition eliminates or reduces odor formation on the human or animal waste.

In another aspect, the present invention includes a method of eliminating or reducing the amount of ammonia at a treatment site. In one embodiment, the method comprises contacting the treatment site with a composition of the present invention, wherein the composition eliminates or reduces the amount of ammonia on the human or animal waste.

In another aspect, the present invention includes a method of fumigating seeds that are contaminated with a microorganism. In one embodiment, the method comprises contacting the seeds with a composition of the present invention, wherein the composition reduces or eliminates microbial growth on the seeds, and in some embodiments, reduces or eliminates microbial growth on the seeds without significantly disrupting germination.

In certain embodiments, the formulae of the present invention may be used in hospital areas to treat human wastes in combination with a carrier to be placed in bed pans to stop contamination of the area with fecal bacteria. In certain embodiments the formulae of the present invention may be used as an antiseptic to treat cuts and wounds and surface infections in animals and people. For example, the present invention may be used to treat bacterial and viral gut infections in people and animals. It is to be noted that all ingredients of Systems 1-4 are GRAS listed and as such are safe. In particular, 10 ml of S-3 has been consumed by a human with no adverse effects. The compositions and formulations of the present invention may also be used to treat or disinfect the surfaces of inanimate or non-living objects, or to spray or apply topically to all types of plants, such as agricultural fruits, vegetables, grains and the like, or to be applied topically, ingested or inhaled by any type of animal, such as livestock or humans.

In one aspect, the present invention includes a method of preserving a fruit. In one embodiment, the method comprises administering to the fruit an effective amount of a composition of the present invention. In one embodiment, the fruit is a raspberry or a grape.

In certain embodiments, the formulae of the present invention, and preferably S-3, may be used to disinfest corn that is used for the fermentation to alcohol.

Mastitis is an infection of the tissues of a cow's udder. Almost any bacterial or mycotic organism that can opportunistically invade tissue and cause infection can cause mastitis. It represents one of the most important problems in dairy production. Most mastitis infections are caused by various species of streptococci, staphylococci, and gram-negative rods, especially lactose-fermenting organisms of enteric origin, commonly termed coliforms and these include such organisms as *Escherichia coli* and *Staphlycoccus aureus*. From an epidemiologic standpoint, the source of infection may be regarded as contagious or environmental and cows are in constant threat of getting infected with these agents.

Except for *Mycoplasma* spp, which may spread from cow to cow through aerosol transmission and invade the udder subsequent to bacteremia, contagious pathogens are spread during milking by milkers' hands or the liners of the milking unit. The chief bacterial species that utilize this mode of transmission include *Staphylococcus aureus, Streptococcus agalactiae*, and *Corynebacterium bovis*. Most other species are opportunistic invaders from the cow's environment, although some other streptococci and staphylococci may also have a contagious component.

Intramammary infections are often described as subclinical or clinical mastitis. Subclinical mastitis is the presence of an infection without apparent signs of local inflammation or systemic involvement. Although transient episodes of abnormal milk or udder inflammation may appear, these infections are for the most part asymptomatic and, if the infection persists for at least 2 months, are termed chronic. Once established, many of these infections persist for entire lactations or the life of the cow. Detection is best done by examination of milk for somatic cell counts (predominantly neutrophils) using either the California Mastitis Test or automated methods provided by dairy herd improvement organizations. Somatic cell counts are positively correlated with the presence of infection. Although variable (especially if determined on a single analysis), cows with a somatic cell count of 2:280,000 cells/mL (2: a linear score of 5) have a >80% chance of being infected. Likewise, the higher the somatic cell count in a herd bulk tank, the higher the prevalence of infection in the herd. Causative agents must be identified by bacterial culture of milk.

Clinical mastitis is an inflammatory response to infection causing visibly abnormal milk (eg, color, fibrin clots). As the extent of the inflammation increases, changes in the udder (swelling, heat, pain, redness) may also be apparent. Clinical cases that include only local signs are referred to as mild or moderate. If the inflammatory response includes systemic involvement (fever, anorexia, shock), the case is termed severe. If the onset is very rapid, as often occurs with severe clinical cases, it is termed an acute case of severe mastitis. More severely affected cows tend to have more serous secretions in the affected quarter.

Although any number of quarters can be infected simultaneously in subclinical mastitis, typically only one quarter at a time will display clinical mastitis. However, it is not uncommon for clinical episodes caused by *Mycoplasma* to affect multiple quarters. Gangrenous mastitis can also occur, particularly when subclinical, chronic infections of *Streptococcus aureus* become severe at times of immunosuppression (eg, at parturition). As with subclinical mastitis, culture of milk samples collected from affected quarters is the only reliable method to determine the etiology of clinical cases.

All dairy herds have cows with subclinical mastitis; however, the prevalence of infected cows varies from 15-75%, and quarters from 5-40%. Many different pathogens can establish a chronic infection that will only on occasion manifest clinical signs of mastitis. The primary focus of most subclinical mastitis programs is to reduce the prevalence of the contagious pathogens *Streptococcus agalactiae* and *Staphylococcus aureus*, as well as other gram-positive cocci, most notably *Streptococcus dysgalactiae* (which may also be contagious or an environmental pathogen), *Streptococcus uberis*, enterococci, and numerous other coagulase-negative staphylococci, including *Streptococcus hyicus, Streptococcus epidermidis, Streptococcus xylosus*, and *Streptococcus intermedius*.

For contagious pathogens, adult lactating cattle are most at risk for infection, either while lactating or during the dry period. The primary reservoir of infection is the mammary gland; transmission occurs at milking with either milkers' hands or milking equipment acting as fomites. Primiparous heifers have been reported to be infected with staphylococci and streptococci prior to calving, although the prevalence varies greatly among herds and geographic regions. Teat-end dermateatis caused by the horn fly, *Haematobia irritans*, which can harbor *Streptococcus aureus*, has been associated with increased risk of infection in heifers, especially in warmer climates.

Commonly used treatments include the use of antibiotics, which pose a threat to the milk being acquired from the animal since the antibiotics will make their way into the udder. Milk cannot be used for at least 3 days after the administration of the antibiotic. The use of immunization is not possible since there are a large number of potential pathogens involved in the mastitis disease. The general recommendation is for sanitation practices to be intensified with cleanliness in the milking parlor and in the areas frequented by the animals. Currently, no available treatment has been found to be both effective and safe for the treating mastitis.

In one aspect, the present invention includes a method of treating an animal having a disease or disorder associated with a microbial infection. In one embodiment, the method comprises administering to the animal an effective amount of a composition of the present invention. In another embodiment, the method comprises administering to the animal an effective amount of a composition comprising an organic acid. Such diseases and disorders may include, without limitation, diarrheal diseases such as scours, food poisoning, or stomach flu, or intramammary infections such as subclinical or clinical mastitis. It should be further appreciated that the formulae and compositions of the present invention are not limited to treatment of any particular type of subject. As contemplated herein, the subject may be any animal, preferably a mammal, and more preferably livestock, such as cattle, sheep, or swine, or even a human. In one embodiment, the animal is bovine, porcine, or ovine. In another embodiment, the animal is human.

In another aspect, the present invention includes a method of treating a cow having scours. In one embodiment, the method comprises administering to the cow an effective amount of a composition of the present invention.

In another aspect, the present invention includes a method of treating a pig having scours. In one embodiment, the method comprises administering to the pig an effective amount of a composition of the present invention.

In another aspect, the present invention includes a method of treating a cow having mastitis. In one embodiment, the method comprises administering to the cow an effective amount of a composition of the present invention.

In another aspect, the present invention includes a method of treating a sheep having mastitis. In one embodiment, the method comprises administering to the sheep an effective amount of a composition of the present invention.

In another aspect, the present invention includes a method of treating a human having a diarrheal disease. In one embodiment, the method comprises administering to the human an effective amount of a composition of the present invention. In one embodiment, the diarrheal disease is food poisoning or stomach flu.

Combination Therapy

The compositions of the present invention are intended to be useful in combination with one or more additional compounds. In non-limiting examples, the compositions of the invention may be used in combination with one or more therapeutic agents (or a salt, solvate or prodrug thereof). Non-limiting examples of therapeutic agents include antibiotics such as Baytril, sulfonamides, Nuflor, Tylan 40-50, Excede, Noromycin LA, Draxxin, and tetracycline, vaccines such as Inforce 3, multivitamins, probiotics, and toxin absorbants such as Toxiban, or other therapeutic agents such as Suprio.

In another embodiment, the compositions of the invention may be used in combination with a detergent. In one embodiment, the detergent acts as a solubilizing agent for the composition while removing unwanted bacterial laden debris from the area of infection of the subject, and any other possible sources of infection, such as bedding, tools, or places where the subject lives. In a non-limiting example, the compositions of the present invention are useful for treating the udder, the bedding used for housing cattle, which is the primary source of environmental pathogens, as well as tools used in the milking process which have all been identified as potential sources of infection, such as contaminated teat dips, intramammary infusions, water hoses used for udder preparation during milking, water ponds or mud holes, skin lesions, teat trauma, and flies. Non-limiting examples of detergents include Sucragel CF, Chemoxide CAW, BioSoft D40, Lathanol LAL, BioTerge AS-40, Nacconol 90G, and potassium cocoate.

Pharmaceutical Compositions and Therapies

Administration of a composition useful within the invention may be achieved in a number of different ways, using methods known in the art. The therapeutic and prophylactic methods of the invention thus encompass the use of pharmaceutical compositions comprising the compositions useful within the invention to practice the methods of the invention. The pharmaceutical compositions useful for practicing the invention may be administered to deliver a dose of 1 ng/kg/day to 100 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Although the description of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Typically, dosages which may be administered in a method of the invention to an animal, preferably a human, range in amount from 0.5 μg to about 50 mg per kilogram of body weight of the animal. While the precise dosage administered will vary depending upon any number of factors, including but not limited to, the type of animal and type of disease state being treated, the age of the animal and the route of administration, the dosage of the composition will preferably vary from about 1 μg to about 10 mg per kilogram of body weight of the animal. More preferably, the dosage will vary from about 3 μg to about 1 mg per kilogram of body weight of the animal.

Pharmaceutical compositions that are useful in the methods of the invention may be prepared, packaged, or sold in compositions suitable for oral, parenteral, topical, buccal, or another route of administration. Other contemplated compositions include projected nanoparticles, liposomal preparations, resealed erythrocytes containing the active ingredient, and immunologically-based compositions.

The pharmaceutical compositions described herein may be prepared by any method known or hereafter developed in the art of pharmacology. In general, such preparatory methods include the step of bringing the active ingredient into association with a pharmaceutically acceptable carrier or one or more other accessory ingredients, and then, if necessary or desirable, shaping or packaging the product into a desired single- or multi-dose unit.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

In one embodiment, the compositions of the invention are formulated using one or more pharmaceutically acceptable excipients or carriers. In one embodiment, the pharmaceutical compositions of the invention comprise a therapeutically effective amount of a composition of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Compositions may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The pharmaceutical composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The pharmaceutical composition preferably includes an anti-oxidant and a chelating agent that inhibits the degradation of the formulation. Preferred antioxidants for some formulation are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some formulations, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Controlled- or sustained-release formulations of a composition of the invention may be made using conventional technology, in addition to the disclosure set forth elsewhere herein. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the compositions of the invention.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, nanoparticles, or microspheres or a combination thereof that facilitates the controlled-release of the active ingredient.

Administration/Dosing

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic composition necessary to achieve a therapeutic effect may vary according to factors such as the activity of the particular composition employed; the time of administration; the rate of excretion of the composition; the duration of the treatment; other drugs, compositions or materials used in combination with the composition; the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic composition of the invention is from about 1 and 5,000 mg/kg of body weight/per day. One of ordinary skill in the art would be able to study the relevant factors and make the determination regarding the effective amount of the therapeutic composition without undue experimentation.

The composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The compositions of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compositions of the invention employed in the pharmaceutical composition at levels lower than that required in order to achieve the desired therapeutic effect and gradually increase the dosage until the desired effect is achieved.

In particular embodiments, it is especially advantageous to formulate the composition in dosage unit form for ease of administration and uniformity of dosage. Dosage unit form as used herein refers to physically discrete units suited as unitary dosages for the subjects to be treated; each unit containing a predetermined quantity of therapeutic composition calculated to produce the desired therapeutic effect in association with the required pharmaceutical vehicle. The dosage unit forms of the invention are dictated by and directly dependent on (a) the unique characteristics of the therapeutic composition and the particular therapeutic effect to be achieved, and (b) the limitations inherent in the art of compounding/formulating such a therapeutic composition for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compositions of the invention for administration may be in the range of from about 0.1 mg to about 1,000 mg, about 0.2 mg to about 950 mg, about 0.4 mg to about 900 mg, about 1 mg to about 850 mg, about 5 mg to about 750 mg, about 20 mg to about 700 mg, about 30 mg to about 600 mg, about 50 mg to about 500 mg, about 75 mg to about 400 mg, about 100 mg to about 300 mg, about 120 mg to about 250 mg, and any and all whole or partial increments therebetween.

In some embodiments, the dose of a composition of the invention is from about 1 mg and about 2,500 mg. In some embodiments, a dose of a composition of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second composition (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof In one embodiment, the present invention is directed to a packaged pharmaceutical composition comprising a container holding a therapeutically effective amount of a composition of the invention, alone or in combination with a second pharmaceutical agent; and instructions for using the composition to treat, prevent, or reduce one or more symptoms of a disease in a subject.

Routes of Administration

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

For oral administration, the compositions of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, and OY-PM Type film coating systems).

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconsteatution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compositions of the invention, and a further layer providing for the immediate release of a medication for treatment of a disease. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconsteatution with a suitable vehicle (e.g. sterile pyrogen-free water) prior to parenteral administration of the reconsteatuted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations that are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

A pharmaceutical composition of the invention may be prepared, packaged, or sold in a formulation suitable for topical administration. There are several advantages to delivering compositions, including drugs or other therapeutic agents, into the skin (dermal drug delivery) or into the body through the skin (transdermal drug delivery). Transdermal composition delivery offers an attractive alternative to injections and oral medications. Dermal composition delivery offers an efficient way to deliver a composition to the skin of a mammal, and preferably a human, and provides a method of treatment of the skin, or otherwise provides a method of affecting the skin, without the need to break or damage the outer layer of the skin. In the present invention, dermal delivery, by way of a dermally-acting composition of the invention, provides these advantages for treatment of a skin-related condition, disorder or disease.

A number of compounds, including some drugs, will penetrate the skin effectively simply because the molecules are relatively small and potent at small doses of 0.1 mg to 15 mg/day (Kanikkannan et al., 2000, Curr. Med. Chem. 7:593-608). Many other compounds and drugs can be delivered only when an additional enhancement system is provided to "force" them to pass through the skin. Among several methods of transdermal drug delivery are electroporation, sonophoresis, iontophoresis, permeation enhancers (cyclodextrins), and liposomes. While the aforementioned methods are also included in the present invention for dermal delivery of the compositions of the invention, liposomes represent a preferred dermal delivery method.

The composition of the invention may consist of the active ingredient alone, in a form suitable for administration to a subject, or the composition may comprise at least one active ingredient and one or more pharmaceutically acceptable carriers, one or more additional ingredients, or some combination of these. The active ingredient may be present in the composition in the form of a physiologically acceptable ester or salt, such as in combination with a physiologically acceptable cation or anion, as is well known in the art. Compositions of the invention will also be understood to encompass pharmaceutical compositions useful for treatment of other conditions, disorders and diseases associated with the skin.

In one aspect, a dermal delivery vehicle of the invention is a composition comprising at least one first compound that can facilitate dermal delivery of at least one second compound associated with, or in close physical proximity to, the composition comprising the first compound. As will be understood by the skilled artisan, when armed with the disclosure set forth herein, such delivery vehicles include, but should not be limited to, liposomes, nanosomes, phospholipid-based non-liposome compositions (eg., selected cochleates), among others.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 0.001% to about 90% (w/w) active ingredient, although the concentration of the active ingredient may be as high as the solubility limit of the active ingredient in the solvent. Formulations for topical administration may further comprise one or more of the additional ingredients described herein.

In one aspect of the invention, a dermal delivery system includes a liposome delivery system, and that the present invention should not be construed to be limited to any particular liposome delivery system. Based on the disclosure set forth herein, the skilled artisan will understand how to identify a liposome delivery system as being useful in the present invention.

The present invention also encompasses the improvement of dermal and transdermal drug delivery through the use of penetration enhancers (also called sorption promoters or accelerants), which penetrate into skin to reversibly decrease the barrier resistance. Many compounds are known in the art for penetration enhancing activity, including sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes. Other enhancers include oleic acid, oleyl alcohol, ethoxydiglycol, laurocapram, alkanecarboxylic acids, dimethylsulfoxide, polar lipids, or N-methyl-2-pyrrolidone.

In alternative embodiments, the topically active pharmaceutical or cosmetic composition may be optionally combined with other ingredients such as moisturizers, cosmetic adjuvants, anti-oxidants, chelating agents, surfactants, foaming agents, conditioners, humectants, wetting agents, emulsifying agents, fragrances, viscosifiers, buffering agents, preservatives, sunscreens and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art.

In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art. The compositions of this invention may also contain active amounts of retinoids (i.e., compounds that bind to any members of the family of retinoid receptors), including, for example, tretinoin, retinol, esters of tretinoin and/or retinol and the like.

The composition of the invention may comprise a preservative from about 0.005% to 2.0% by total weight of the composition. The preservative is used to prevent spoilage in the case of an aqueous gel because of repeated patient use when it is exposed to contaminants in the environment from, for example, exposure to air or the patient's skin, including contact with the fingers used for applying a composition of the invention such as a therapeutic gel or cream. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the composition for use in the invention in the aqueous gel formulation. Preferred antioxidants for some compounds are BHT, BHA, alpha-tocopherol and ascorbic acid in the preferred range of about 0.01% to 5% and BHT in the range of 0.01% to 1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Additional components may include, but should not be limited to those including water, oil (eg., olive oil/PEG7), biovera oil, wax (eg., jojoba wax), squalene, myristate (eg., isopropyl myristate), triglycerides (eg., caprylic triglyceride), Solulan 98, cocoa butter, rhea butter, alcohol (eg., behenyl alcohol), stearate (eg., glycerol-monostearate), chelating agents (eg., EDTA), propylene glycol, SEPIGEL (Seppic, Inc., Fairfield, N.J.), silicone and silicone derivatives (eg., dimethicone, cyclomethicone), vitamins (eg., vitamin E), among others.

Buccal Administration

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475; 6,488,962; 6,451,808; 5,972,389; 5,582,837 and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology, using for example proteins equipped with pH sensitive domains or protease-cleavable fragments. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gel-caps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased subject compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compositions may be formulated with a suitable polymer or hydrophobic material that provides sustained release properties to the compositions. As such, the compositions for use the method of the invention may be administered in the form of microparticles, for example, by injection or in the form of wafers or discs by implantation.

In a preferred embodiment of the invention, the compositions of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Accordingly, in one embodiment, the present invention relates to a chemical formulation comprising propanoic acid, isobutyric acid, at least one ester, and at least one carrier, wherein the chemical formulation has antibacterial activity when applied to human or animal waste. In another embodiment, the at least one ester is isoamyl butyrate. In another embodiment, the at least one carrier is a silica based carrier. In another embodiment, the at least one carrier is selected from the group consisting of bentonite, zeolite and perlite. In another embodiment, the ratio of propanoic acid:isobutyric isoamyl butyrate is about 3.5:3.5:2 v/v/v. In another embodiment, the ratio of propanoic acid, isobutyric acid and isoamyl butyrate is about 7 parts of the two acids and 2 parts of isoamyl butyrate. In another embodiment, the chemical formulation consists essentially of propanoic acid, isobutyric acid, isoamyl butyrate and a carrier. In another embodiment, the carrier is selected from the group consisting of bentonite, zeolite and perlite. In another embodiment, the chemical formulation has antibacterial activity when applied to human or animal waste.

In another embodiment, the present invention relates to a chemical formulation comprising, propanoic acid, isobutryic acid, at least one ester, at least one carrier, and at least one fungus. In another embodiment, the at least one ester is isoamyl butyrate. In another embodiment, the at least one carrier is a silica based carrier. In another embodiment, the at least one carrier is selected from the group consisting of bentonite, zeolite and perlite. In another embodiment, the ratio of propanoic acid:isobutryic acid:isoamyl butyrate is about 3.5:3.5:2 v/v/v. In another embodiment, the ratio of propanoic acid, isobutryic acid and isoamyl butyrate is about 7 parts of the two acids and 2 parts of isoamyl butyrate. In another embodiment, the at least one fungus is an endophyte. In another embodiment, the endophyte is of the genus *Fusarium*. In another embodiment, the endophyte is *F. subglutinans*.

In another embodiment, the present invention relates to a chemical formulation comprising propanoic acid and at least one 6-12 carbon (acid) component ester, wherein the chemical formulation has a ratio of propanoic acid:ester component of about 7:2 v/v. In another embodiment, the at least one ester is isoamyl hexanoates. In another embodiment, the formulation further includes at least one nutritional supplement and at least one salt. In another embodiment, the formulation comprises glucose, whey protein, potassium chloride, magnesium sulfate, and sodium chloride. In another embodiment, the formulation comprises glucose, glycine, potassium chloride, sodium chloride, and magnesium acetate. In another embodiment, the formulation comprises glucose, glycine, potassium chloride, sodium chloride, magnesium acetate, and monopotassium phosphate. In another embodiment, the formulation includes at least one pharmaceutically acceptable carrier. In another embodiment, the carrier is a pharmaceutically acceptable carrier sold under the trademark CREMOPHOR®. In another embodiment, the formulation consists essentially of propanoic acid and isoamyl hexanoates at a ratio of propanoic acid:isoamyl hexanoates of about 7:2 v/v. In another embodiment, the present invention relates to a chemical formulation consisting essentially of propanoic acid, isoamyl hexanoates and a carrier.

In another embodiment, the present invention relates to a chemical formulation comprising propanoic acid and a single carbon (acid) component ester, wherein the chemical formulation has a ratio of propanoic acid:ester component of about 7:2 v/v. In another embodiment, the at least one ester is isoamyl formate. In another embodiment, the formulation consists essentially of propanoic acid and isoamyl formate at a ratio of propanoic acid:isoamyl formate of about 7:2 v/v. In another embodiment, the formulation includes at least one carrier. In another embodiment, the at least one carrier is a silica based carrier. In another embodiment, the at least one carrier is selected from the group consisting of bentonite, zeolite and perlite. In another embodiment, the chemical formulation consists essentially of propanoic acid, isoamyl formate and a carrier.

In another embodiment, the present invention includes a chemical formulation comprising propanoic acid, isoamyl formate, and at least one fungus. In another embodiment, the ratio of propanoic acid:isoamyl formate is about 7:2 v/v. In another embodiment, the at least one fungus is an endophyte. In another embodiment, the endophyte is of the genus *Fusarium*. In another embodiment, the endophyte is *F. subglutinans*.

In another embodiment, the present invention relates to a method of treating human or animal waste, comprising contacting human or animal waste with a composition comprising propanoic acid, isobutyric acid and at least one ester, wherein the composition kills or reduces bacteria growth on the human or animal waste. In another embodiment, the present invention relates to a method of treating human or animal waste, comprising contacting human or animal waste with a composition comprising propanoic acid, isobutyric acid, at least one ester and at least one fungus, wherein the propanoic acid, isobutyric acid and at least one ester kills or reduces bacteria growth on the human or animal waste, and the at least one fungus increases the rate of decomposition of the human or animal waste. In another embodiment, the present invention relates to a method of eliminating or reducing microbial growth at a treatment site, comprising contacting the treatment site with a composition comprising propanoic acid and at least one ester at a ratio of propanoic acid:ester of about 7:2, wherein the ester is isoamyl formate or isoamyl hexanoates and the composition kills or reduces bacteria growth on the human or animal waste. In another embodiment, the present invention relates to a method of treating human or animal waste, comprising contacting human or animal waste with a composition comprising propanoic acid, isoamyl formate at a ratio of propanoic acid:isoamyl formate of about 7:2, and at least one fungus, wherein the propanoic acid and isoamyl formate mixture kills or reduces microbial growth on the human or animal waste, and the at least one fungus increases the rate of decomposition of the human or animal waste. In another embodiment, the present invention relates to a method of treating an animal having a disease or disorder associated with a microbial infection, comprising administering to the animal an effective amount of a composition comprising at least one organic acid. In another embodiment, the composition consists essentially of an organic acid. In another embodiment, the composition consists of an organic acid. In another embodiment, the at least one organic acid is propanoic acid. In another embodiment, the at least one organic acid is isobutyric acid. In another embodiment, the animal is a human. In another embodiment, the disease or disorder is a diarrheal disease. In another embodiment, the animal is bovine, porcine, or ovine. In another embodiment, the disease or disorder is selected from the group consisting of a diarrheal disease and an intramammary infection. In another embodiment, the diarrheal disease is scours. In another embodiment, the intramammary infection is subclinical mastitis or clinical mastitis. In another embodiment, the composition further comprises at least one ester. In another embodiment, the at least one ester is isoamyl hexanoates. In another embodiment, the composition further comprises at least one nutritional supplement and at least one salt. In another embodiment, the composition comprises glucose, whey protein, potassium chloride, magnesium sulfate, and sodium chloride. In another embodiment, the composition comprises glucose, glycine, potassium chloride, sodium chloride, and magnesium acetate. In another embodiment, the composition comprises glucose, glycine, potassium chloride, sodium chloride, magnesium acetate, and monopotassium phosphate. In another embodiment, the composition further comprises at least one pharmaceutically acceptable carrier. In another embodiment, the carrier is a pharmaceutically acceptable carrier sold under the trademark CREMOPHOR®. In another embodiment, the composition comprises propanoic acid and isoamyl hexanoates at a ratio of propanoic acid:isoamyl hexanoates of about 7:2 v/v. In another embodiment, the at least one ester is isoamyl hexanoates. In another embodiment, the ratio of propanoic acid:isobutyric acid:isoamyl hexanoates is about 3.5:3.5:2 v/v/v. In another embodiment, the ratio of propanoic acid, isobutyric acid and isoamyl hexanoates is about 7 parts of the two acids and 2 parts of isoamyl butyrate.

In another embodiment, the present invention relates to a chemical formulation consisting essentially of propanoic acid, isobutyric acid, isoamyl hexanoates and a carrier. In another embodiment, the carrier is selected from the group consisting of bentonite, zeolite and perlite. In another embodiment, the chemical formulation has antibacterial activity when applied to human or animal waste.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

Example 1

Discussed below are the various experiments that resulted in the discovery of *F. subglutinans* and the Systems 1 and 2 which can be used in various human and animal waste treatment devices along with animal bedding, stalls etc.

Figure 6:
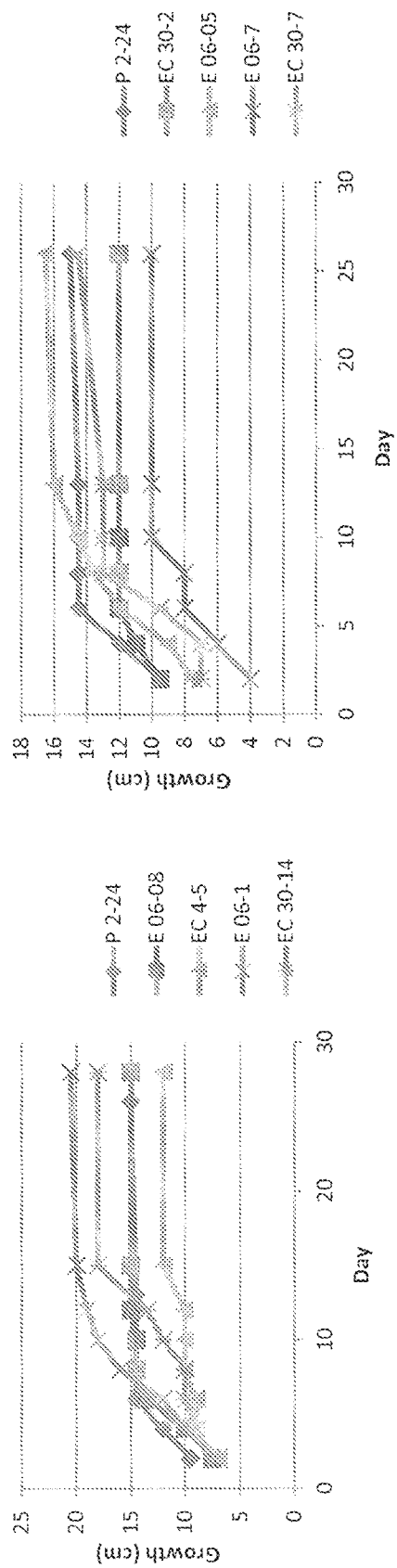
Figure 7:
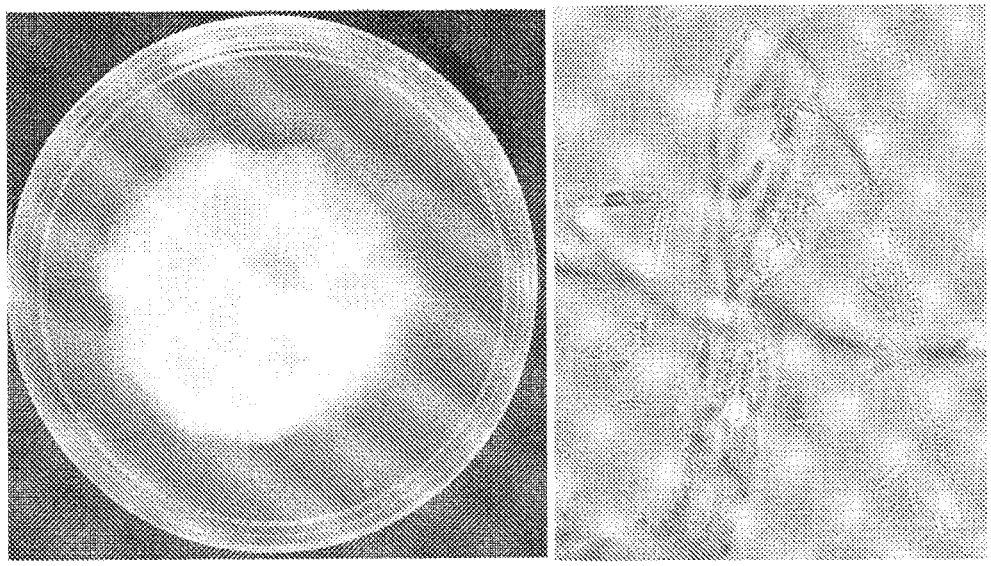
Figure 8:
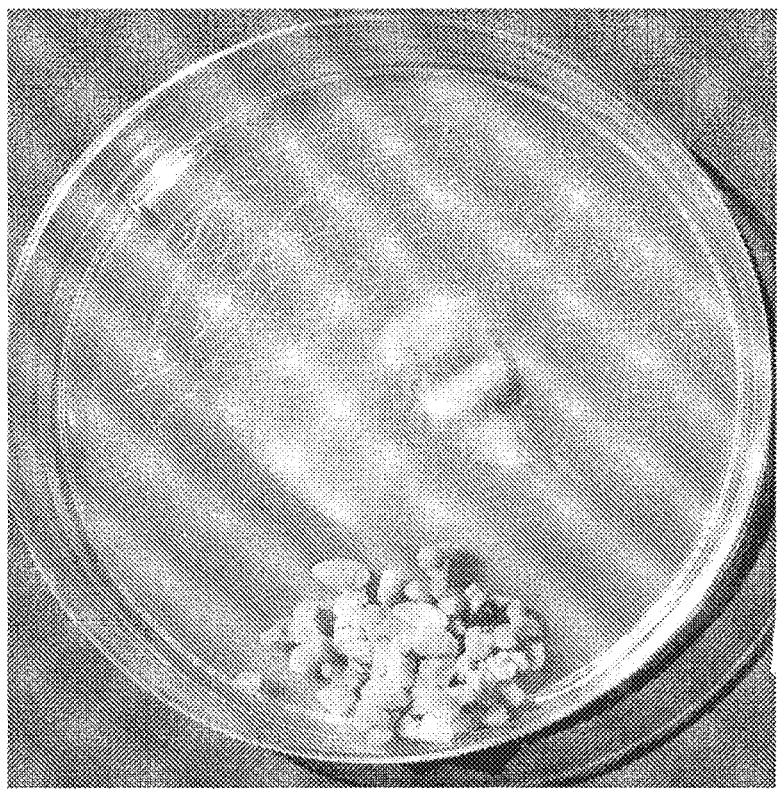
Figure 9:
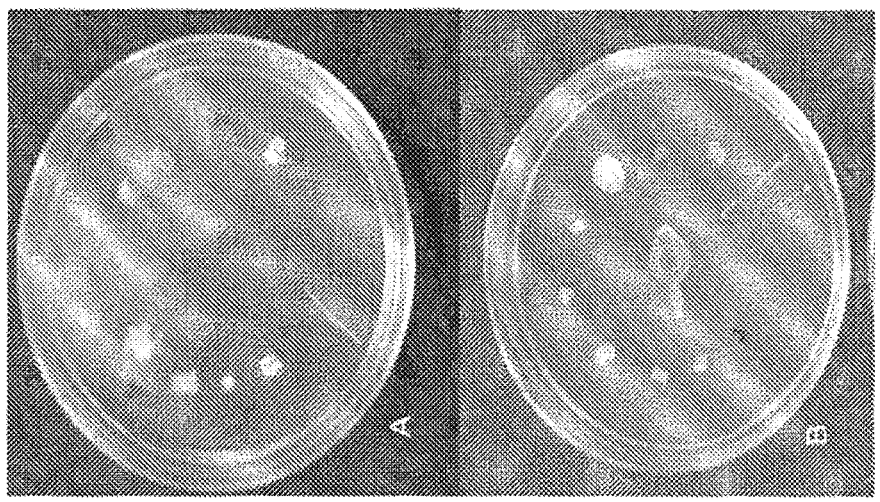

Table 1. Shows the inhibition activities of various esters (used in combination with a 1:1 v/v mix of propanoic acid and isobutryic acid and thus the two acids to esters is 7:2 v/v) to a series of test fungi and bacteria that are commonly used organisms to screen for antibiotic activities. From these data, the Systems 1 and 2 were selected for use in this invention (see highlighted areas on the Table).

Table 2. Molecular genetics data assembled on the various new *Fusarium* spp. Isolates that grow on human wastes in the presence of the System 2 mixture (with carrier of bentonite or zeolite) as described above. From this it is obvious that any of these organisms are nearly equal or, in most cases better than *Fusarium culmorum* (P2-24), the subject of and earlier patent. A Data set on P2-24 is also included.

Table 3. The growth of various fusaria on human wastes causes a reduction of the dry weight of the mass during the course of a 7 week experiment. The experimental set-up contained 0.5 g of bentonite with System 2 on a water agar plate having about 100 mg wet weight of human waste and a small agar plug with the test *fusarium* on it. The incubation period was 7 weeks at 22° C. The remains of the human waste were physically removed and dried for 4 hr at 80° C. and then weighed.

FIG. 1. Indicates how the assays were done to yield the data sets in Table 1. The various esters were combined with a 1:1 mixture of propanoic acid and isobutryic acid and these were added 7:2 V/V with the ester to be tested. Then 9 lll were placed in the center well with the individual test organism agar plugs in the periphery as indicated in the Figure.

FIG. 2. Demonstrates the effectiveness of System 1 (above) in killing and inhibiting human waste associated bacteria. Fresh wastes were collected and then approximately 5 mg were evenly spread on the surface of a potato dextrose agar plate. The plates were incubated for 2 days and then photographed. The panel on the right is an untreated control, the middle contains bentonite 0.5 g with no antibiotic and the left contains 0.5 g with System 1.

FIG. 3. Demonstrates the effectiveness of System 2 (above) in killing and inhibiting human waste associated bacteria. Fresh wastes were collected and then approximately 5 mg were evenly spread on the surface of a potato dextrose agar plate. The plates were incubated for 2 days and then photographed. The panel on the right is an untreated control, the middle contains bentonite 0.5 g with no antibiotic and the left contains 0.5 g with System 2.

FIG. 4. An illustration of how treatment with System 1 can eliminate odors. Two cat litter boxes with cat fecal matter each from 5 different cats ca. 140 g. The box on the left had been treated with System 1 on bentonite with (0.5 ml/100 g bentonite). After 5 days the ammonia readings were 14 ppm on the control (left) and 0 ppm on the treated right. The overall odor was significantly reduced in the treated box.

FIG. 5. Illustrates how the fungus can grow on fresh human waste and reduce the level of odor. Treatment of ca. 140 g of human waste in the presence of urine with *Fusarium subglutinans* 06-1 in the presence of System 2 (1 ml on 10 g of zeolite). After 3 weeks there was substantial growth of the *F. subglutinans* (white mycelium in the right container). The ammonia level was 71.4 in the control on the left and 12.1 in the treated container on the right.

FIG. 6. The growth of various new isolates of *Fusarium* spp. as compared to the growth of *F. culmorum* (P-2-24) on human waste are shown here. The progressive growth of *Fusarium* spp on small dollops of human waste are shown here ca. 100 mg (fresh weight) over the course of many days. The growth of newly isolated and characterized *Fusarium* spp. are each compared to P2-24 which is *Fusarium culmorum*, the subject of a previous patent on this topic. The new *Fusarium* spp. especially E06-1 and E06-5 do grow faster on the waste. Growth was measured from the extent of the mycelium moving out from the agar plug placed on the dollop of waste.

FIG. 7. Top-A six day old culture of *Fusarium subglutinans* E06-1 the preferred fungus to be used to treat human and animal wastes in combination with System 2. Bottom a light microscopic view of spores and hyphae of *F. subglutinans*. The spores are slightly curved and are 9.8-12×2.5 !J.

FIG. 8. *Fusarium subglutinans* (E06-8) growing profusely on human waste in the presence of System 2. Please note the inhibition of bacterial growth to the right side of the culture plate which is influenced by the vapors of System 2 emanating from the bentonite particles on the left side of the plate allowing for fungal growth. There were 0.5 g of treated bentonite added, ca 100 mg of human waste and the plate had incubated for 12 days. See FIG. 6 for comparative growth measurements.

Method 1—Experimental Procedure for Isolating *Fusarium* Spp Endophytes

Isolates of *Fusarium* spp. may be collected according to standard protocols understood by those skilled in the art. In brief, twig pieces were thoroughly soaked in 70% aqueous ethanol solution for surface disinfection and then outer bark/epidermis was removed with sterile scalpel. Small pieces of inner bark were aseptically transferred to the surface of water agar (WA) and glycerol-arginine medium (GAM). After incubation for several days at 25° C., hyphal tips of developing fungi should be aseptically removed and placed on potato dextrose agar (PDA). Pure fungal cultures were acquired in this manner. In particular isolates that have a pink to reddish coloration and possessing sickle shaped spores are likely to be endophytic *Fusarium* spp. Further characterization by molecular techniques can be made as understood by those skilled in the art. This procedure was used to find each of the organisms used and described herein.

Shown in Table 1, are the inhibition and killing effects of propanoic acid, and isobutryic acid together and alone and with various esters. The tests were conducted over the course of 30 hr at 22° C. Measurements were made on appropriate controls and thus the percentage of inhibition calculations could be made on treatments vs the growth on a control organism (non-treated). The bacteria and yeast like organisms were evaluated on the basis of relative growth rates after 30 hr. Those highlighted areas on the table show those compounds (esters) having the most compatibility with propanoic and isobutryic acid 1:1 v/v mixtures with the appropriate esters at a 7:2 ratio—Systems 1 and 2 above. It is from this test that Systems 1 and 2 were discovered. The acids were added at 7 !J.l individually and combination of the esters with the acids were added at the 9 !J.l level in the plate assay.

TABLE 1

| Compound tested | *Cercospora beticola* | *Phytophthora cinnamomi* | *Verticillium dahliae* | *Sclerotinia sclerotiorum* | *Pythium ultimum* |
|---|---|---|---|---|---|
| | Test Organism | | | | |
| Control | 0% | 0% | 0% | 0% | 0% |
| Isobutyric Acid + Propanoic Acid | 95% | 87% | 70% | 20% | 89% |
| Isobutyric Acid | 95% | 100% | 90% | 40% | 100% |
| Propanoic Acid | 95% | 67% | 96% | 60% | 91% |
| Ethyl Isobutyrate | 95% | 100% | 80% | 90% | 100% |
| Isopropyl Isobutyrate | 95% | −33% | 96% | 30% | 100% |
| Isobutyl Isobutyrate | 95% | 0% | 92% | 75% | 100% |
| Butyl Isobutyrate | 95% | 0% | 60% | 0% | 100% |
| Isobutyl Butyrate | 100% | 33% | 96% | 70% | 100% |
| Isoamyl Butyrate | 100% | 100% | 100% | 95% | 100% |
| Isoamyl Isobutyrate | 95% | 97% | 96% | 80% | 100% |
| Isobutyl Propionate | 100% | 33% | 88% | 80% | 100% |
| Isobutyl Acetate | 95% | 67% | 60% | 20% | 100% |
| Propyl Isobutyrate | 95% | 87% | 88% | 40% | 98% |
| Isobutyl Isovalerate | 95% | 100% | 96% | 0% | 100% |

| | *Fusarium subglutinans* | *Trichoderma viridae* | *Rhizoctonia solani* | *Aspergillus fumigatus* |
|---|---|---|---|---|
| Control | 0% | 0% | 0% | 0% |
| Isobutyric Acid + Propanoic Acid | −3% | 20% | 86% | 0% |
| Isobutyric Acid | 67% | 27% | 86% | 90% |
| Propanoic Acid | 83% | 53% | 100% | 80% |
| Ethyl Isobutyrate | 67% | 67% | 100% | 80% |
| Isopropyl Isobutyrate | 33% | 20% | 43% | 0% |
| Isobutyl Isobutyrate | 50% | 47% | 86% | 80% |
| Butyl Isobutyrate | 0% | 40% | 97% | 0% |
| Isobutyl Butyrate | 33% | 47% | 100% | 0% |
| Isoamyl Butyrate | 100% | 90% | 100% | 90% |
| Isoamyl Isobutyrate | 67% | 67% | 100% | 80% |
| Isobutyl Propionate | 67% | 40% | 100% | 80% |
| Isobutyl Acetate | 67% | 20% | 57% | 0% |
| Propyl Isobutyrate | 50% | 33% | 97% | 50% |
| Isobutyl Isovalerate | 67% | 20% | 94% | 0% |

| | *Candida albicans* | *Escherichia coli* | *Bacillus subtilis* | *Saccharomyces cerevicae* |
|---|---|---|---|---|
| Control | Growth Observed | Growth Observed | Growth Observed | Growth Observed |
| Isobutyric Acid + Propanoic Acid | Growth Observed | Inhibited | Inhibited | Inhibited |
| Isobutyric Acid | Growth Observed | No Growth | No Growth | Growth Observed |
| Propanoic Acid | Growth Observed | No Growth | No Growth | Growth Observed |
| Ethyl Isobutyrate | Growth Observed | No Growth | No Growth | Growth Observed |

TABLE 1-continued

| Test Organism | | | | |
|---|---|---|---|---|
| Isopropyl Isobutyrate | Growth Observed | No Growth | No Growth | Growth Observed |
| Isobutyl Isobutyrate | Growth Observed | Inhibited | Inhibited | Growth Observed |
| Butyl Isobutyrate | Growth Observed | No Growth | No Growth | Growth Observed |
| Isobutyl Butyrate | Growth Observed | No Growth | No Growth | Growth Observed |
| Isoamyl Butyrate | No Growth | No Growth | No Growth | Growth Observed |
| Isoamyl Isobutyrate | Growth Observed | No Growth | No Growth | Growth Observed |
| Isobutyl Propionate | Growth Observed | No Growth | No Growth | Growth Observed |
| Isobutyl Acetate | Growth Observed | Inhibited | Inhibited | Growth Observed |
| Propyl Isobutyrate | Growth Observed | Inhibited | Inhibited | Growth Observed |
| Isobutyl Isovalerate | Growth Observed | Inhibited | Inhibited | Growth Observed |

Note:
when No Growth or 100% inhibition is noted the organisms were dead and not able to be revived.

Shown in Table 2 is a description of the molecular genetics data (below) obtained on the new isolates of *fusarium* that were tested for their ability to degrade human wastes. Each of these isolates is so designated on the heading. Details of the data acquisition are provided at the end of the table.

TABLE 2

E 06-05 *Fusarium subglutinans*

Sequence (480 bases):
AACATACCAATTGTTGCCTCGGCGGATCAGCCCGCTCCCGGTAAAACGGGACGGCC
CGCCAGAGGACCCCTAAACTCTGTTTCTATATGTAACTTCTGAGTAAAACCATAAAT
AAATCAAAACTTTCAACAACGGATCTCTTGGTTCTGGCATCGATGAAGAACGCAGCA
AAATGCGATAAGTAATGTGAATTGCAGAATTCAGTGAATCATCGAATCTTTGAACGC
ACATTGCGCCCGCCAGTATTCTGGCGGGCATGCCTGTTCGAGCGTCATTTCAACCCT
CAAGCCCAGCTTGGTGTTGGGACTCGCGAGTCAAATCGCGTTCCCCAAATTGATTGG
CGGTCACGTCGAGCTTCCATAGCGTAGTAGTAAAACCCTCGTTACTGGTAATCGTCG
CGGCCACGCCGTTAAACCCCAACTTCTGAATGTTGACCTCGGATCAGGTAGGAATAC
CCGCTGAACTTAAGCATATCAATAA (SEQ ID NO: 1)

NCBI BLAST Matches:

| Description | Max Score | Total Score | Query Cover | E Value | Max Ident | Accession |
|---|---|---|---|---|---|---|
| *Fusarium verticillioides* voucher UOA/HCPF 14862 18S ribosomal RNA gene, partial sequence; internal transcribed spacer 1, 5.8S ribosomal RNA gene, and internal transcribed spacer 2, complete sequence; and 28S ribosomal RNA gene, partial sequence | 887 | 887 | 100% | 0.0 | 100% | KC709665.1 |
| Fungal sp. AM2013 strain 186_Jm internal transcribed spacer 1, partial sequence; 5.8S ribosomal RNA gene and internal transcribed spacer 2, complete sequence; and 28S ribosomal RNA gene, partial sequence | 887 | 887 | 100% | 0.0 | 100% | KC506334.1 |
| *Fusarium subglutinans* strain HI 18S ribosomal RNA gene, partial sequence; internal transcribed spacer 1, 5.8S ribosomal RNA gene, and internal transcribed spacer 2, complete sequence; and 28S ribosomal RNA gene, partial sequence | 887 | 887 | 100% | 0.0 | 100% | JX960431.1 |
| *Fusarium sacchari* internal transcribed spacer 1, partial sequence; 5.8S ribosomal RNA gene and internal transcribed spacer 2, complete sequence; and 28S ribosomal RNA gene, partial sequence | 887 | 887 | 100% | 0.0 | 100% | JN997445.1 |
| *Fusarium* sp. PRE4b 18S ribosomal RNA gene, partial sequence; internal transcribed spacer 1, 5.8S ribosomal RNA gene, and internal transcribed spacer 2, complete sequence; and 28S ribosomal RNA gene, partial sequence >gbiKC254039.1I *Gibberella intermedia* culture-collection UOA/HCPF<GRC>: 12610 18S ribosomal | 887 | 887 | 100% | 0.0 | 100% | JN254793.1 |

TABLE 2-continued

| Description | Max Score | Total Score | Query Cover | E Value | Max Ident | Accession |
|---|---|---|---|---|---|---|
| RNA gene, partial sequence; internal transcribed spacer 1, 5.8S ribosomal RNA gene, and internal transcribed spacer 2, complete sequence; and 28S ribosomal RNA gene, partial sequence | | | | | | |
| *Gibberella moniliformis* isolate FM2 18S ribosomal RNA gene, partial sequence; internal transcribed spacer 1, 5.8S ribosomal RNA gene, and internal transcribed spacer 2, complete sequence; and 28S ribosomal RNA gene, partial sequence | 887 | 887 | 100% | 0.0 | 100% | JF499676.1 |
| *Gibberella moniliformis* genes for 18S rRNA, ITS1, 5.8S rRNA, ITS2, 28S rRNA, partial and complete sequence, strain: MAFF 240085 | 887 | 887 | 100% | 0.0 | 100% | AB587012.1 |
| *Gibberella moniliformis* genes for 18S rRNA, ITS1, 5.8S rRNA, ITS2, 28S rRNA, partial and complete sequence, strain: CBS 576.78 | 887 | 887 | 100% | 0.0 | 100% | AB587010.1 |
| *Fusarium subglutinans* genes for 18S rRNA, ITS1, 5.8S rRNA, ITS2, 28S rRNA, partial and complete sequence, strain: ATCC 38016 | 887 | 887 | 100% | 0.0 | 100% |

TABLE 2-continued ribosomal RNA gene, and internal
transcribed spacer 2, complete sequence;
and 28S ribosomal RNA gene, partial
sequence

| | | | | | | |
|---|---|---|---|---|---|---|
| Fusarium sacchari internal transcribed spacer 1, partial sequence; 5.8S ribosomal RNA gene and internal transcribed spacer 2, complete sequence; and 28S ribosomal RNA gene, partial sequence | 883 | 883 | 100% | 0.0 | 100% | JN997445.1 |
| Gibberella moniliformis isolate FM11 internal transcribed spacer 1, partial sequence; 5.8S ribosomal RNA gene and internal transcribed spacer 2, complete sequence; and 28S ribosomal RNA gene, partial sequence | 883 | 883 | 100% | 0.0 | 100% | HQ995666.1 |
| Fusarium sp. PRE4b 18S ribosomal RNA gene, partial sequence; internal transcribed spacer 1, 5.8S ribosomal RNA gene, and internal transcribed spacer 2, complete sequence; and 28S ribosomal RNA gene, partial sequence >gbiKC254039.1I Gibberella intermedia culture-collection UOA/HCPF<GRC>: 12610 18S ribosomal RNA gene, partial sequence; internal transcribed spacer 1, 5.8S ribosomal RNA gene, and internal transcribed spacer 2, complete sequence; and 28S ribosomal RNA gene, partial sequence | 883 | 883 | 100% | 0.0 | 100% | JN254793.1 |
| Gibberella moniliformis isolate FM2 18S ribosomal RNA gene, partial sequence; internal transcribed spacer 1, 5.8S ribosomal RNA gene, and internal transcribed spacer 2, complete sequence; and 28S ribosomal RNA gene, partial sequence | 883 | 883 | 100% | 0.0 | 100% | JF499676.1 |
| Gibberella moniliformis genes for 18S rRNA, ITS1, 5.8S rRNA, ITS2, 28S rRNA, partial and complete sequence, strain: MAFF 240085 | 883 | 883 | 100% | 0.0 | 100% | AB587012.1 |
| Gibberella moniliformis genes for 18S rRNA, ITS1, 5.8S rRNA, ITS2, 28S rRNA, partial and complete sequence, strain: CBS 576.78 | 883 | 883 | 100% | 0.0 | 100% | AB587010.1 |

E 4-5 Fusarium sp.

Sequence (488 bases):
CTTAATGTTGCCTCGGCGGATCAGCCCGCGCCCCGTAAAACGGGACGGCCCGCCAG
AGGACCCAAACTCTAATGTTTCTTATTGTAACTTCTGAGTAAAACAAACAAATAAAT
CAAAACTTTCAACAACGGATCTCTTGGTTCTGGCATCGATGAAGAACGCAGCAAAT
GCGATAAGTAATGTGAATTGCAGAATTCAGTGAATCATCGAATCTTTGAACGCACAT
TGCGCCCGCTGGTATTCCGGCGGGCATGCCTGTTCGAGCGTCATTTCAACCCTCAAG
CCCCCGGGTTTGGTGTTGGGGATCGGCTCTGCCTTCTGGCGGTGCCGCCCCGAAAT
ACATTGGCGGTCTCGCTGCAGCCTCCATTGCGTAGTAGCTAACACCTCGCAACTGGA
ACGCGGCGCGGCCATGCCGTAAAACCCCAACTTCTGAATGTTGACCTCGGATCAGGT
AGGAATACCCGCTGAACTTAAGCATATCAATAG (SEQ ID NO: 3)

NCBI BLAST Matches:

| Description | Max Score | Total Score | Query Cover | E Value | Max Ident | Accession |
|---|---|---|---|---|---|---|
| Uncultured Fusarium clone R1_12 18S ribosomal RNA gene, partial sequence; internal transcribed spacer 1, 5.8S ribosomal RNA gene, and internal transcribed spacer 2, complete sequence; and 28S ribosomal RNA gene, partial sequence | 900 | 900 | 99% | 0.0 | 100% | KC753424.1 |
| Uncultured Fusarium genomic DNA containing 18S rRNA gene, ITS1, 5.8S rRNA gene, ITS2 and 28S rRNA gene, clone RRA10 | 900 | 900 | 99% | 0.0 | 100% | HE977525.1 |

TABLE 2-continued

| | | | | | | |
|---|---|---|---|---|---|---|
| *Fusarium tricinctum* isolate XSCZ07 internal transcribed spacer 1, partial sequence; 5.8S ribosomal RNA gene and internal transcribed spacer 2, complete sequence; and 28S ribosomal RNA gene, partial sequence | 900 | 900 | 99% | 0.0 | 100% | JQ676180.1 |
| Uncultured fungus clone Hyp12 internal transcribed spacer 1, partial sequence; 5.8S ribosomal RNA gene and internal transcribed spacer 2, complete sequence; and 28S ribosomal RNA gene, partial sequence | 900 | 900 | 99% | 0.0 | 100% | JQ618507.1 |
| *Fusarium tricinctum* isolate UASWS0796 18S ribosomal RNA gene, internal transcribed spacer 1, 5.8S ribosomal RNA gene, internal transcribed spacer 2, and 28S ribosomal RNA gene, region | 900 | 900 | 99% | 0.0 | 100% | JN662408.1 |
| *Fusarium* sp. NRRL 52933 internal transcribed spacer I, 5.8S ribosomal RNA gene, and internal transcribed spacer 2, complete sequence; and 28S ribosomal RNA gene, partial sequence | 900 | 900 | 99% | 0.0 | I00% | JF740937.I |
| *Fusarium* sp. NRRL 52714 internal transcribed spacer I, 5.8S ribosomal RNA gene, and internal transcribed spacer 2, complete sequence; and 28S ribosomal RNA gene, partial sequence | 900 | 900 | 99% | 0.0 | I00% | JF740911.I |
| *Fusarium* sp. NRRL 25129 internal transcribed spacer I, 5.8S ribosomal RNA gene, and internal transcribed spacer 2, complete sequence; and 28S ribosomal RNA gene, partial sequence >gbiJF740916.II *Fusarium* sp. NRRL 52726 internal transcribed spacer I, 5.8S ribosomal RNA gene, and internal transcribed spacer 2, complete sequence; and 28S ribosomal RNA gene, partial sequence >gb IJF740917.II *Fusarium* sp. NRRL 52727 internal transcribed spacer I, 5.8S ribosomal RNA gene, and internal transcribed spacer 2, complete sequence; and 28S ribosomal RNA gene, partial sequence >gb IJF740918.II *Fusarium* sp. NRRL 52730 internal transcribed spacer I, 5.8S ribosomal RNA gene, and internal transcribed spacer 2, complete sequence; and 28S ribosomal RNA gene, partial sequence | 900 | 900 | 99% | 0.0 | I00% | JF740895.I |
| *Fusarium* sp. NRRL 25128 internal transcribed spacer I, 5.8S ribosomal RNA gene, and internal transcribed spacer 2, complete sequence; and 28S ribosomal RNA gene, partial sequence | 900 | 900 | 99% | 0.0 | I00% | JF740894.I |
| *Gibberella avenacea* isolate 3214 18S ribosomal RNA gene, partial sequence; internal transcribed spacer I, 5.8S ribosomal RNA gene, and internal transcribed spacer 2, complete sequence; and 28S ribosomal RNA gene, partial sequence | 900 | 900 | 99% | 0.0 | I00% | FJ224099.I |

PC-2-24 (Control) *Fusarium culmorum*

Sequence (477 bases):
CATACCTTATGTTGCCTCGGCGGATCAGCCCCGCGCCCCGTAAAAAGGGACGGCCCG
CCGCAGGAACCCTAAACTCTGTTTTTAGTGGAACTTCTGAGTATAAAAAACAAATAA
ATCAAAACTTTCAACAACGGATCTCTTGGTTCTGGCATCGATGAAGAACGCAGCAAA
ATGCGATAAGTAATGTGAATTGCAGAATTCAGTGAATCATCGAATCTTTGAACGCAC
ATTGCGCCCGCCAGTATTCTGGCGGGCATGCCTGTTCGAGCGTCATTTCAACCCTCA
AGCCCAGCTTGGTGTTGGGAGCTGCAGTCCTGCTGCACTCCCCAAATACATTGGCGG
TCACGTCGAGCTTCCATAGCGTAGTAATTTACATATCGTTACTGGTAATCGTCGCGG

TABLE 2-continued

CCACGCCGTTAAACCCCAACTTCTGAATGTTGACCTCGGATCAGGTAGGAATACCCG
CTGAACTTAAGCATATCAATAG (SEQ ID NO: 4)

NCBI BLAST Matches:

| Description | Max Score | Total Score | Query Cover | E Value | Max Ident | Accession |
|---|---|---|---|---|---|---|
| *Fusarium* sp. OTU930 internal transcribed spacer 1, partial sequence; 5.8S ribosomal RNA gene and internal transcribed spacer 2, complete sequence; and 28S ribosomal RNA gene, partial sequence | 881 | 990 | 100% | 0.0 | 100% | GU934527.1 |
| *Fusarium culmorum* isolate 149 18S ribosomal RNA gene, partial sequence; internal transcribed spacer 1, 5.8S ribosomal RNA gene, and internal transcribed spacer 2, complete sequence; and 28S ribosomal RNA gene, partial sequence | 880 | 880 | 99% | 0.0 | 100% | KC989094.1 |
| *Fusarium cerealis* genes for contains 18S rRNA, ITS1, 5.8S rRNA, ITS2, 28S rRNA, partial and complete sequence, strain: MAFF 101144 | 880 | 880 | 99% | 0.0 | 100% | AB820718.1 |
| *Fusarium culmorum* genes for 18S rRNA, ITS1, 5.8S rRNA, ITS2, 28S rRNA, partial and complete sequence, strain: MAFF 241212 >dbj\|AB820717.1\| *Fusarium cerealis* genes for contains 18S rRNA, ITS1, 5.8S rRNA, ITS2, 28S rRNA, partial and complete sequence, strain: MAFF 241212 | 880 | 880 | 99% | 0.0 | 100% | AB586990.1 |
| *Fusarium cerealis* strain FC3 18S ribosomal RNA gene, internal transcribed spacer 1, 5.8S ribosomal RNA gene, internal transcribed spacer 2, and 28S ribosomal RNA gene, region | 880 | 880 | 99% | 0.0 | 100% | JF303876.1 |
| *Fusarium cerealis* strain FC2 18S ribosomal RNA gene, internal transcribed spacer 1, 5.8S ribosomal RNA gene, internal transcribed spacer 2, and 28S ribosomal RNA gene, region | 880 | 880 | 99% | 0.0 | 100% | JF303871.1 |
| *Fusarium cerealis* strain FC1 18S ribosomal RNA gene, internal transcribed spacer 1, 5.8S ribosomal RNA gene, internal transcribed spacer 2, and 28S ribosomal RNA gene, region | 880 | 880 | 99% | 0.0 | 100% | JF303867.1 |
| *Fusarium culmorum* strain G5 18S ribosomal RNA gene, partial sequence; internal transcribed spacer 1, 5.8S ribosomal RNA gene, and internal transcribed spacer 2, complete sequence; and 28S ribosomal RNA gene, partial sequence | 880 | 880 | 99% | 0.0 | 100% | GU566271.1 |
| Uncultured Hypocreales clone B2_i_ITS IF internal transcribed spacer 1, partial sequence; 5.8S ribosomal RNA gene, complete sequence; and internal transcribed spacer 2, partial sequence | 880 | 880 | 99% | 0.0 | 100% | EU754930.1 |
| Uncultured Hypocreales clone B3_I_c_ITS IF internal transcribed spacer 1, partial sequence; 5.8S ribosomal RNA gene, complete sequence; and internal transcribed spacer 2, partial sequence | 880 | 880 | 99% | 0.0 | 100% | EU754928.1 |

E 30-14 *Fusarium avenaceum*

Sequence (485 bases):
CAGAAGTTGGGGTTTTACGGCATGGCCGCGCCGCGTTCCAGTTGCGAGGTGTTAGCT
ACTACGCAATGGAGGCTGCAGCGAGACCGCCAATGTATTTCGGGGGCGGCACCGCC
AGAAGGCAGAGCCGATCCCCAACACCAAACCCGGGGCTTGAGGGTTGAAATGACG
CTCGAACAGGCATGCCCGCCGGAATACCAGCGGGCGCAATGTGCGTTCAAAGATTC TABLE 2-continued

```
GATGATTCACTGAATTCTGCAATTCACATTACTTATCGCATTTTGCTGCGTTCTTCAT
CGATGCCAGAACCAAGAGATCCGTTGTTGAAAGTTTTGATTTATTTGTTTGTTTTACT
CAGAAGTTACAATAAGAAACATTAGAGTTTGGGTCCTCTGGCGGGCCGTCCCGTTTT
ACGGGGCGCGGGCTGATCCGCCGAGGCAACATTAAGGTATGTTCACAGGGGTTTGG
GAGTTGTAAACTCGGTAATGATCCCTCCGCA (SEQ ID NO: 5)
```

NCBI BLAST Matches:

| Description | Max Score | Total Score | Query Cover | E Value | Max Ident | Accession |
|---|---|---|---|---|---|---|
| *Fusarium avenaceum* 18S ribosomal RNA gene, partial sequence; internal transcribed spacer 1, 5.8S ribosomal RNA gene, and internal transcribed spacer 2, complete sequence; and 28S ribosomal RNA gene, partial sequence >gbiJX402187.1I | 896 | 896 | 100% | 0.0 | 100% | JX402184.1 |
| *Fusarium avenaceum* 18S ribosomal RNA gene, partial sequence; internal transcribed spacer 1, 5.8S ribosomal RNA gene, and internal transcribed spacer 2, complete sequence; and 28S ribosomal RNA gene, partial sequence | 896 | 896 | 100% | 0.0 | 100% | JX402183.1 |
| *Fusarium avenaceum* 18S ribosomal RNA gene, partial sequence; internal transcribed spacer 1, 5.8S ribosomal RNA gene, and internal transcribed spacer 2, complete sequence; and 28S ribosomal RNA gene, partial sequence | 896 | 896 | 100% | 0.0 | 100% | JX402180.1 |
| *Fusarium avenaceum* 18S ribosomal RNA gene, partial sequence; internal transcribed spacer 1, 5.8S ribosomal RNA gene, and internal transcribed spacer 2, complete sequence; and 28S ribosomal RNA gene, partial sequence | 896 | 896 | 100% | 0.0 | 100% | JX402179.1 |
| *Fusarium tricinctum* strain wxm38 18S ribosomal RNA gene, partial sequence; internal transcribed spacer 1, 5.8S ribosomal RNA gene, and internal transcribed spacer 2, complete sequence; and 28S ribosomal RNA gene, partial sequence | 896 | 896 | 100% | 0.0 | 100% | HM037940.1 |
| *Fusarium tricinctum* genes for 18S rRNA, ITS1, 5.8S rRNA, ITS2, 28S rRNA, partial and complete sequence, isolate: TS08-58-2 | 896 | 896 | 100% | 0.0 | 100% | AB470855.1 |
| *Fusarium tricinctum* genes for 18S rRNA, ITS1, 5.8S rRNA, ITS2, 28S rRNA, partial and complete sequence, isolate: TS08-86-1 >dbjiAB470818.1I *Fusarium tricinctum* genes for 18S rRNA, ITS1, 5.8S rRNA, ITS2, 28S rRNA, partial and complete sequence, isolate: TS08-70-1 >gbiGU586834.1I *Fusarium tricinctum* isolate Ppf30 18S ribosomal RNA gene, partial sequence; internal transcribed spacer 1, 5.8S ribosomal RNA gene, and internal transcribed spacer 2, complete sequence; and 28S ribosomal RNA gene, partial sequence | 896 | 896 | 100% | 0.0 | 100% | AB470859.1 |
| *Gibberella avenacea* isolate FA37 18S ribosomal RNA gene, partial sequence; internal transcribed spacer 1, 5.8S ribosomal RNA gene, and internal transcribed spacer 2, complete sequence; and 28S ribosomal RNA gene, partial sequence | 896 | 896 | 100% | 0.0 | 100% | FJ602983.1 |
| *Gibberella avenacea* isolate FA18 18S ribosomal RNA gene, partial sequence; internal transcribed spacer 1, 5.8S ribosomal RNA gene, and internal | 896 | 896 | 100% | 0.0 | 100% | FJ602964.1 |

TABLE 2-continued transcribed spacer 2, complete sequence;
and 28S ribosomal RNA gene, partial
sequence >gbiFJ602975.1I *Gibberella
avenacea* isolate FA29 18S ribosomal
RNA gene, partial sequence; internal
transcribed spacer 1, 5.8S ribosomal RNA
gene, and internal transcribed spacer 2,
complete sequence; and 28S ribosomal
RNA gene, partial sequence
>gbiFJ603000.1I *Gibberella avenacea*
isolate FA54 18S ribosomal RNA gene,
partial sequence; internal transcribed
spacer 1, 5.8S ribosomal RNA gene, and
internal transcribed spacer 2, complete
sequence; and 28S ribosomal RNA gene,
partial sequence

| Description | Max Score | Total Score | Query Cover | E Value | Max Ident | Accession |
|---|---|---|---|---|---|---|
| *Gibberella avenacea* isolate FA17 18S ribosomal RNA gene, partial sequence; internal transcribed spacer 1, 5.8S ribosomal RNA gene, and internal transcribed spacer 2, complete sequence; and 28S ribosomal RNA gene, partial sequence >gbiFJ602968.1l *Gibberella avenacea* isolate FA22 18S ribosomal RNA gene, partial sequence; internal transcribed spacer 1, 5.8S ribosomal RNA gene, and internal transcribed spacer 2, complete sequence; and 28S ribosomal RNA gene, partial sequence >gbiFJ602973.\|\| *Gibberella avenacea* isolate FA27 18S ribosomal RNA gene, partial sequence; internal transcribed spacer 1, 5.8S ribosomal RNA gene, and internal transcribed spacer 2, complete sequence; and 28S ribosomal RNA gene, partial sequence >gbiFJ602981.1l *Gibberella avenacea* isolate FA35 18S ribosomal RNA gene, partial sequence; internal transcribed spacer 1, 5.8S ribosomal RNA gene, and internal transcribed spacer 2, complete sequence; and 28S ribosomal RNA gene, partial sequence >gbiFJ602999.1l *Gibberella avenacea* isolate FA53 18S ribosomal RNA gene, partial sequence; internal transcribed spacer 1, 5.8S ribosomal RNA gene, and internal transcribed spacer 2, complete sequence; and 28S ribosomal RNA gene, partial sequence | 896 | 896 | 100% | 0.0 | 100% | FJ602963.1 |

E 06-7 *Fusarium subglutinans*

Sequence (469 bases):
CAGAAGTTGGGGTTTAACGGCGTGGCCGCGACGATTACCAGTAACGAGGGTTTTACT
ACTACGCTATGGAAGCTCGACGTGACCGCCAATCAATTTGGGGAACGCGATTTGACT
CGCGAGTCCCAACACCAAGCTGGGCTTGAGGGTTGAAATGACGCTCGAACAGGCAT
GCCCGCCAGAATACTGGCGGGCGCAATGTGCGTTCAAAGATTCGATGATTCACTGA
ATTCTGCAATTCACATTACTTATCGCATTTTGCTGCGTTCTTCATCGATGCCAGAACC
AAGAGATCCGTTGTTGAAAGTTTTGATTTATTTATGGTTTTACTCAGAAGTTACATAT
AGAAACAGAGTTTAGGGGTCCTCTGGCGGGCCGTCCCGTTTTACCGGGAGCGGGCT
GATCCGCCGAGGCAACAATTGGTATGTTCACAGGGGTTTGGGAGTTGTAAACTCGGT
AATGATCCCTCCGC (SEQ ID NO: 6)

NCBI BLAST Matches:

| Description | Max Score | Total Score | Query Cover | E Value | Max Ident | Accession |
|---|---|---|---|---|---|---|
| *Fusarium verticillioides* voucher UOA/HCPF 14862 18S ribosomal RNA gene, partial sequence; internal transcribed spacer 1, 5.8S ribosomal RNA gene, and internal transcribed spacer 2, complete sequence; and 28S ribosomal RNA gene, partial sequence | 867 | 867 | 100% | 0.0 | 100% | KC709665.1 |
| *Fusarium subglutinans* strain AAFC-Fcir-012 18S ribosomal RNA gene, | 867 | 867 | 100% | 0.0 | 100% | KC464632.1 |

TABLE 2-continued

| | | | | | | |
|---|---|---|---|---|---|---|
| partial sequence; internal transcribed spacer 1, 5.8S ribosomal RNA gene, and internal transcribed spacer 2, complete sequence; and 28S ribosomal RNA gene, partial sequence | | | | | | |
| *Gibberella moniliformis* genomic DNA containing 18S rRNA gene, ITS1, 5.8S rRNA gene, ITS2 and 28S rRNA gene, strain DBT-112 | 867 | 1017 | 100% | 0.0 | 100% | HF570008.1 |
| *Gibberella moniliformis* isolate SIDV20110221051 18S ribosomal RNA gene, partial sequence; internal transcribed spacer 1, 5.8S ribosomal RNA gene, and internal transcribed spacer 2, complete sequence; and 28S ribosomal RNA gene, partial sequence | 867 | 867 | 100% | 0.0 | 100% | KC143121.1 |
| *Gibberella intermedia* voucher LFG4-3BBRS internal transcribed spacer 1, 5.8S ribosomal RNA gene, and internal transcribed spacer 2-like gene, partial sequence; mitochondrial | 867 | 867 | 100% | 0.0 | 100% | JQ272470.1 |
| *Gibberella moniliformis* strain CB 1 18S ribosomal RNA gene, partial sequence; internal transcribed spacer 1, 5.8S ribosomal RNA gene, and internal transcribed spacer 2, complete sequence; and 28S ribosomal RNA gene, partial sequence | 867 | 867 | 100% | 0.0 | 100% | JX511973.1 |
| *Fusarium* sp. CHTAG40 18S ribosomal RNA gene, partial sequence; internal transcribed spacer 1, 5.8S ribosomal RNA gene, and internal transcribed spacer 2, complete sequence; and 28S ribosomal RNA gene, partial sequence | 867 | 867 | 100% | 0.0 | 100% | JF773630.1 |
| *Fusarium* sp. CHTAG38 18S ribosomal RNA gene, partial sequence; internal transcribed spacer 1, 5.8S ribosomal RNA gene, and internal transcribed spacer 2, complete sequence; and 28S ribosomal RNA gene, partial sequence | 867 | 867 | 100% | 0.0 | 100% | JF773629.1 |
| *Fusarium* sp. CHTAG34 18S ribosomal RNA gene, partial sequence; internal transcribed spacer 1, 5.8S ribosomal RNA gene, and internal transcribed spacer 2, complete sequence; and 28S ribosomal RNA gene, partial sequence | 867 | 867 | 100% | 0.0 | 100% | JF773628.1 |
| *Fusarium* sp. CHTAG32 18S ribosomal RNA gene, partial sequence; internal transcribed spacer 1, 5.8S ribosomal RNA gene, and internal transcribed spacer 2, complete sequence; and 28S ribosomal RNA gene, partial sequence | 867 | 867 | 100% | 0.0 | 100% | JF773627.1 |

E-30-7 *Fusarium avenaceum*

Sequence (480 bases):
GAAGTTGGGGTTTTACGGCATGGCCGCGCCGCGTTCCAGTTGCGAGGTGTTAGCTAC
TACGCAATGGAGGCTGCAGCGAGACCGCCAATGTATTTCGGGGCGGCACCGCCAG
AAGGCAGAGCCGATCCCCAACACCAAACCCGGGGGCTTGAGGGTTGAAATGACGCT
CGAACAGGCATGCCCGCCGGAATACCAGCGGGCGCAATGTGCGTTCAAAGATTCGA
TGATTCACTGAATTCTGCAATTCACATTACTTATCGCATTTTGCTGCGTTCTTCATCG

TABLE 2-continued

ATGCCAGAACCAAGAGATCCGTTGTTGAAAGTTTTGATTTATTTGTTTGTTTTACTCA
GAAGTTACAATAAGAAACATTAGAGTTTGGGTCCTCTGGCGGGCCGTCCCGTTTTAC
GGGGCGCGGGCTGATCCGCCGAGGCAACATTAAGGTATGTTCACAGGGGTTTGGGA
GTTGTAAACTCGGTAATGATCCCTCC (SEQ ID NO: 7)

NCBI BLAST Matches:

| Description | Max Score | Total Score | Query Cover | E Value | Max Ident | Accession |
|---|---|---|---|---|---|---|
| *Fusarium avenaceum* isolate 143 18S ribosomal RNA gene, partial sequence; internal transcribed spacer 1, 5.8S ribosomal RNA gene, and internal transcribed spacer 2, complete sequence; and 28S ribosomal RNA gene, partial sequence | 887 | 887 | 100% | 0.0 | 100% | KC989099.1 |
| Uncultured *Fusarium* clone R1_12 18S ribosomal RNA gene, partial sequence; internal transcribed spacer 1, 5.8S ribosomal RNA gene, and internal transcribed spacer 2, complete sequence; and 28S ribosomal RNA gene, partial sequence | 887 | 887 | 100% | 0.0 | 100% | KC753424.1 |
| *Fusarium avenaceum* strain Fk15 small subunit ribosomal RNA gene, partial sequence; internal transcribed spacer 1, 5.8S ribosomal RNA gene, and internal transcribed spacer 2, complete sequence; and large subunit ribosomal RNA gene, partial sequence | 887 | 887 | 100% | 0.0 | 100% | KC464345.1 |
| *Fusarium avenaceum* 18S ribosomal RNA gene, partial sequence; internal transcribed spacer 1, 5.8S ribosomal RNA gene, and internal transcribed spacer 2, complete sequence; and 28S ribosomal RNA gene, partial sequence >gbiJX402187.1I *Fusarium avenaceum* 18S ribosomal RNA gene, partial sequence; internal transcribed spacer 1, 5.8S ribosomal RNA gene, and internal transcribed spacer 2, complete sequence; and 28S ribosomal RNA gene, partial sequence >gbiJX402188.1I *Fusarium avenaceum* 18S ribosomal RNA gene, partial sequence; internal transcribed spacer 1, 5.8S ribosomal RNA gene, and internal transcribed spacer 2, complete sequence; and 28S ribosomal RNA gene, partial sequence >gbiJX402189.1I *Fusarium avenaceum* 18S ribosomal RNA gene, partial sequence; internal transcribed spacer 1, 5.8S ribosomal RNA gene, and internal transcribed spacer 2, complete sequence; and 28S ribosomal RNA gene, partial sequence >gbiJX402190.1I *Fusarium avenaceum* 18S ribosomal RNA gene, partial sequence; internal transcribed spacer 1, 5.8S ribosomal RNA gene, and internal transcribed spacer 2, complete sequence; and 28S ribosomal RNA gene, partial sequence | 887 | 887 | 100% | 0.0 | 100% | JX402184.1 |
| *Fusarium avenaceum* 18S ribosomal RNA gene, partial sequence; internal transcribed spacer 1, 5.8S ribosomal RNA gene, and internal transcribed spacer 2, complete sequence; and 28S ribosomal RNA gene, partial sequence | 887 | 887 | 100% | 0.0 | 100% | JX402183.1 |

TABLE 2-continued

| Description | Max Score | Total Score | Query Cover | E Value | Max Ident | Accession |
|---|---|---|---|---|---|---|
| *Fusarium avenaceum* 18S ribosomal RNA gene, partial sequence; internal transcribed spacer 1, 5.8S ribosomal RNA gene, and internal transcribed spacer 2, complete sequence; and 28S ribosomal RNA gene, partial sequence | 887 | 887 | 100% | 0.0 | 100% | JX402180.1 |
| *Fusarium avenaceum* 18S ribosomal RNA gene, partial sequence; internal transcribed spacer 1, 5.8S ribosomal RNA gene, and internal transcribed spacer 2, complete sequence; and 28S ribosomal RNA gene, partial sequence | 887 | 887 | 100% | 0.0 | 100% | JX402179.1 |
| Uncultured *Fusarium* genomic DNA containing 18S rRNA gene, ITS1, 5.8S rRNA gene, ITS2 and 28S rRNA gene, clone RRF01 | 887 | 887 | 100% | 0.0 | 100% | HE977545.1 |
| *Fusarium* sp. CHTAM47 18S ribosomal RNA gene, partial sequence; internal transcribed spacer 1, 5.8S ribosomal RNA gene, and internal transcribed spacer 2, complete sequence; and 28S ribosomal RNA gene, partial sequence | 887 | 887 | 100% | 0.0 | 100% | JF773662.1 |
| *Fusarium* sp. CHTAM2 18S ribosomal RNA gene, partial sequence; internal transcribed spacer 1, 5.8S ribosomal RNA gene, and internal transcribed spacer 2, complete sequence; and 28S ribosomal RNA gene, partial sequence | 887 | 887 | 100% | 0.0 | 100% | JF773634.1 |

E 06-01 *Fusarium subglutinans*

Sequence (468 bases):
GAAGTTGGGGTTTAACGGCGTGGCCGCGACGATTACCAGTAACGAGGGTTTTACTAC
TACGCTATGGAAGCTCGACGTGACCGCCAATCAATTTGGGGAACGCGATTTGACTCG
CGAGTCCCAACACCAAGCTGGGCTTGAGGGTTGAAATGACGCTCGAACAGGCATGC
CCGCCAGAATACTGGCGGGCGCAATGTGCGTTCAAAGATTCGATGATTCACTGAATT
CTGCAATTCACATTACTTATCGCATTTTGCTGCGTTCTTCATCGATGCCAGAACCAAG
AGATCCGTTGTTGAAAGTTTTGATTTATTTATGGTTTTACTCAGAAGTTACATATAGA
AACAGAGTTTAGGGGTCCTCTGGCGGGCCGTCCCGTTTTACCGGGAGCGGGCTGATC
CGCCGAGGCAACAATTGGTATGTTCACAGGGGTTTGGGAGTTGTAAACTCGGTAATG
ATCCCTCCGCA (SEQ ID NO: 8)

NCBI BLAST Matches:

| Description | Max Score | Total Score | Query Cover | E Value | Max Ident | Accession |
|---|---|---|---|---|---|---|
| *Fusarium verticillioides* voucher UOA/HCPF 14862 18S ribosomal RNA gene, partial sequence; internal transcribed spacer 1, 5.8S ribosomal RNA gene, and internal transcribed spacer 2, complete sequence; and 28S ribosomal RNA gene, partial sequence | 865 | 865 | 100% | 0.0 | 100% | KC709665.1 |
| *Gibberella moniliformis* genomic DNA containing 18S rRNA gene, ITS1, 5.8S rRNA gene, ITS2 and 28S rRNA gene, strain DBT-112 | 865 | 1016 | 100% | 0.0 | 100% | HF570008.1 |
| *Gibberella moniliformis* isolate SIDV20110221051 18S ribosomal RNA gene, partial sequence; internal transcribed spacer 1, 5.8S ribosomal RNA gene, and internal transcribed spacer 2, complete sequence; and 28S ribosomal RNA gene, partial sequence | 865 | 865 | 100% | 0.0 | 100% | KC143121.1 |

TABLE 2-continued

| Description | | | | | | |
|---|---|---|---|---|---|---|
| *Gibberella moniliformis* strain CB1 18S ribosomal RNA gene, partial sequence; internal transcribed spacer 1, 5.8S ribosomal RNA gene, and internal transcribed spacer 2, complete sequence; and 28S ribosomal RNA gene, partial sequence | 865 | 865 | 100% | 0.0 | 100% | JX511973.1 |
| *Gibberella moniliformis* isolate FM13 18S ribosomal RNA gene, partial sequence; internal transcribed spacer 1, 5.8S ribosomal RNA gene, and internal transcribed spacer 2, complete sequence; and 28S ribosomal RNA gene, partial sequence | 865 | 865 | 100% | 0.0 | 100% | HQ995667.1 |
| *Gibberella moniliformis* isolate FM2 18S ribosomal RNA gene, partial sequence; internal transcribed spacer 1, 5.8S ribosomal RNA gene, and internal transcribed spacer 2, complete sequence; and 28S ribosomal RNA gene, partial sequence | 865 | 865 | 100% | 0.0 | 100% | JF499676.1 |
| *Fusarium* sp. Ljf001 18S ribosomal RNA gene, partial sequence; internal transcribed spacer 1, 5.8S ribosomal RNA gene, and internal transcribed spacer 2, complete sequence; and 28S ribosomal RNA gene, partial sequence | 865 | 865 | 100% | 0.0 | 100% | HQ025928.1 |
| *Gibberella* sp. FLS-2010 isolate FS-74(3) 18S ribosomal RNA gene, partial sequence; internal transcribed spacer 1, 5.8S ribosomal RNA gene, and internal transcribed spacer 2, complete sequence; and 28S ribosomal RNA gene, partial sequence >gb1HQ023214.11 *Gibberella* sp. FLS-2010 isolate FS-78(3) 18S ribosomal RNA gene, partial sequence; internal transcribed spacer 1, 5.8S ribosomal RNA gene, and internal transcribed spacer 2, complete sequence; and 28S ribosomal RNA gene, partial sequence >gb1HQ023215.11 *Aspergillus* sp. FLS-2010 isolate FS-55(3) 18S ribosomal RNA gene, partial sequence; internal transcribed spacer 1, 5.8S ribosomal RNA gene, and internal transcribed spacer 2, complete sequence; and 28S ribosomal RNA gene, partial sequence | 865 | 865 | 100% | 0.0 | 100% | HQ023213.1 |
| *Gibberella* sp. FLS-2010 isolate FS-48.5(1) 18S ribosomal RNA gene, partial sequence; internal transcribed spacer 1, 5.8S ribosomal RNA gene, and internal transcribed spacer 2, complete sequence; and 28S ribosomal RNA gene, partial sequence | 865 | 865 | 100% | 0.0 | 100% | HQ023211.1 |
| *Gibberella* sp. FLS-2010 isolate FS-82(3) 18S ribosomal RNA gene, partial sequence; internal transcribed spacer 1, 5.8S ribosomal RNA gene, and internal transcribed spacer 2, complete sequence; and 28S ribosomal RNA gene, partial sequence | 865 | 865 | 100% | 0.0 | 100% | HQ023203.1 |

ITS Based Phylogenetic Analysis

Phylogenetic analysis of these organisms was carried out by the acquisition of the ITS-5.8 S ribosomal gene sequence. The fungus was grown on PDA for 7 days and DNA templates were prepared by using the Prepman Ultra Sample Preparation Reagent (Applied Biosystems, USA) according to the manufacturer's guidelines. The ITS regions of the fungus were amplified with the universal ITS primers ITS1 (5' TCCGTAGGTGAACCTGCGG 3'; SEQ ID NO: 9) and ITS4 (5'TCCTCCGCTTATTGATATGC 3'; SEQ ID NO: 10) using Polymerase Chain Reaction (PCR). The PCR conditions used were as follows: initial denaturation at 94° C. for 3 min followed by 30 cycles of 94° C. for 15 sec., 50° C. for 30 sec., 72° C. for 45 sec., and a final extension at 72° C. for 5 min. The 50 lll reaction mixture contained 1×PCR buffer, 200 each dNTP, 1.5 mM MgCh, 10 pmol of each primer, 1-5 ng of DNA and 2.5 U of Taq DNA polymerase. The amplified product (5 !J.l) was visualized on 1% (w/v) agarose gel to confirm the presence of a single amplified band. The amplified products were purified by Amicon Ultra columns (Millipore, USA) and 20-40 ng were used in a 10 lll sequencing reaction using the Big Dye Terminator sequencing kit (v. 3.1), with 2 pmoles of the forward or the reverse primer in the cycle sequencing reaction. Twenty cycles of 96° C. for 10 s, 50° C. for 5 s and 60° C. for 4 min were performed and the extension products were purified by ethanol precipitation, dissolved in 10 lll of HiDi Formamide, incubated at 95° C. for 1 min and loaded on ABI Prism 377 Genetic Analyzer (Perkin-Elmer, USA) for sequencing. All the reagents for sequencing were from Applied Biosystems, USA The amplified products were sequenced and aligned with the sequences in the GenBank by BLASTN program (Altschul et al., 1997). Sequencing was performed at the U Calif, Berkeley.

Shown in Table 3 is the growth of various fusaria on human wastes causes a reduction of the dry weight of the mass during the course of a 7 week experiment. The experimental set-up contained 0.5 g of bentonite with System 2 on a water agar plate having about 100 mg wet weight of human waste and a small agar plug with the test *fusarium* on it. The incubation period was 7 weeks at 22° C. The remains of the human waste were physically removed and dried for 4 hr at 80° C. and then weighed.

TABLE 3

| *Fusarium* isolate designation | Dry weight of the human waste remaining after 7 weeks. mg. |
|---|---|
| Control - no *fusarium* | 43 |
| EC-4-5 | 14 |
| E06-7 | 23 |
| E 06-7 | 25 |
| P2-24 *Fusarium culmorum* Original control | 24 |
| E30-2 | 18 |
| E 30-7 | 27 |
| E 06-1 | 16 |
| E 30-14 | 15 |
| E06-8 | 14 |

Example 2

Establishment of S-3 and S-4 Mixes

Tests were conducted as similarly described for Systems 1 and 2 above (FIG. 9) to ascertain the biological activities of various test mixtures against a panel of test microbes. A small plug of each organism was placed in the periphery of the PDA plate. In the center well was placed the test solution in the plastic cup holder. A control plate (A) was also set up. After 30 hr the growth of the test organisms was compared to that of the control and the % inhibition was calculated. The (B) plate contained the test mixture. Measurements were made 30 hr after plate set up.

It is to be noted that the System 1 and 2 mixtures described herein contain about 3.5 parts of propanoic acid along with 3.5 parts of isobutryic acid and finally two parts of an ester—either isoamyl butryate (System 1) or isoamyl isobutryate (System 2). It is realized that while these mixtures are effective in a number of applications there may be other mixtures that are even more effective by virtue of their range of biological activities, their utility and their effectiveness at low doses. To this end, a search was conducted using the standard propanoic acid as a starting point whilst omitting isobutryic acid (because of its offensive odor) and now including larger molecular weight esters as the ester component. Quite surprisingly and unexpectedly, it was discovered that the use of propanoic acid (7) parts and Isoamyl Hexonates (2) parts produced a volatile mixture with biological activities that exceeded that of either B-23 (see below), and S-1 as shown in Table 4. This new mixture is designated as System 3, while the formulation comprising propanoic acid (7) and formate (2) is designated System 4. It is to be noted that System 4 is less active against most of the test organisms than System 3, but System 4 does kill *E coli* while allowing for the growth of *Fusarium*. To this end, System 4 is an effective mixture to be used as a human waste treatment along with *Fusarium* spp.

TABLE 4

The effects of various esters and propanoic acid on the growth of test organisms measured at 30 hr at room temperature. The effect is represented as percent inhibition of the growth when directly compared to the growth of an uninoculated control. Measurements (average of two) were made as the hyphal growth from the edge of the inoculum plug.

| | *Cercospora beticola* | *Phytophthora cinnamomi* | *Verticillium dahliae* | *Sclerotinia sclerotiorum* | *Pythium ultimum* |
|---|---|---|---|---|---|
| S-1 Solution | 100 | 72 | 92 | 0 | 100 |
| B-23** | 92 | 89 | 42 | 66 | 100 |
| Isoamyl Hexonates (2-tl) | 83 | 13 | 0 | 66 | 28 |
| Propanoic Acid | 66 | 38 | 83 | 0 | 100 |
| Propanoic Acid with Isoamyl Formate (7:2) = S-4 | 100 | 72 | 100 | 0 | 100 |

TABLE 4-continued The effects of various esters and propanoic acid on the growth of test organisms measured at 30 hr at room temperature. The effect is represented as percent inhibition of the growth when directly compared to the growth of an uninoculated control. Measurements (average of two) were made as the hyphal growth from the edge of the inoculum plug.

| | | | | | |
|---|---|---|---|---|---|
| Propanoic Acid with Isobutyl Formate (7:2) | 100 | 79 | 98 | 0 | 100 |
| Propanoic Acid with Isoamyl Hexonates (7:2) = S-3* | 100 | 100 | 100 | 100 | 100 |
| Propanoic Acid with Isoamyl Formate & Cineole (7:1:1) | 100 | 92 | 100 | 94 | 100 |
| Propanoic Acid with equal mix of formates & valencene (7:2:0.5) | 95 | 89 | 100 | 50 | 100 |
| Propanoic Acid with equal mix of formates (7:2) | 98 | 92 | 100 | 64 | 100 |
| Propanoic Acid with Hexyl Formate (7:2:) | 100 | 88 | 87 | 60 | 100 |

| | Fusarium solani | Trichoderma viridae | Rhizoctonia solani | Aspergillus flavus |
|---|---|---|---|---|
| S-1 Solution | 72 | 56 | 100 | 86 |
| B-23** | 32 | 32 | 81 | 29 |
| Isoamyl Hexonates (2 Ill) | 83 | 13 | 0 | 66 |
| Propanoic Acid | 17 | 45 | 81 | 52 |
| Propanoic Acid with Isoamyl Formate (7:2) = S-4 | 53 | 25 | 85 | 0 |
| Propanoic Acid with Isobutyl Formate (7:2) | 0 | 32 | 47 | 29 |
| Propanoic Acid with Isoamyl Hexonates (7:2) = S-3* | 95 | 58 | 100 | 83 |
| Propanoic Acid with Isoamyl Formate & Cineole (7:1:1) | 69 | 35 | 74 | 0 |
| Propanoic Acid with equal mix of formates & valencene (7:2:0.5) | 74 | 35 | 77 | 43 |
| Propanoic Acid with equal mix of formates (7:2) | 58 | 30 | 77 | 29 |
| Propanoic Acid with Hexyl Formate (7:2:) | 86 | 49 | 93 | 90 |

| | Candida albicans | Escherichia coli | Bacillus subtilus | Saccharomyces cerevlceae |
|---|---|---|---|---|
| S-1 Solution | Some growth | No | No | Yes |
| B-23** | Yes | No | No | Medium |
| Isoamyl Hexonates (2 Ill) | Yes | Yes | Yes | Yes |
| Propanoic Acid | Medium | No | No | Yes |
| Propanoic Acid with Isoamyl Formate (7:2) S-4 | Medium | No | No | Yes |
| Propanoic Acid with Isobutyl Formate (7:2) | Yes | No | No | Yes |
| Propanoic Acid with Isoamyl Hexonates (7:2) S-3* | Trace | No | No | Yes |
| Propanoic Acid with Isoamyl Formate & Cineole (7:1:1) | No | No | No | Yes |

TABLE 4-continued

The effects of various esters and propanoic acid on the growth of test organisms measured at 30 hr at room temperature. The effect is represented as percent inhibition of the growth when directly compared to the growth of an uninoculated control. Measurements (average of two) were made as the hyphal growth from the edge of the inoculum plug.

| | | | | |
|---|---|---|---|---|
| Propanoic Acid with equal mix of formates & valencene (7:2:0.5) | Yes | Medium | No | Medium |
| Propanoic Acid with equal mix of formates (7:2) | Yes | No | No | Medium |
| Propanoic Acid with Hexyl Formate (7:2:) | Yes | No | No | Medium |

Activity against yeasts and bacteria
Yes = Growth
Medium = Some Growth
No = No Growth
*S-3 tests were run for 30 hr at room temp and then measured and photographed. Measurements made from edge of inoculation block to edge of colony. Two measurements made and then averaged. The tests were run at room temp. The results show that S-3 was the most biological active mixture of the solutions tested. Also Note S3 - Inhibiting *Erwinia carotovora*: 80-90% and inhibiting *Lactobacillus* sp. ca. 50%.
**B-23 formula tested is as follows: 1.39 parts acetaldehyde; 2.83 parts 2-butanone; 30.56 parts propanoic acid, 2-methyl-, methyl ester; 2.29 parts acetic acid, 2-methylpropyl ester; 1.09 parts propanoic acid, 2-methyl-, 2-methylpropyl ester; 1.78 parts 1-propanol, 2-methyl-; 1.51 parts 2-butenal, 2-methyl-, (E)-; 4.79 parts 1-butanol, 3-methyl-, acetate; 4.78 parts propanoic acid, 2-methyl-, 2-methylbutyl ester; 5.38 parts 1-butanol, 3-methyl-; 351.18 parts propanoic acid, 2-methyl-; 1.31 parts acetic acid, 2-phenylethyl ester.

It is to be noted that the S-3 mixture gave 100% inhibition to many of the organisms tested (Table 4). The effect was greater than with Isoamyl Hexonatess or propanoic acid alone. Thus in some cases it appeared to be strongly synergistic ie. *Sclerotina sclerotiorum* 66% with hexanoates, 0% with propanoic and 100% when the two were combined. Some other organisms also reacted in the same manner such as *Rhizoctonia solani*. In addition it appeared that S-3 was more active than S-1, as well as B-23 and of course the Isoamyl Hexonates or propanoic acid alone (Table 4). Other combinations of propanoic acid and other esters or combinations of esters and terpenoids such as cineole or valencene were not as effective (Table 4). The S-4 formulation, although not as active as S-3, did not cause such a great effect on *Fusarium* but it was inhibitory to other microbes and thus it may be best suited as a useful agent in to treat human wastes in combination with the *Fusarium*. S-3 did kill both bacterial test organisms in the tests (Table 4). S-3 also affected *Erwinia* and *Lactobacillus* sp. (Table 4).

Establishment of the Appropriate Ratios of Ingredients for S-3

The mixes of propanoic acid to Isoamyl Hexonates were varied and subsequently tested according to the procedures outlined above. It turns out that the most favorable mixture was the 7:2 ratio of the two ingredients (Table 5). All others gave lower inhibition values (Table 5). The addition ofterpenoids such as valencene did not promote biological activity. Thus, the ratio of 7:2 v/v of the two ingredients is the most preferred for practical application.

TABLE 5

Effects of various ratios of propanoic acid to Isoamyl Hexonates on a panel of test organisms. All tests were carried out as described in Table 4

| | Cercospora beticola | Phytophthora cinnamomi | Verticillium dahliae | Sclerotinia sclerotiorum | Pythium ultimum |
|---|---|---|---|---|---|
| Propanoic Acid with Isoamyl Hexonates (7:2) = S-3 | 100 | 100 | 100 | 100 | 100 |
| Propanoic Acid with Isoamyl Hexonates (5:4) | 86 | 95 | 100 | 70 | 100 |
| Propanoic Acid with Isoamyl Hexonates (3:6) | 95 | 95 | 94 | 60 | 100 |
| Propanoic Acid with Isoamyl Hexonates & Valencene (6:2:1) | 100 | 95 | 94 | 20 | 100 |

| | Fusarium solani | Trichoderma viridae | Rhizoctonia solani | Aspergillus flavus |
|---|---|---|---|---|
| Propanoic Acid with Isoamyl Hexonates (7:2) | 95 | 58 | 100 | 83 |
| Propanoic Acid with Isoamyl Hexonates (5:4) | 58 | 59 | 89 | 50 |

TABLE 5-continued

Effects of various ratios of propanoic acid to Isoamyl Hexonates on a panel of test organisms. All tests were carried out as described in Table 4

| | | | | |
|---|---|---|---|---|
| Propanoic Acid with Isoamyl Hexonates (3:6) | 72 | 62 | 93 | 50 |
| Propanoic Acid with Isoamyl Hexonates & Valencene (6:2:1) | 72 | 59 | 93 | 50 |

| | Candida albicans | Escherichia coli | Bacillus subtilus | Saccharomyces cereviceae |
|---|---|---|---|---|
| Propanoic Acid with Isoamyl Hexonates (7:2) | Yes | No | No | Some |
| Propanoic Acid with Isoamyl Hexonates (5:4) | Yes | Trace | No | Some |
| Propanoic Acid with Isoamyl Hexonates (3:6) | Yes | Yes | Trace | Some |
| Propanoic Acid with Isoamyl Hexonates & Valencene (6:2:1) | Yes | Some | No | Some |

Yes = Growth
Medium = Some Growth
No = No Growth

C. Testing of Other Esters with Propanoic Acid

As shown in Table 6 below, alternative esters were tested for mixture with propanoic acid at a ratio of 7:2 propanoic acid:ester. These formulations are in addition to formulations S-1, S-2, S-3 and S-4, and accordingly form part of the formulations of the present invention. It should also be appreciated that the present invention may include multiple esters or combinations of any of the esters described hereinthroughout, in conjunction with propanoic acid, preferably at a ratio of 7:2 propanoic acid:ester mixture.

TABLE 6

Testing of Esters

| Test solution | Cercospora beticola | B. Phytophthora Cinnamomi* | C. Verticillium dahliae | D. Sclerotinia sclerotiorum | E. Pythium ultimum |
|---|---|---|---|---|---|
| Propanoic acid with Isoamyl benzoate (7:2) | 96 | — | 100 | 80 | 100 |
| Propanoic acid with Isoamyl phenylacetate (7:2) | 80 | — | 100 | 59 | 100 |
| Propanoic acid with isoamyl cinnamate | 96 | — | 100 | 59 | 100 |
| Propanoic acid with Isoamyl octanoate (7:2) | 96 | — | 100 | 54 | 100 |
| Propanoic acid with Isoamyl salicylate (7:2) | 88 | — | 100 | 49 | 100 |
| Propanoic acid with Isoamyllaurate (7:2) | 72 | — | 100 | 45 | 100 |

| | F. Fusarium solani | G. Trichoderma viridae | H. Rhizoctonia solani | I. Aspergillus flavus |
|---|---|---|---|---|
| Propanoic acid with Isoamyl benzoate (7:2) | 0 | 77 | 74 | 92 |
| Propanoic acid with Isoamyl phenylacetate (7:2) | 0 | 60 | 54 | 92 |
| Propanoic acid with isoamyl cinnamate | 74 | 66 | 64 | 96 |
| Propanoic acid with Isoamyl octanoate (7:2) | 66 | 64 | 62 | 96 |

TABLE 6-continued

| Testing of Esters | | | | | | |
|---|---|---|---|---|---|---|
| Propanoic acid with Isoamyl salicylate (7:2) | | 0 | 64 | 43 | 92 | |
| Propanoic acid with Isoamyl laurate (7:2) | | 0 | 47 | 62 | 20 | |
| Test solution | *C. albicans* | *E. coli* | *Bacillus subtilus* | S. cerev1ceae | *Lactobacillus* | *Envinia carotovora* |
| Propanoic acid with Isoamyl benzoate (7:2) | Trace | No | No | Trace | Medium | No |
| Propanoic acid with Isoamyl phenylacetate (7:2) | Trace | No | No | Medium | Medium | No |
| Propanoic acid with isoamyl cinnamate | Trace | No | No | Medium | Trace | No |
| Propanoic acid with Isoamyl octanoate (7:2) | Trace | No | No | Trace | Trace | No |
| Propanoic acid with Isoamyl salicylate (7:2) | Yes | No | No | Trace | Trace | No |
| Propanoic acid with Isoamyllaurate (7:2) | Yes | No | No | Trace | Trace | No |
| Control | Yes | Yes | Yes | Yes | Yes | Yes |

Orgamsm not available
Yes = Growth
Medium = Some Growth
No = No Growth

All testing was done according to the methods in Table 4

Example 3

Corn Decontamination Tests

Corn is fermented to make ethanol. It is ground, heated to a mash and treated with enzymes prior to the addition of yeast cells to make a final preparation. Also added are one or more antibiotic preparations that tend to suppress otherwise competing microbes that would foul the fermentation process. As such antibiotics are being removed from the market place, other antimicrobial treatment processes are needful. To determine if the S-3 preparation has efficacy against corn contaminating microbes the following was done:

Approximately 5 g of ground corn (cracked corn) was treated for 1 hr with 10 ml of 0% (control), 0.25%, 0.5% and 1% solutions of S-3 made with 7:2 v/v plus 10 microliters (per 10 ml) of the nonionic surfactant sold under the trademark Triton™X-100. The treatment was for 1 hr and the product was damp dried on paper tissue to remove excess liquid. About 2 grams of material was placed directly on a PDA plate and incubated for 2 days prior to being photographed. In another case, the cracked seed was dried under a hood and then plated on PDA.

Figure 10:
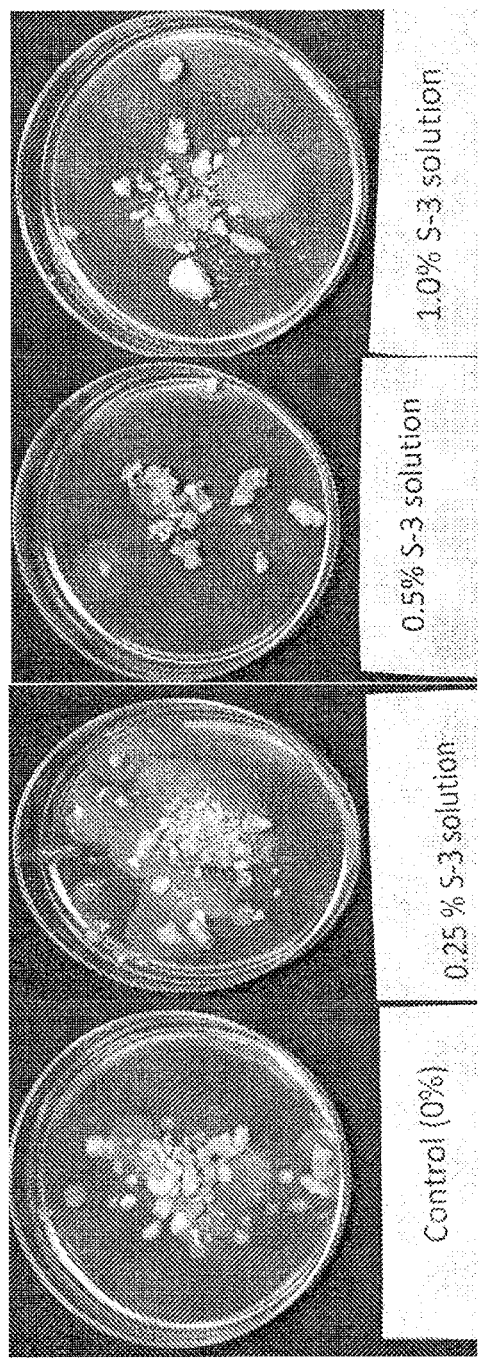
Figure 11:
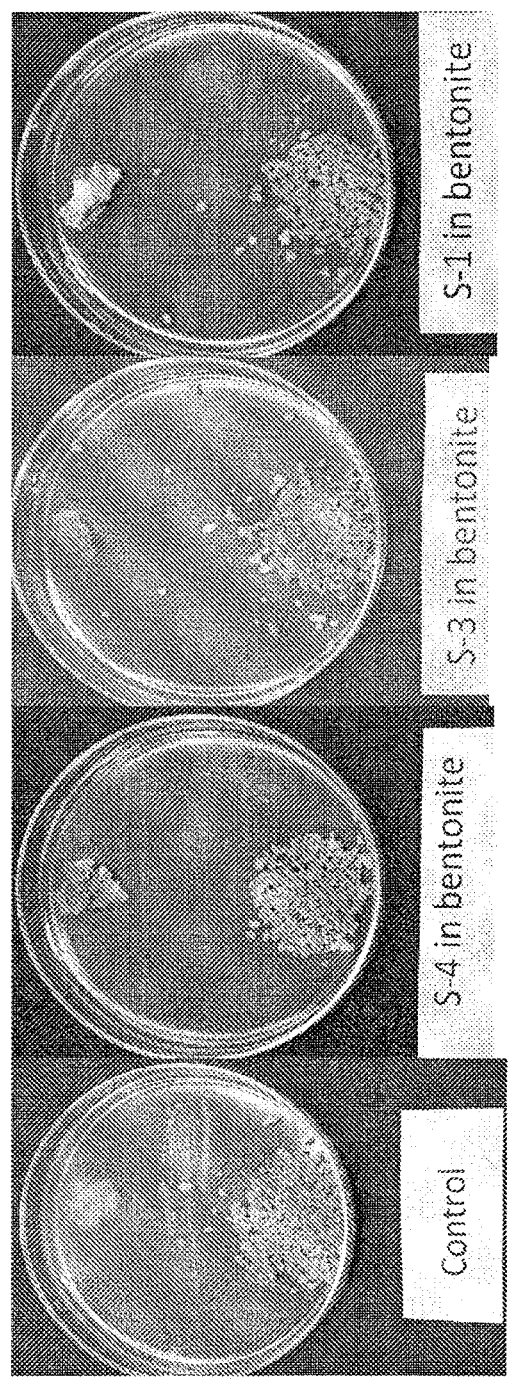

The results demonstrated that the treatment levels of 0.5% and 1.0% S-3 for 1 hr completely removed the bacterial contamination of the cracked corn particles (FIG. 10). When the corn particles were blotted dry and further dried and tested in the same manner, the results were virtually the same.

Overall, the results indicate that the S-3 solution can be used to decontaminate agriculturally and food based products and materials. This would likewise apply to instruments, equipment, clothing and food being processed for consumption.

Example 4

Use of S-4 in Treatment of Human Waste with *Fusarium subglutinans.*

Figure 12:
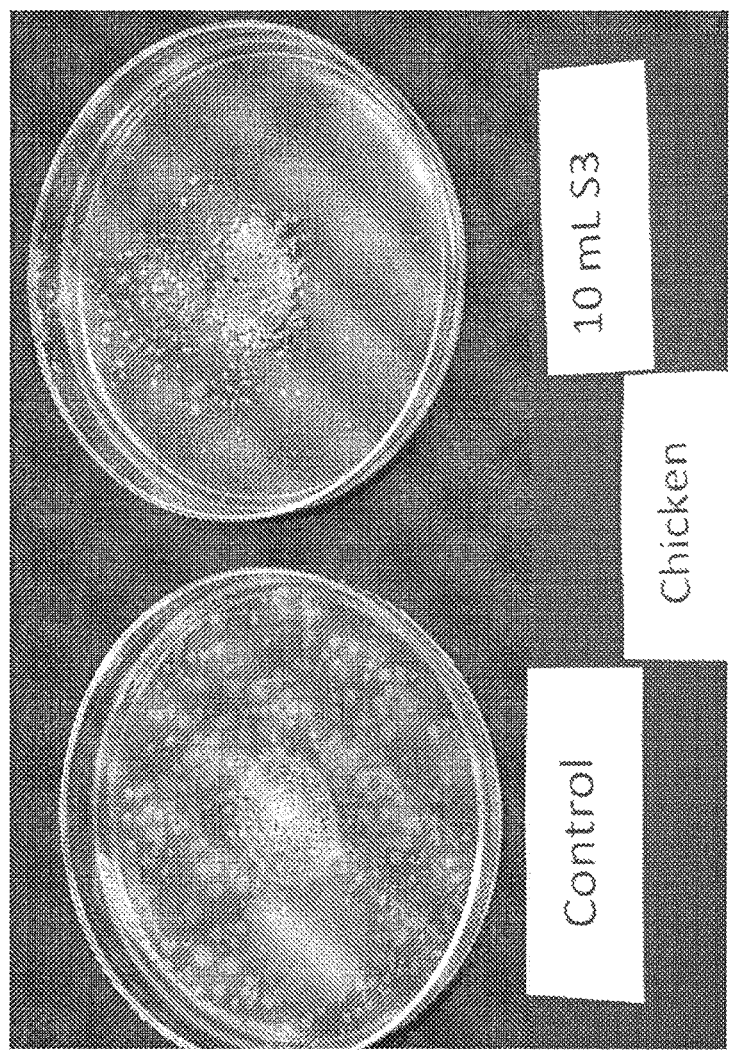

Testing of formulae S-3 and S-4 was done to learn of their efficacy in treating human waste bacteria. The testing was done using 0.5 g of bentonite having a rate of 1 ml S-1, S-2, S-3 or S-4 or B-23 per 10 g of bentonite. The control was no mixture of compounds. Barley seeds contaminated with *Fusarium subglutinans* (same one as previously used) were placed on PDA plates. The mid plate was streaked with a pure culture of *E. coli* obtained from human waste. Cap and seal with parafilm and then incubate for 3 days and photograph. The S-3 and S-4 killed the *E. coli* but there was less effect with B-23. The *fusarium* grew in the presence of S-3 and better with S-4. The *E. coli* grew in the control and slightly in the presence of B-23 all as illustrated in FIG. 11. It is to be noted that S-4 in bentonite resulted in complete killing of *E. coli* and the growth of the *Fusarium* did occur. This was also true of the S-1 and S-3 treatments but the *Fusarium* was more inhibited. The B-23 as a control was also effective in killing *E. coli* but not to the same degree. The results show that the S-4 is a good and reasonable treatment of human wastes to kill enteric bacteria with the concomitant use of *Fusarium* to allow for the breakdown of human waste materials.

Example 5

Treatment of Animal Wastes with S-3

S-3 was applied at the rate of 3 ml per lb of zeolite. To test its efficacy in treating animal wastes with control of bacterial growth the following experiments were done. The treated zeolite (0.5 g) was placed in a center well of a PDA plate (cut out). The plate had been completely streaked and covered with a suspension of bacterial cells made from chicken, goat, cat and horse manure. The plates were covered and sealed with parafilm and then observed after 3-4 days of incubation and photographed. The results in all cases showed that the S-3 was an effective antimicrobial mixture by virtue of the zone of inhibition that it caused on the plates. This effect was also noted with the case of horse, goat and cat fecal matter bacteria spread on the plates (FIG. 12). The results suggest that the S-3 zeolite combination has the potential to be used as a cat litter treatment or a treatment for chicken coops or as an animal bedding application.

Example 6

Figure 13:

The efficacy of S-3 as a cat litter treatment and as an animal bedding treatment was further tested.
Cat Litter Treatment Comparative Efficacy Testing A 1 ft.$^2$ plastic snap-seal-top container was filled with the desired litter treatment plus untreated bentonite in the proportions indicated by the packaging instructions (FIG. 13). For these tests, CLOE (used at the rate of 4 ml per lb) and an untreated bentonite control were tested. A constant temperature was maintained in the testing facility for the duration of the tests (e.g. 70° F.). About 50 g of cat feces and 5 mL urine were added to treated containers. At 24 hour intervals, the ammonia level was measured in each box using the Z-800 ammonia meter. The measurements were done by placing the meter inside each box at respective 5-minute intervals, minimizing the amount of time the container spent open. The ammonia meter yielded an average ammonia level over the five minutes, as well as a peak ammonia level achieved during the five minutes. After the measurements were complete, the day-old fecal matter was removed, and approximately 50 g of fresh fecal matter and 5 mL of urine were added. The containers were resealed. These steps were continued daily for 1 week to determine relative efficacies of the products. A one-time one-hour-interval ammonia reading was taken on each of the containers.

After 8 days, the average ammonia level readings taken over 5-minute intervals every 24 hours showed that ammonia production was much lower on the CLOE-treated litter than on the untreated control (see FIGS. 14A and 14B).

Example 7

Microbiology Analysis

Figure 15:
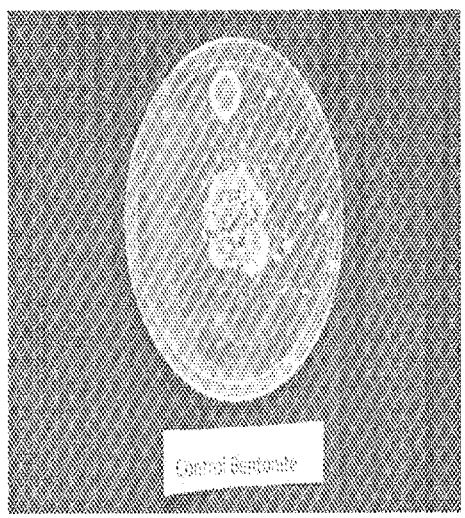
Figure 15:
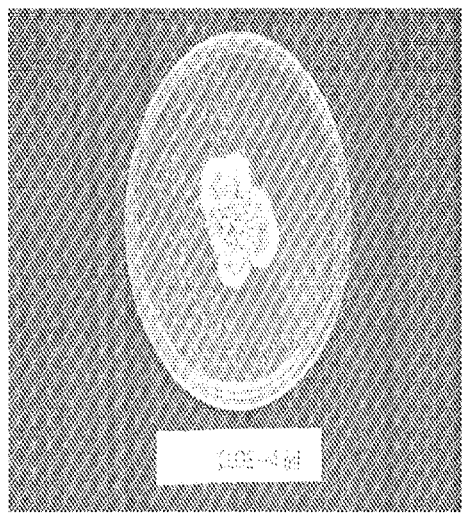

Microbiological studies were done to demonstrate that the processes of odor formation are directly related to microbiological activity in the waste and waste environment. Inhibiting or controlling microbial activity should have a beneficial effect on the reduction of odors. CLOE has a direct effect on this microbial activity, rather than ameliorating the odors by absorbing them, as other cat litter treatment products do. To demonstrate this quality, approximately 0.5 g of CLOE were placed in the center well of a potato dextrose agar (PDA) plate, which had been covered with a lawn of bacteria derived from fresh solid cat waste. The plates were incubated at 23° C. for 1 week and photographed. The series of photographs shown in FIGS. 15A and 15B indicate that the bentonite control (15A) had massive amounts of bacterial colonies growing all over the plate, including in those areas close to the well containing the litter. In contrast, the CLOE treatment (4 ml S3 per pound of carrier, 15B) was virtually free of bacterial colonies around the well of the plate, but it did sport some growth of *Penicillium* sp., which is inherent to the carrier substance and does not contribute to odor production. Please also note the *Penicillium* sp. in the control well.

Clearly, the antimicrobial activity of the CLOE product is directly related to its effectiveness as a cat litter treatment and its ability to reduce ammonia and other odors emanating from animal (specifically cat) waste, as manifested by many users. This is also confirmed by the ability of the product to inhibit and kill waste-associated microbes such as *Escherichia coli*. The CLOE formula is absorbed by the carrier substances, but it is also slowly released over time, and, as such, can effectively act at some distance from the point source of the bentonite or zeolite carrier particulate.

Example 8

Figure 16:
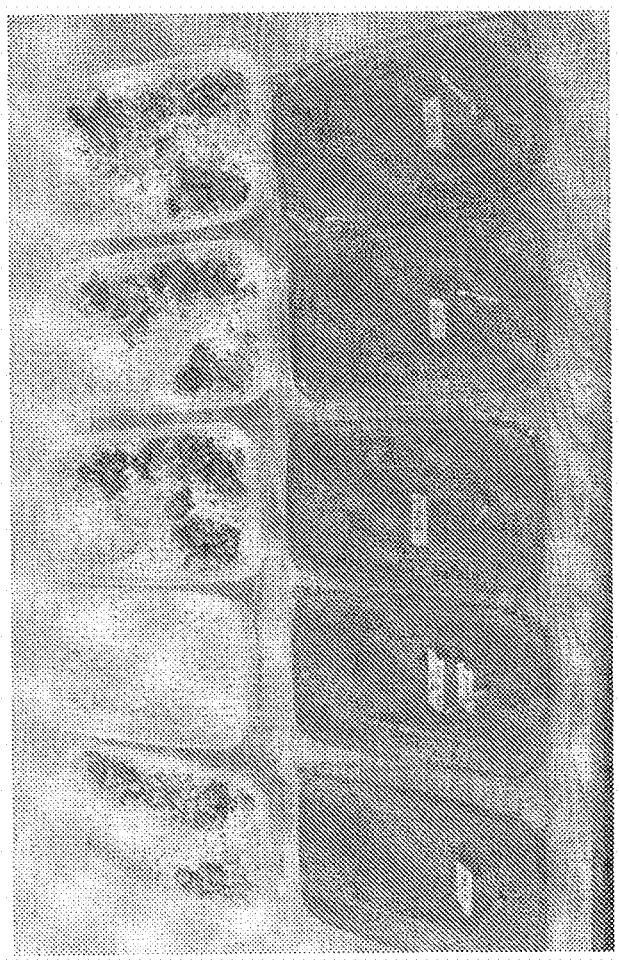

Chicken Litter Amendment Comparative Efficacy Testing 1 ft.$^2$ plastic snap-seal-top containers were filled with pine shavings and the desired bedding treatment, in the proportions indicated by the packaging instructions (FIG. 16). For these tests, Barnyard Bedding at the rate of 15 ml per lb of zeolite and an untreated zeolite control were tested, as these products are the more popular items on the market. A constant temperature was maintained in the testing facility for the duration of the tests (e.g. 70° F.). About 50 g of chicken feces were added to treated containers and sprayed with about 2 mL of water. At 24 hour intervals, the ammonia level in each box was measured using the Z-800 ammonia meter. The measurements were done by placing the ammonia meter inside each box for respective 5-minute intervals, minimizing the amount of time the container spent open. The ammonia meter yielded an average ammonia level over the five minutes, as well as a peak ammonia level achieved during the five minutes. About 50 g of fresh fecal matter and 2 mL of water were added each day after measurements were complete, and container was resealed. These steps were continued for 3 weeks to determine relative efficacy of the formula. A one-time one-hour-interval ammonia reading was taken on each of the containers.

After 8 days, the average ammonia level readings taken over 5-minute intervals every 24 hours showed that ammonia production was highest on the zeolite control and lowest on the Barnyard Bedding-treated bedding (FIGS. 17A and 17B).

Example 9

Figure 18:
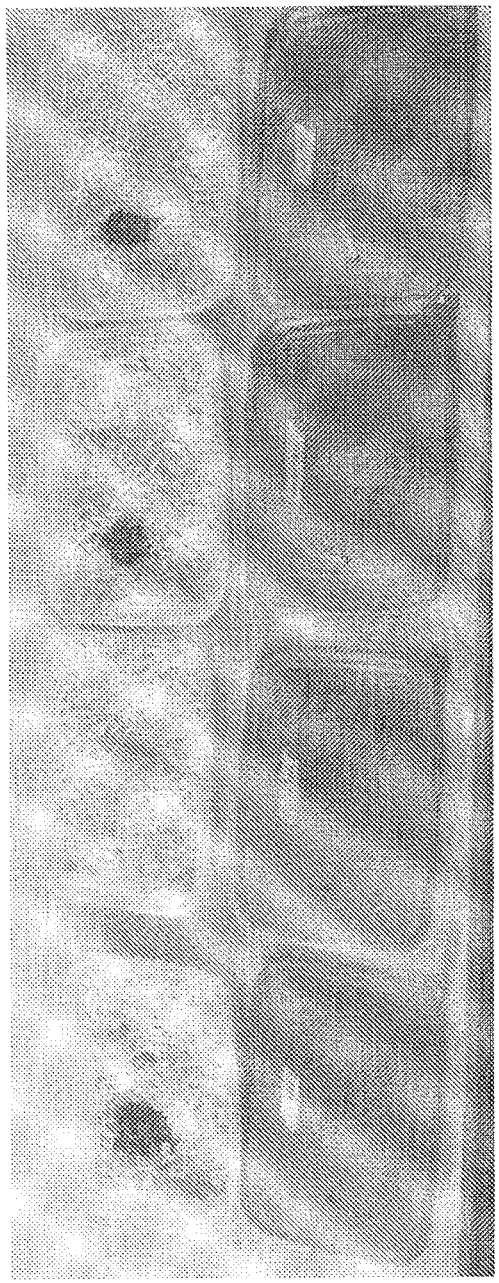
FIG. 18 depicts 1 ft.² plastic snap-seal-top container filled with pine shavings (a commonly used bedding material for large animals) and the desired bedding treatment, in the proportions indicated by the packaging instructions. For these tests, S-1 treated, and an untreated zeolite control were tested.
Figure 22:
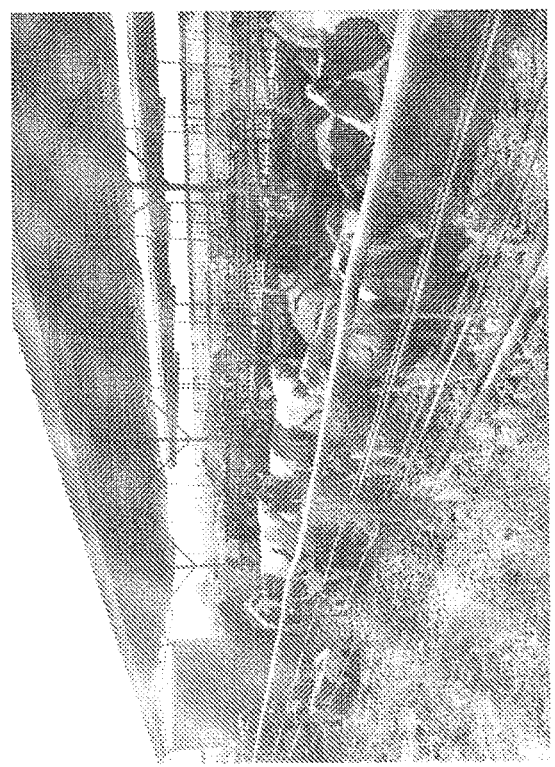
FIG. 22 is an image depicting dairy cow conditions at Dairy 1.

Large Animal Stall Litter Amendment Comparative Efficacy Testing 1 ft.$^2$ plastic snap-seal-top container was filled with pine shavings (a commonly used bedding material for large animals) and the desired bedding treatment, in the proportions indicated by the packaging instructions (FIG. 18). For these tests, Barnyard Bedding, and an untreated zeolite control were tested. A constant temperature was maintained in the testing facility for the duration of the tests (e.g. 70° F.). About 100 g of fresh horse manure and about 10 mL of urine were added to treated containers. After 24 hours, the Z-800 ammonia meter was placed inside each box to make measurements at respective 5-minute intervals, minimizing the amount of time the container was open. The ammonia meter yielded an average ammonia level over the five minutes, as well as a peak ammonia level achieved during the five minutes. After measurements were complete, the day-old manure and urine-soaked pine bedding were removed. The recommended proportion of bedding treatment for wet spots plus about 100 g fresh manure and about 10 mL of urine were added, and each container was resealed. These steps were continued for 1 week to determine relative efficacy of the products. A one-time one-hour-interval ammonia reading was taken on each of the containers.

After 8 days, the average ammonia level readings taken over 5-minute intervals every 24 hours showed that ammonia production was highest on the control bedding and lowest on the Barnyard Bedding-treated bedding (FIGS. 19A and 19B).

Example 10

Treatment of Calf Scours with Formula S-3

Calf Scours is a calf diarrheal disease caused primarily by viral and bacterial infection of the calf. In some instances, scours can occur in upwards of 70% of calves in a herd, and cause death to 50% of the infected calves. Although there is a viral etiology to these events, the most common cause is one of more pathogenic bacterial strains of *Escherichia coli*, followed by strains of *Cryposporidia* and *Salmonella*.

The minimum inhibitory concentration (MIC) of S-3 to *Escherichia coli* is <0.00125%. Also see Table 5, above. Accordingly, a solution of about 1% S-3 at 50 ml may be effective to treat a calf suffering with scours. A solution (S-X) was prepared for testing on calves diagnosed with the classical symptoms of scours.

The S-X formula contains the following ingredients:
Per 100 ml:
1 g glucose
1 g whey protein
0.25 g KCl
0.25 g MgS04
0.5 g NaCl
1 ml of S-3

Glucose and whey protein were added to provide a nutritional supplement to the treated animals, whereas the other salts were added to enhance the electrolyte balance to the animal. The S-3 component is present to inhibit and kill pathogenic bacteria.

A first test was done on 5 newly born Holstein calves not having scours in order to learn if the S-X solution was toxic or was producing any side effects. Each healthy calf was administered 50 ml of the S-X solution and after 1 day, and into several weeks later, no adverse side effects were noted, and particularly, no signs of chemical side effects or abnormal behavior.

Arrangements were then made to do in vivo animal testing with the S-X mixture at a ranch in Bozeman, Mont. Scouring animals (Angus breed) were first reported during cold damp weather several weeks prior. Each scoured animal had all of the symptoms associated with this disease. Doses for each animal were set at 50 ml per animal per treatment.

Fifteen calves authenticated as having scours were treated with 50 ml of solution via the oral cavity by tubing. Thirteen calves, having been treated with 1 dose, recovered overnight. Two animals required a second dose and recovered overnight after the second dose. FIG. 20A shows one of the two scoured calves (tag 166) that had to receive a second 50 ml treatment of the S-X solution (image taken prior to administration of S-X solution). Note the large pile of excrement in the lower right hand corner and the head and ears down and drooped (FIG. 20A). One day after the second treatment with S-X solution, the calf was ambulatory and free of diarrhea (FIG. 20B). The second day after the second S-X treatment, the calf was nursing its mother.

No deaths were reported in this experiment. The ranch owners reported that the S-X solution was far superior to all other treatments they had used to-date. Accordingly, S-X solution represents a safe, fast and effective treatment of scours.

Example 11

Livestock Scours Treatment

A scours treatment formula was developed that contained the S-3 formulation plus sugar, amino acids, sodium and potassium chloride and magnesium acetate. Many animals having infectious scours (caused by a pathogen) were treated. Typically, if the infectious scours is involved the stools are yellow to brownish to somewhat greenish. Also if a parasite is causing scours, the fecal matter contains blood and this is evident. If non-infectious scours (milk scours) is involved, the fecal matter is whitish. In this study at least two animals had milk scours and did not recover. Likewise, it appeared that one animal had parasitic scours and it too did not recover. Basically, all other animals (having viral or bacterial caused scours) did recover when given S-X treatments. In about 90% of the cases recovery was within 12-24 hr with signs of recovery occurring within 3-4 hr. In a few cases, recovery took two days requiring a second treatment. This is unlike any other treatment available. The material is delivered orally via stomach tube or syringe. Other treatments using antibiotics and nutrient electrolyte solutions do manage to assist the animal but recovery is not certain as is mostly the case with the S-3 treatment.

Exemplary Formulation and Treatment of Scours in Calves
Per 90 ml of water:
1 g of glucose
1 g glycine
0.5 g of NaCl
0.25 g KCl
0.25 g Mg acetate
1 ml of S-3 containing 0.7 ml of propanoic acid and 0.2 ml of isoamyl hexanoates.

50 ml per animal was administered via syringe or stomach tube per treatment and some re-treatment was necessary if the animal did not recover in 24 hr.

Exemplary Formulation and Treatment of Scours in Piglets
Per 90 ml of water:
1 g of glucose
1 g glycine
0.5 g of NaCl
0.25 g KCl
0.25 g Mg acetate
0.1 gKH2P04
2 ml of S-3 containing 0.7 ml of propanoic acid and 0.2 ml of isoamyl hexanoates.

1-2 ml per piglet administered via a syringe.

S-X Scours Treatment Field Study

Case 1—Ranch 1

May 16, 2014—One calf had come down with scours on the 6th of May and had been treated with Banomine and given two shots of LA-200 9 (an anti-infectious drug). Electrolyte solutions were also given on a daily basis in the dosage of 1 pint; however, the animal did not recover and languished for 9 to 10 days with chronic scours. The S-X solution was sent on the morning of May 17th and the scouring calf was administered 50 ml orally by syringe. It was noted that the calf was dramatically improved in condition by the evening and completely better on the morning of May 18th. The calf showed no further signs of scours as of May 22, 2014. These results demonstrate that virtually all scours treatments on this animal had failed and that it was not in a recovery stage until the S-3 treatment was given.

Case 2—Ranch 2

Ranch 2 experienced an influx of scouring calves and mortality in the late winter of 2014. The S-X technology solution was provided to them, and the ranchers used the solution for treatment of calves via stomach tubing. Three calves were treated in this manner. Recovery from scours for these calves occurred within 24 hours after treatment, and there were no other known medications administered at the same time as the S-X treatments that could have contributed to recovery. Sick animals were taken into the barn and photographed during their recovery. One of these animals is pictured in FIG. 21.

Case 3—Ranch 3

Ranch 3 experienced a particularly cold winter during the calving season, including high winds and a large amount of snow fall. These conditions make scouring a more common occurrence for calves.

S-X treatments for scouring calves were administered at this ranch from Apr. 2 to Apr. 24, 2014. Eleven animals were treated with 50 ml dosages using the stomach tubing method. Results were successful, with one dose in nine head; while one animal had to be treated a second time and another one needed three separate treatments. In some cases, S-X was not the only treatment given. Some of the animals also presented with symptoms of pneumonia and needed does of Baytril, sulpha pills, or Nuflor. All animals that were treated with the S-X solution recovered while most (9) recovered within twenty-four hours after treatment.

Case 4—Dairy 1

May 15, 2014—Dairy 1 is a holstein dairy cow operation. This dairy houses 300 animals whose health and everyday needs must be met. Dairy has been shown to have the rotavirus as a source for scours, which was noted by the veterinary center located near their dairy. The S-X treatment was administered to 7 young animals that had scours by oral syringe application. All of the animals that were given the S-X treatment recovered. All of the animals except one recovered within 24 hours, and one after the second treatment of S-X.

According to Dairy 1, in December of 2013, 30 of their calves were lost to scours, even though these calves had been given multiple electrolyte treatments as well as antibiotics. Treatment of these calves usually took 5-7 days with multiple treatments, as compared to the 1 day of 1-2 dosages of S-X treatments. Administration of the treatment via oral drench was preferred by Dairy 1 and proved to be effective.

The operator of Dairy 1 remarked, "Need more, since the stuff really works." She was referring to the S-X solution and their success with these treatments. The dairy will continue treating calf scours with the S-X technology as well as providing information on animals that are subsequently tested with the S-X formula.

Case 5—Ranch 4

The S-X technology was also tested at a Hutterite swine production facility the week of Apr. 14, 2014 where hundreds of piglets were exhibiting scours. The presence of the PED virus in this pig population was confirmed by Newport Labs, Worthington, Minn. According to the producer, over 850 piglets had died in the previous three weeks, which represents nearly a 100 percent fatality in infected piglets.

The producer was interviewed about the results of his trial with the piglet formula of the S-X technology for use on scouring pigs on Apr. 19, 2014. The producer noted that on or around the 12 Apr. 2014 an 8-day old piglet with scours was administered 6 ml of the S-X formula orally via syringe. After 5 hours the piglet was better and the next day there was no evidence of scours. Furthermore, on the 15th of April, 10 piglets that were all 14 days old showed evidence of scouring with the classic symptom of dark yellow loose stools. These piglets were administered 4 ml of S-X solution orally through a syringe, and within 24 hours each animal was completely "dry." The producer also indicated that from his previous experiences with the disease, he would have expected many fatalities.

Additionally, on or around April 19th 10 piglets that were 3 days old showed signs of scours and were given 2 ml of the S-X solution via syringe. All of these piglets also remained alive after several weeks. Another treatment was administered for 30 piglets that were 3 days old showing signs of scouring. These 30 piglets were given 3 ml of the S-X solution and all piglets remained alive. If the treatment had not been administered, the producer would have expected mortality for nearly all of these animals, based on his previous experiences. The producer also administered Tylan 40-50 to each of the 3 day old piglets in the study whose treatments were on April 15th and 19th. Tylan is an antibiotic that is used to treat pneumonia. The producer felt that the Tylan-40 paired with the S-X treatment was responsible for the survival of these young animals; however, according to professionals in the field, antibiotics are generally not effective against intestinal viral and bacterial infections. Although not wishing to be bound by any particular theory, in this case, Tylan-40 likely had no effect on the survival of the piglets.

Since using the S-X solution to treat his piglets, the producer has not lost any animals to scours. Additionally, as of May 27, 2014, samples from the piglets that had been sent to Norwalk labs after the addition of S-X treatments confirmed that PED was no longer present. This finding indicates that the S-X solution is successful at treating scours in pigs at the Harlowton colony. Furthermore, the disappearance of the PED virus from the area may be attributed to the S-X treatments since all piglets with scours were treated with the technology and recovered.

Case 6—Ranch 5

Ranch 5 near the Canadian border participated in S-X treatments for scours for their beef cattle ranch. The temperatures during calving season were particularly low during the past winter with driving winds and high snow falls. The S-X solution was provided early in April and the first date of treatment that followed was on Apr. 6, 2014. Twenty-one animals were treated only with the S-X solution for conditions of scouring and animals were treated by stomach tube administration of 50 ml of S-X solution. After 24 hours, 18 of the calves that had been treated with the S-X solution recovered from scouring; however, 3 animals needed a dosage re-administration. These animals soon recovered after the treatment. Of the 21 animals treated, 8 expressed symptoms of pneumonia and were given Nuflor. Recovery of animals treated with S-X was not related to the treatment for the incidence of pneumonia. The last date of treatment was on Apr. 18, 2014. In all, approximately 85 percent of the animals treated with the S-X technology recovered with one dose of the solution. These results demonstrate that S-X technology required less time and was more effective than traditional forms of treatment for scouring animals.

Case 7—Ranch 6

Ranch 6 is a dairy operation that used the S-X technology as a scours treatment in mid-April of 2014. The dairy has about 100 head of Holstein milk cattle with various other animals, including beef cattle. The incidence of scours on the ranch is particularly high and most animals acquire scours soon after birth. The S-X formula was given to the dairy and it was administered to both beef calves and Holstein calves in 50 ml doses through oral syringes.

Initial treatments of the S-X formula were given to 8 calves in 50 ml doses via syringe, 7 of which had displayed the typical creamy yellow scouring, and 1 calf (number 80) with white pasty scouring that developed into watery scours after two days. This calfs condition was typical of milk scours. This particular calf was treated with S-X well after its symptoms had developed, and it died 4 days later. It was suspected that this particular calfs scours was nutritionally caused because of the characteristics of the diarrhea, in which case the S-X technology would not have been effective. Most of the animals that were treated with the S-X solution recovered and were completely better within 24 hours; however, one holstein calf took 48 hours to fully recover. Additionally, one beef calf (number 34 as an untreated control) at the ranch was noted to have scours and was not given a dose of the S-X solution along with the other animals and it died within two weeks. FIG. 23 is a series of images showing a calf treated with S-X before and after treatment.

Case 8—Ranch 7

The owners of Ranch 7 were interested in using S-X technology in the early spring of 2014 for treating newborn calves that developed scours. The S-X solution was given to the owners and over the course of several weeks, calves that showed signs of scouring were immediately treated in the pasture with 50 ml of the S-X solution in two doses of 25 ml in an oral syringe. At least 15 calves were treated with the S-X solution and every one of them except for one recovered in 24 hr. The one calf that did not recover in 24 hours had white feces that could have been attributed to "milk scours." This calf also had pneumonia so it was also treated with Nuflor and a drench. It was also administered two additional treatments of the S-X solution. The calf did recover from scours and is now in normal condition. The owner noted that most of the time calves recovered within 3 to 4 hours after treatments of the S-X solution. The owner also commented that improvement was recognized with the calves' stoppage of "teeth grinding," and in their general increase in alertness. The owner noted that the oral syringe method of S-X solution treatment was very easy for her to administer dosages to the 100 lb calves. These results demonstrate that administration of S-X can be performed using either the stomach tube or the syringe method.

Case 9—Ranch 8

Experiments on beef calves with scours took place at Ranch 8 in at an elevation of 4,459 feet, from May 4, 2013 to May 21, 2014, concentrated in the spring of 2013 and the winter and spring of 2014. On this ranch, 300 calves are born in the spring and 300 are born in the fall. One hundred and forty two distinct calves were treated with an S-X solution or a combination of S-X solution and other medications. The initial S-X formula was used through January 2014, after which an improved formula of the S-X technology scours treatment was used. Temperatures varied from −20° F. to up to 50° F. in the months of February and March. Significant snow and winds were observed during this time period with dramatic temperature swings reported.

A large number of calves exhibited clinical signs of scours (droopy ears, sullen eyes, and profuse diarrhea). These calves were given 50 mL of the S-X solution through a stomach tube system and checked approximately six hours later to determine if they were recovering or if re-administration of the drug was needed. Of the 243 calves treated, 36 were either given only the solution for the first or second dose or the solution plus a vitamin supplement, while the rest were administered standard antibiotics along with the S-X scours treatment. Twelve of the S-X-only treatments were administered as a second or third dose within the same day. In all, 243 treatments included the S-X solution and 29 of those were treated either 2 or 3 times. Total individual calf numbers that were treated with both formulae numbered 142. Drugs that were typically given along with the S-X treatment included: Excede (treats respiratory infection), probiotics, Toxiban (absorbs toxins with charcoal), Noromycin LA (antibiotic for use on pinkeye, foot rot, and other infections), multivitamins, Inforce 3 (a three-way respiratory vaccine), Draxxin (antibiotic for pinkeye, foot rot, or respiratory disease), and sulpha tablets (sulfonamides for anti-bacterial treatments).

The owners of Ranch 8 were interviewed on Mar. 3, 2014 on their experiences with the S-X treatment for scours. Scours was first reported for the calving season on Feb. 27, 2014, and 40 doses were supplied at 50 mL each. From February 27 until March 3, 15 calves with signs of scouring had been treated with S-X technology. Thirteen of those 15 recovered overnight after one dose, while 2 required a second dose and recovered overnight with no mortality in either instance. Half of the calves were treated in the pasture with only 6 brought in to the barn. Normal treatment for scours includes electrolytes, IV administration of fluids, and some antibiotics such as tetracycline.

The producers observed that some of the calves treated had pneumonia and other medications were administered; however, it was also noted that the S-X treatments were far superior to other medications and credited its use with a quick and full recovery. It was estimated that without the S-X, one-third or more of the calves with scours would have died. Additional observations of the S-X treatment were that it was easy to use and carry when working the herd, that it was a quick treatment option and that antibiotic treatment was not required if the scours was caught quickly enough. FIG. 24 is a series of images showing a calf treated with S-X before and after treatment.

Table 7 depicts the S-X treatments administered at Ranches 3, 5, and 8 without any additional medications given besides vitamin supplements.

TABLE 7

S-X Treatments without other medications

| Ranch | S-X | Date | Calf | Treatment number |
|---|---|---|---|---|
| 8 | S-1 | May 4, 2013 | Y122 | 1st |
| 8 | S-1 | May 4, 2013 | Y306B | 1st |
| 8 | S-1 | May 6, 2013 | Y350a | 1st |
| 8 | S-3 | Feb. 24, 2014 | Y3742 | 1st |
| 8 | S-3* | Feb. 27, 2014 | Y26262 | 1st |
| 8 | S-3* | Feb. 27, 2014 | Y321 | 1st |
| 8 | S-3* | Feb. 27, 2014 | Y383 | 1st |
| 8 | S-3 | Mar. 2, 2014 | R18361 | 1st |
| 8 | S-3 | Mar. 2, 2014 | Y3730 | 1st |
| 8 | S-3 | Mar. 2, 2014 | Y387 | 1st |
| 8 | S-3 | Mar. 3, 2014 | G032 | 1st |
| 8 | S-3 | Mar. 3, 2014 | Y166461 | 1st |
| 8 | S-3 | Mar. 3, 2014 | Y402 | 1st |
| 8 | S-3 | Mar. 4, 2014 | G03 | 2nd |
| 8 | S-3 | Mar. 4, 2014 | G3731 | 1st |
| 8 | S-3 | Mar. 4, 2014 | R1396 | 1st |
| 8 | S-3 | Mar. 4, 2014 | Y29092 | 1st |
| 8 | S-3 | Mar. 5, 2014 | G309 | 1st |
| 8 | S-3 | Mar. 5, 2014 | Y29902 | 1st |
| 8 | S-3 | Mar. 5, 2014 | Y3311 | 1st |
| 8 | S-3 | Mar. 5, 2014 | Y8A20 | 1st |
| 8 | S-3 | Mar. 6, 2014 | R2451 | 2nd |

TABLE 7-continued

S-X Treatments without other medications

| Ranch | S-X | Date | Calf | Treatment number |
|---|---|---|---|---|
| 8 | S-3 | Mar. 6, 2014 | Y163391 | 1st |
| 8 | S-3 | Mar. 9, 2014 | Y2014 | 2nd |
| 8 | S-3 | Mar. 12, 2014 | R215 | 1st |
| 8 | S-3 | Mar. 15, 2014 | Y16629 | 3rd |
| 8 | S-3 | Mar. 15, 2014 | Y2014 | 2nd |
| 8 | S-3 | Mar. 16, 2014 | R26861 | 2nd |
| 8 | S-3 | Mar. 16, 2014 | Y2062 | 2nd |
| 8 | S-3 | Mar. 16, 2014 | Y3619 | 1st |
| 8 | S-3 | Mar. 17, 2014 | Y20060 | 2nd |
| 8 | S-3 | Mar. 18, 2014 | Y3630 | 2nd |
| 8 | S-3 | Mar. 18, 2014 | Y80842 | 2nd |
| 8 | S-3 | Mar. 27, 2014 | R616 | 2nd |
| 8 | S-3 | Mar. 27, 2014 | Y411 | 2nd |
| 8 | S-3 | Mar. 30, 2014 | R616 | 1st |
| S | S3 | Apr. 6, 2014 | S16 | 1st |
| S | S3 | Apr. 6, 2014 | 1122 | 1st |
| S | S3 | Apr. 6, 2014 | 12SS | 1st |
| S | S3 | Apr. 6, 2014 | 8104 | 1st |
| S | S3 | Apr. 6, 2014 | 9203 | 1st |
| S | S3 | Apr. 7, 2014 | 7490 | 1st |
| S | S3 | Apr. 8, 2014 | 173 | 1st |
| S | S3 | Apr. 8, 2014 | 1241 | 1st |
| S | S3 | Apr. 8, 2014 | S416 | 1st |
| S | S3 | Apr. 12, 2014 | 1203 | 2nd |
| S | S3 | Apr. 12, 2014 | 2487 | 1st |
| S | S3 | Apr. 12, 2014 | 2637 | 1st |
| S | S3 | Apr. 16, 2014 | 1219 | 2nd |
| S | S3 | Apr. 18, 2014 | 711 | 1st |
| S | S3 | Apr. 18, 2014 | 1000 | 1st |
| S | S3 | Apr. 18, 2014 | 1636 | 1st |
| S | S3 | Apr. 18, 2014 | k23 | 1st |
| 3 | S-X | Apr. 18, 2014 | 2431 | 1st |

*Received multivitamin supplement

Table 8 depicts all S-X treatments given regardless of whether any additional medications were administered for Ranches 3, S, and 8.

TABLE 8

All S-X treatments

| Ranch | S-X | Date | Calf | Treatment number | Additional Medication |
|---|---|---|---|---|---|
| 8 | S-1 | S/4/2013 | Y122 | 1st | |
| 8 | S-1 | S/4/2013 | Y306B | 1st | |
| 8 | S-1 | S/6/2013 | Y3S0a | 1st | |
| 8 | S-1 | S/IS/2013 | Y163 | 1st | Noromycin LA, Toxi Ban, Nas |
| 8 | S-1 | S/IS/2013 | Y169 | 1st | Noromycin LA |
| 8 | S-1 | S/IS/2013 | Y33S1 | 1st | Noromycin LA |
| 8 | S-1 | S/18/2013 | R22326 | 1st | Noromycin LA |
| 8 | S-1 | S/18/2013 | Y169 | 1st | Noromycin LA |
| 8 | S-1 | S/18/2013 | Y33S1 | 1st | Noromycin LA |
| 8 | S-1 | S/29/2013 | Y2886 | 1st | Noromycin LA, Toxi Ban |
| 8 | S-1 | Oct. 21, 2013 | Y311 | 1st | Excede Sec |
| 8 | S-1 | Oct. 23, 2013 | R287 | 1st | Noromycin LA Sec |
| 8 | S-1 | 10/2S/2013 | R32S | 1st | Noromycin LA Sec |
| 8 | S-1 | 10/2S/2013 | Y238 | 1st | Noromycin LA Sec |
| 8 | S-3 | Feb. 23, 2014 | G309 | 1st | Noromycin LA Sec, Toxi Ban, sulpha |
| 8 | S-3 | Feb. 23, 2014 | Y124981 | 1st | Noromycin LA Sec, Toxi Ban, sulpha |
| 8 | S-3 | Feb. 23, 2014 | Y14146 | 1st | Noromycin LA Sec, Toxi Ban, sulpha |
| 8 | S-3 | Feb. 23, 2014 | Y17739 | 1st | Noromycin LA Sec, Toxi Ban, sulpha |
| 8 | S-3 | Feb. 23, 2014 | Y36192 | 1st | Noromycin LA Sec, Toxi Ban, sulpha |
| 8 | S-3 | Feb. 23, 2014 | Y3742 | 1st | Noromycin LA Sec, Toxi Ban, sulpha |
| 8 | S-3 | Feb. 23, 2014 | Y40S | 1st | Noromycin LA Sec, Toxi Ban, sulpha |
| 8 | S-3 | Feb. 23, 2014 | Y420 | 1st | Noromycin LA Sec, Toxi Ban, sulpha |
| 8 | S-3 | Feb. 24, 2014 | Y3742 | 1st | |
| 8 | S-3 | Feb. 27, 2014 | Y26262 | 1st | Multivitamin |
| 8 | S-3 | Feb. 27, 2014 | Y321 | 1st | Multivitamin |
| 8 | S-3 | Feb. 27, 2014 | Y336 | 1st | Noromycin LA, multivitamin |
| 8 | S-3 | Feb. 27, 2014 | Y383 | 1st | multivitamin |
| 8 | S-3 | Feb. 27, 2014 | Y422 | 1st | |
| 8 | S-3 | Mar. 2, 2014 | R18361 | 1st | |
| 8 | S-3 | Mar. 2, 2014 | Y3730 | 1st | |
| 8 | S-3 | Mar. 2, 2014 | Y387 | 1st | |
| 8 | S-3 | Mar. 3, 2014 | G032 | 1st | |
| 8 | S-3 | Mar. 3, 2014 | Y166461 | 2nd | |
| 8 | S-3 | Mar. 3, 2014 | Y1883S2 | 1st | Noromycin LA, Toxi Ban, multivitamin |
| 8 | S-3 | Mar. 3, 2014 | Y402 | 1st | |
| 8 | S-3 | Mar. 4, 2014 | G03 | 1st | Noromycin LA, Toxi Ban, multivitamin |
| 8 | S-3 | Mar. 4, 2014 | G03 | 2nd | |
| 8 | S-3 | Mar. 4, 2014 | G3731 | 1st | |
| 8 | S-3 | Mar. 4, 2014 | R1396 | 1st | |
| 8 | S-3 | Mar. 4, 2014 | Y29092 | 1st | |
| 8 | S-3 | Mar. 4, 2014 | Y389 | 1st | Noromycin LA, Toxi Ban |
| 8 | S-3 | 3/S/2014 | G309 | 1st | |
| 8 | S-3 | 3/S/2014 | Y29902 | 1st | |
| 8 | S-3 | 3/S/2014 | Y3311 | 1st | |
| 8 | S-3 | 3/S/2014 | Y3779 | 1st | Toxi Ban |
| 8 | S-3 | 3/S/2014 | Y8A20 | 1st | |

TABLE 8-continued

All S-X treatments

| Ranch | S-X | Date | Calf | Treatment number | Additional Medication |
|---|---|---|---|---|---|
| 8 | S-3 | Mar. 6, 2014 | GOS61 | 1st | Toxi Ban |
| 8 | S-3 | Mar. 6, 2014 | G3731 | 1st | Noromycin LA, Toxi Ban |
| 8 | S-3 | Mar. 6, 2014 | R1396 | 1st | Noromycin LA, Toxi Ban |
| 8 | S-3 | Mar. 6, 2014 | R24S1 | 1st | Noromycin LA, Toxi Ban |
| 8 | S-3 | Mar. 6, 2014 | R24S1 | 2nd | |
| 8 | S-3 | Mar. 6, 2014 | R24S6 | 1st | Toxi Ban |
| 8 | S-3 | Mar. 6, 2014 | Y163391 | 1st | |
| 8 | S-3 | Mar. 6, 2014 | Y202S1 | 1st | Toxi Ban |
| 8 | S-3 | Mar. 6, 2014 | Y38S9 | 1st | Noromycin LA, Toxi Ban |
| 8 | S-3 | Mar. 6, 2014 | Y408 | 1st | Toxi Ban |
| 8 | S-3 | Mar. 7, 2014 | G03 | 1st | Noromycin LA Sec |
| 8 | S-3 | Mar. 7, 2014 | GS22 | 1st | Noromycin LA Sec |
| 8 | S-3 | Mar. 7, 2014 | R22S19 | 1st | Noromycin LA Sec |
| 8 | S-3 | Mar. 7, 2014 | Y16131 | 1st | Noromycin LA Sec |
| 8 | S-3 | Mar. 7, 2014 | Y19S1 | 1st | Noromycin LA Sec |
| 8 | S-3 | Mar. 7, 2014 | Y29961 | 1st | Noromycin LA Sec |
| 8 | S-3 | Mar. 7, 2014 | Y29962 | 1st | Noromycin LA Sec |
| 8 | S-3 | Mar. 7, 2014 | Y3779 | 1st | Noromycin LA Sec |
| 8 | S-3 | Mar. 8, 2014 | R24S1 | 1st | Noromycin LA Sec |
| 8 | S-3 | Mar. 8, 2014 | Y28869 | 1st | Noromycin LA Sec |
| 8 | S-3 | Mar. 8, 2014 | Y29962 | 1st | Excede 3cc |
| 8 | S-3 | Mar. 9, 2014 | G23S | 1st | Noromycin LA Sec |
| 8 | S-3 | Mar. 9, 2014 | R139S1 | 1st | Noromycin LA Sec |
| 8 | S-3 | Mar. 9, 2014 | Y163391 | 1st | Noromycin LA Sec |
| 8 | S-3 | Mar. 9, 2014 | Y19S4 | 1st | Excede 3cc |
| 8 | S-3 | Mar. 9, 2014 | Y2014 | 2nd | |
| 8 | S-3 | Mar. 9, 2014 | Y2014 | 1st | Noromycin LA Sec |
| 8 | S-3 | Mar. 9, 2014 | Y2220 | 1st | Noromycin LA Sec |
| 8 | S-3 | Mar. 9, 2014 | Y3016 | 1st | Noromycin LA Sec |
| 8 | S-3 | Mar. 9, 2014 | Y3042 | 1st | Noromycin LA Sec |
| 8 | S-3 | Mar. 9, 2014 | Y3S62 | 1st | Noromycin LA Sec |
| 8 | S-3 | Mar. 10, 2014 | Y166461 | 1st | Toxi Ban |
| 8 | S-3 | Mar. 10, 2014 | Y19S41 | 1st | Noromycin LA Sec |
| 8 | S-3 | Mar. 10, 2014 | Y2366 | 1st | Noromycin LA Sec |
| 8 | S-3 | Mar. 10, 2014 | Y28392 | 1st | Toxi Ban |
| 8 | S-3 | Mar. 10, 2014 | Y298S | 1st | Noromycin LA |
| 8 | S-3 | Mar. 10, 2014 | Y3630 | 1st | Noromycin LA |
| 8 | S-3 | Mar. 10, 2014 | Y36S | 1st | Noromycin LA |
| 8 | S-3 | Mar. 10, 2014 | Y401 | 1st | Noromycin LA Sec |
| 8 | S-3 | Mar. 11, 2014 | R2391 | 1st | Noromycin LA |
| 8 | S-3 | Mar. 11, 2014 | Y2014 | 1st | Noromycin LA Sec |
| 8 | S-3 | Mar. 11, 2014 | Y2162 | 1st | Excede 3cc |
| 8 | S-3 | Mar. 11, 2014 | Y298S | 1st | Noromycin LA Sec |
| 8 | S-3 | Mar. 11, 2014 | Y298S | 1st | Noromycin LA Sec |
| 8 | S-3 | Mar. 11, 2014 | Y3042 | 1st | Excede 3cc |
| 8 | S-3 | Mar. 12, 2014 | R21S | 1st | |
| 8 | S-3 | Mar. 12, 2014 | Y19349 | 1st | Noromycin LA Sec |
| 8 | S-3 | Mar. 12, 2014 | Y2116 | 1st | Excede |
| 8 | S-3 | Mar. 12, 2014 | Y2366 | 1st | Excede Sec |
| 8 | S-3 | Mar. 12, 2014 | Y298S | 1st | Excede |
| 8 | S-3 | Mar. 12, 2014 | Y29962 | 1st | Noromycin LA Sec |
| 8 | S-3 | Mar. 12, 2014 | Y3630 | 1st | Excede Sec |
| 8 | S-3 | Mar. 12, 2014 | Y646S9 | 1st | Noromycin LA Sec |
| 8 | S-3 | Mar. 13, 2014 | G3731 | 1st | Noromycin LA Sec |
| 8 | S-3 | Mar. 13, 2014 | R21S | 1st | Excede Sec, Toxi Ban |
| 8 | S-3 | Mar. 13, 2014 | Y16629 | 1st | Noromycin LA Sec |
| 8 | S-3 | Mar. 13, 2014 | Y19349 | 1st | Noromycin LA Sec |
| 8 | S-3 | Mar. 13, 2014 | Y28392 | 1st | Excede |
| 8 | S-3 | Mar. 14, 2014 | Y1l06 | 1st | Noromycin LA Sec |
| 8 | S-3 | Mar. 14, 2014 | Y16629 | 1st | Excede 3cc |
| 8 | S-3 | Mar. 14, 2014 | Y29S1 | 1st | Noromycin LA Sec |
| 8 | S-3 | 3/IS/2014 | R26861 | 1st | Noromycin LA |
| 8 | S-3 | 3/IS/2014 | R2902 | 1st | Noromycin LA Sec |
| 8 | S-3 | 3/IS/2014 | Y16629 | 3rd | |
| 8 | S-3 | 3/IS/2014 | Y2014 | 1st | Noromycin LA |
| 8 | S-3 | 3/IS/2014 | Y2014 | 2nd | |
| 8 | S-3 | 3/IS/2014 | Y2366 | 1st | EX |
| 8 | S-3 | 3/IS/2014 | Y28392 | 1st | Noromycin LA Sec |
| 8 | S-3 | 3/IS/2014 | Y298S | 1st | Draxxen |
| 8 | S-3 | 3/IS/2014 | Y3S6 | 1st | Noromycin LA |
| 8 | S-3 | 3/IS/2014 | Y3619 | 1st | Noromycin LA |
| 8 | S-3 | Mar. 16, 2014 | R21441 | 1st | Noromycin LA Sec, Toxi Ban |
| 8 | S-3 | Mar. 16, 2014 | R26861 | 2nd | |
| 8 | S-3 | Mar. 16, 2014 | Y2062 | 2nd | |
| 8 | S-3 | Mar. 16, 2014 | Y2062 | 1st | Noromycin LA Sec |

TABLE 8-continued

All S-X treatments

| Ranch | S-X | Date | Calf | Treatment number | Additional Medication |
|---|---|---|---|---|---|
| 8 | S-3 | Mar. 16, 2014 | Y2382 | 1st | Noromycin LA Sec |
| 8 | S-3 | Mar. 16, 2014 | Y264 | 1st | Noromycin LA Sec |
| 8 | S-3 | Mar. 16, 2014 | Y3619 | 1st | |
| 8 | S-3 | Mar. 17, 2014 | G23S | 1st | Noromycin LA Sec |
| 8 | S-3 | Mar. 17, 2014 | G3731 | 1st | Noromycin LA Sec |
| 8 | S-3 | Mar. 17, 2014 | R139S1 | 1st | Noromycin LA Sec |
| 8 | S-3 | Mar. 17, 2014 | R317 | 1st | Noromycin LA Sec |
| 8 | S-3 | Mar. 17, 2014 | Y20060 | 2nd | |
| 8 | S-3 | Mar. 17, 2014 | Y20060 | 1st | Noromycin LA Sec |
| 8 | S-3 | Mar. 17, 2014 | Y2116 | 1st | Noromycin LA Sec |
| 8 | S-3 | Mar. 17, 2014 | Y2382 | 2nd | Noromycin LA Sec |
| 8 | S-3 | Mar. 17, 2014 | Y264 | 1st | Noromycin LA Sec |
| 8 | S-3 | Mar. 17, 2014 | Y29S1 | 1st | Noromycin LA Sec |
| 8 | S-3 | Mar. 17, 2014 | Y3630 | 1st | Noromycin LA Sec |
| 8 | S-3 | Mar. 17, 2014 | Y80842 | 1st | Noromycin LA Sec |
| 8 | S-3 | Mar. 18, 2014 | G34491 | 1st | Noromycin LA Sec |
| 8 | S-3 | Mar. 18, 2014 | G433S | 1st | Noromycin LA Sec |
| 8 | S-3 | Mar. 18, 2014 | Y3630 | 2nd | |
| 8 | S-3 | Mar. 18, 2014 | Y646S9 | 1st | Noromycin LA Sec |
| 8 | S-3 | Mar. 18, 2014 | Y80842 | 2nd | |
| 8 | S-3 | Mar. 19, 2014 | R21S | 1st | Noromycin LA Sec |
| 8 | S-3 | Mar. 19, 2014 | R29092 | 1st | Noromycin LA Sec |
| 8 | S-3 | Mar. 19, 2014 | Y2382 | 3rd | Noromycin LA Sec |
| 8 | S-3 | Mar. 19, 2014 | Y29S1 | 1st | Noromycin LA Sec |
| 8 | S-3 | Mar. 19, 2014 | Y298S | 1st | Noromycin LA Sec |
| 8 | S-3 | Mar. 19, 2014 | Y3619 | 1st | Noromycin LA Sec |
| 8 | S-3 | Mar. 19, 2014 | Y646S9 | 2nd | Noromycin LA Sec |
| 8 | S-3 | Mar. 19, 2014 | Y80842 | 3rd | Excede 3cc |
| 8 | S-3 | Mar. 20, 2014 | Y29S1 | 1st | Noromycin LA Sec |
| 8 | S-3 | Mar. 20, 2014 | Y411 | 1st | Noromycin LA Sec |
| 8 | S-3 | Mar. 20, 2014 | Y80B42 | 1st | Excede 3cc |
| 8 | S-3 | Mar. 22, 2014 | R616 | 1st | Noromycin LA Sec |
| 8 | S-3 | Mar. 22, 2014 | Y411 | 3rd | Excede 3cc |
| 8 | S-3 | Mar. 23, 2014 | R20016 | 1st | Noromycin LA Sec |
| 8 | S-3 | Mar. 23, 2014 | R616 | 2nd | Noromycin LA Sec |
| 8 | S-3 | Mar. 23, 2014 | Y2382 | 1st | Noromycin LA Sec |
| 8 | S-3 | Mar. 23, 2014 | Y29S1 | 1st | Noromycin LA Sec |
| 8 | S-3 | Mar. 24, 2014 | R1836 | 1st | Noromycin LA Sec |
| 8 | S-3 | Mar. 24, 2014 | R29092 | 1st | Noromycin LA Sec |
| 8 | S-3 | Mar. 24, 2014 | R616 | 3rd | Noromycin LA Sec |
| 8 | S-3 | Mar. 24, 2014 | Y106S1 | 1st | Draxxen, Inforce 3 |
| 8 | S-3 | Mar. 24, 2014 | Y321 | 1st | Draxxen, Inforce 3 |
| 8 | S-3 | Mar. 24, 2014 | Y3619 | 1st | Noromycin LA Sec |
| 8 | S-3 | Mar. 24, 2014 | Y411 | 1st | Noromycin LA Sec |
| 8 | S-3 | 3/2S/2014 | R1836 | 2nd | Noromycin LA Sec |
| 8 | S-3* | 3/2S/2014 | R290 | 1st | Draxxen, sulpha |
| 8 | S-3 | 3/2S/2014 | R29092 | 1st | Noromycin LA Sec |
| 8 | S-3 | 3/2S/2014 | Y298S2 | 1st | Noromycin LA Sec |
| 8 | S-3 | 3/2S/2014 | Y3619 | 2nd | Noromycin LA Sec |
| 8 | S-3* | 3/2S/2014 | Y368 | 1st | Draxxen, sulpha |
| 8 | S-3* | 3/2S/2014 | Y3742 | 1st | Draxxen, sulpha |
| 8 | S-3* | 3/2S/2014 | Y3862 | 1st | Draxxen, sulpha |
| 8 | S-3* | Mar. 26, 2014 | G1310 | 1st | Draxxen, sulpha |
| 8 | S-3* | Mar. 26, 2014 | R239 | 1st | Draxxen, sulpha |
| 8 | S-3* | Mar. 26, 2014 | R239 | 2nd | Draxxen, sulpha |
| 8 | S-3* | Mar. 26, 2014 | R3000 | 1st | Draxxen, sulpha |
| 8 | S-3* | Mar. 26, 2014 | R3041 | 1st | Draxxen, sulpha |
| 8 | S-3* | Mar. 26, 2014 | Y1606 | 1st | Draxxen, sulpha |
| 8 | S-3* | Mar. 26, 2014 | Y20142 | 1st | Draxxen, sulpha |
| 8 | S-3 | Mar. 26, 2014 | Y2S9 | 1st | Noromycin LA Sec |
| 8 | S-3* | Mar. 26, 2014 | Y28869 | 1st | Draxxen, sulpha |
| 8 | S-3* | Mar. 26, 2014 | Y29062 | 1st | Draxxen, sulpha |
| 8 | S-3* | Mar. 26, 2014 | Y30162 | 2nd | Draxxen, sulpha |
| 8 | S-3* | Mar. 26, 2014 | Y30162 | 1st | Draxxen, sulpha |
| 8 | S-3* | Mar. 26, 2014 | Y331 | 1st | Draxxen, sulpha |
| 8 | S-3 | Mar. 26, 2014 | Y3619 | 3rd | Noromycin LA Sec |
| 8 | S-3 | Mar. 27, 2014 | R1836 | 1st | Noromycin LA Sec |
| 8 | S-3 | Mar. 27, 2014 | R616 | 1st | Noromycin LA Sec |
| 8 | S-3 | Mar. 27, 2014 | R616 | 2nd | |
| 8 | S-3 | Mar. 27, 2014 | R8461 | 1st | Draxxen, sulpha |
| 8 | S-3 | Mar. 27, 2014 | Y411 | 1st | Noromycin LA Sec |
| 8 | S-3 | Mar. 27, 2014 | Y411 | 1st | |
| 8 | S-3* | Mar. 28, 2014 | Y1361 | 1st | Draxxen, sulpha |
| 8 | S-3* | Mar. 28, 2014 | Y1606 | 1st | Draxxen, sulpha |
| 8 | S-3 | Mar. 28, 2014 | Y266962 | 1st | Noromycin LA Sec |

TABLE 8-continued

All S-X treatments

| Ranch | S-X | Date | Calf | Treatment number | Additional Medication |
|---|---|---|---|---|---|
| 8 | S-3* | Mar. 29, 2014 | G1310 | 1st | Draxxen, sulpha |
| 8 | S-3* | Mar. 29, 2014 | R2028 | 1st | Draxxen, sulpha |
| 8 | S-3* | Mar. 29, 2014 | Y16932 | 1st | Draxxen, sulpha |
| 8 | S-3* | Mar. 29, 2014 | Y1883S | 1st | Draxxen, sulpha |
| 8 | S-3* | Mar. 29, 2014 | Y3S90 | 1st | Draxxen, sulpha |
| 8 | S-3* | Mar. 30, 2014 | G3060 | 1st | Draxxen, sulpha |
| 8 | S-3 | Mar. 30, 2014 | R616 | 1st | |
| 8 | S-3* | Mar. 30, 2014 | Y166461 | 1st | Draxxen, sulpha |
| 8 | S-3* | Mar. 30, 2014 | Y2116 | 1st | Draxxen, sulpha |
| 8 | S-3 | Mar. 30, 2014 | Y2S9 | 1st | Noromycin LA Sec |
| 8 | S-3* | Mar. 31, 2014 | G131 | 1st | Draxxen, sulpha |
| 8 | S-3* | Mar. 31, 2014 | GSOS2 | 1st | Draxxen, sulpha |
| 8 | S-3 | Mar. 31, 2014 | GS7 | 1st | Noromycin LA Sec |
| 8 | S-3 | Mar. 31, 2014 | R3691 | 1st | Noromycin LA Sec |
| 8 | S-3 | Mar. 31, 2014 | Y1124 | 1st | Noromycin LA Sec |
| 8 | S-3* | Mar. 31, 2014 | Yll9 | 1st | Draxxen, sulpha |
| 8 | S-3 | Mar. 31, 2014 | Y26682 | 1st | Noromycin LA Sec |
| 8 | S-3* | Mar. 31, 2014 | Y2839 | 1st | Draxxen, sulpha |
| 8 | S-3* | Mar. 31, 2014 | Y36192 | 1st | Draxxen, sulpha |
| 8 | S-3* | Mar. 31, 2014 | Y36S | 1st | Draxxen, sulpha |
| 8 | S-3* | Mar. 31, 2014 | Y384 | 1st | Draxxen, sulpha |
| 8 | S-3 | Mar. 31, 2014 | Y386 | 1st | Noromycin LA Sec |
| 8 | S-3 | Mar. 31, 2014 | Y424 | 1st | Noromycin LA Sec |
| 8 | S-3* | Apr. 1, 2014 | B139S | 1st | Draxxen, sulpha |
| 8 | S-3* | Apr. 1, 2014 | GSOS2 | 2nd | Draxxen, sulpha |
| 8 | S-3 | Apr. 1, 2014 | Y1126 | 2nd | Noromycin LA Sec |
| 8 | S-3 | Apr. 1, 2014 | Y2446 | 1st | Noromycin LA Sec |
| 8 | S-3 | Apr. 1, 2014 | Y266962 | 2nd | Noromycin LA Sec |
| 8 | S-3 | Apr. 1, 2014 | Y298S2 | 1st | Noromycin LA Sec |
| 8 | S-3* | Apr. 1, 2014 | Y3279 | 1st | Draxxen, sulpha |
| 8 | S-3* | Apr. 1, 2014 | Y3412 | 1st | Draxxen, sulpha |
| 8 | S-3* | Apr. 1, 2014 | Y43 | 1st | Draxxen, sulpha |
| 8 | S-3* | Apr. 1, 2014 | YS92 | 1st | Draxxen, sulpha |
| 8 | S-3* | Apr. 2, 2014 | Y17739 | 1st | Draxxen |
| 8 | S-3* | Apr. 2, 2014 | Y26262 | 1st | Draxxen, sulpha |
| 8 | S-3 | Apr. 2, 2014 | Y298S2 | 2nd | Noromycin LA Sec |
| 8 | S-3* | Apr. 2, 2014 | Y399 | 1st | Draxxen, sulpha |
| 8 | S-3* | Apr. 3, 2014 | Y121242 | 1st | Draxxen |
| 8 | S-3* | Apr. 3, 2014 | Y16936 | 1st | Draxxen |
| 8 | S-3* | Apr. 3, 2014 | Y411 | 1st | Draxxen |
| 8 | S-3 | S/21/2014 | G34491 | 1st | Noromycin LA Sec |
| 8 | S-3 | S/21/2014 | R1836 | 1st | Noromycin LA Sec |
| 8 | S-3 | S/21/2014 | R20016 | 1st | Noromycin LA Sec |
| 8 | S-3 | S/21/2014 | R2616 | 1st | Noromycin LA Sec |
| 8 | S-3 | S/21/2014 | R29092 | 1st | Excede 3cc |
| 8 | S-3 | S/21/2014 | Y411 | 2nd | Noromycin LA Sec |
| 8 | S-3 | S/21/2014 | YS861 | 1st | Noromycin LA Sec |
| S | S3 | Apr. 6, 2014 | 8104 | 1st | |
| S | S3 | Apr. 6, 2014 | 9203 | 1st | |
| S | S3 | Apr. 6, 2014 | 1122 | 1st | |
| S | S3 | Apr. 6, 2014 | S16 | 1st | |
| S | S3 | Apr. 6, 2014 | 12SS | 1st | |
| S | S3 | Apr. 7, 2014 | 12SS | 2nd | Nuflor |
| S | S3 | Apr. 7, 2014 | 7490 | 1st | |
| S | S3 | Apr. 8, 2014 | 1203 | 1st | Nuflor |
| S | S3 | Apr. 8, 2014 | 1241 | 1st | |
| S | S3 | Apr. 8, 2014 | S416 | 1st | |
| S | S3 | Apr. 8, 2014 | 173 | 1st | |
| S | S3 | Apr. 12, 2014 | 2363 | 1st | Nuflor |
| S | S3 | Apr. 12, 2014 | 9203 | 1st | Nuflor |
| S | S3 | Apr. 12, 2014 | 1203 | 2nd | |
| S | S3 | Apr. 12, 2014 | 2637 | 1st | |
| S | S3 | Apr. 12, 2014 | 2487 | 1st | |
| S | S3 | Apr. 12, 2014 | 2763 | 1st | Nuflor |
| S | S3 | Apr. 14, 2014 | 1219 | 1st | Nuflor |
| S | S3 | Apr. 16, 2014 | 1219 | 2nd | |
| S | S3 | Apr. 18, 2014 | 1000 | 1st | |
| S | S3 | Apr. 18, 2014 | 1636 | 1st | |
| S | S3 | Apr. 18, 2014 | k23 | 1st | |
| S | S3 | Apr. 18, 2014 | 711 | 1st | |
| 3 | S-X | Apr. 8, 2014 | 2012 | 1st | Drench |
| 3 | S-X | Apr. 18, 2014 | Y273 | 1st | Drench, Baytril |
| 3 | S-X | Apr. 18, 2014 | 2431 | 1st | |
| 3 | S-X | Apr. 18, 2014 | Y177 | 1st | Baytril |
| 3 | S-X | Apr. 22, 2014 | Y82 | 1st | Drench, Baytril |

TABLE 8-continued

All S-X treatments

| Ranch | S-X | Date | Calf | Treatment number | Additional Medication |
|---|---|---|---|---|---|
| 3 | S-X | Apr. 23, 2014 | Y273 | 1st | Suprio |
| 3 | S-X | Apr. 24, 2014 | 2811 | 1st | Drench, Nuflor |
| 3 | S-X | Apr. 24, 2014 | wi | 1st | Drench, Nuflor, sulpha |
| 3 | S-X | Apr. 24, 2014 | 1100 | 1st | Baytril |
| 3 | S-X | Apr. 25, 2014 | 841 | 1st | Drench |
| 3 | S-X | Apr. 25, 2014 | longhorn | 1st | Drench |
| 3 | S-X | Apr. 25, 2014 | 452 | 1st | Drench, Nuflor |

*indicates S-X treatment through nasal passages (2cc)

Example 12

Animal Mastitis Treatment

The problem of mastitis in the mammary glands in animals is typically caused by infections brought about by *Escherichia coli* or *Staphyloccous aureus* and other bacterial pathogens. The teat becomes inflamed and eventually the condition can spread to all other sectors of the mammary gland. Milk production ceases. If untreated, the animal can die. Most antibiotic treatments are expensive and ineffective. In the past three months, a yew lamb and two dairy cows suffering with mastitis were treated with 15 mL per teat of the mastitis treatment solution. FIG. 25A depicts a teat of a sheep suffering from mastitis. The treated animal was well developed in terms of the disease and it did not die but remains healthy. The mammary gland has ceased functioning. The S-3 formula was administered via syringe (FIG. 25B). Two cows suffering with mastitis were in the earlier stages of this disease. Each was treated with 15 ml per infected teat and total recovery was noted within 24 hr.

Exemplary formulation and treatment for mastitis of farm animals

Per 90 ml of water:
  5 mg of a surfactant carrier sold under the trademark CREMOPHOR® or other appropriate surfactant 0.7 ml of propanoic acid and 0.2 ml of isoamyl hexanoates The formulation was shaken well and administered to a cow up to 15 ml per teat with a syringe. The surfactant carrier acts to bring the ingredients of the S-3 formulation into solution.

Example 13

MIC Testing of S-3 and S-4 Formulations
MIC Protocol for Testing S-3 and S-4

Turbid bacterial cultures grown in the appropriate nutrient broth medium were adjusted to $OD_{6so}=0.4$ and subsequently diluted 1:100 in broth, representing a concentration of $1\times10^6$ CFU/ml. 50 lll of this culture were added to each well except the negative control, in which 50 lll broth was added. The final amount of bacteria in each well was $5\times10^6$ CFU.

20 lll stock B-23 antibiotic solution was added to 480 lll broth. 250 lll of this solution was diluted 1:2. This was repeated twice to form four progressively diluted antibiotic solutions. Dilutions are such that final concentrations of the antibiotic in the appropriate wells were equal to 1%, 0.5%, 0.25%, and 0.125% of the stock B-23 antibiotic solution.

A 96-well microtiter plate was used. 6 total treatments were plated: 1%, 0.5%, 0.25%, 0.125%, 0.061%, 0.03% and 0% antibiotic with bacterial inoculum; and no bacterial inoculum. Each treatment was plated in triplicate.

Broth was added to each well to reach a final volume of 200 lll. In wells without bacterial inoculum or antibiotic solution, an additional 50 lll broth was added.

MIC plates were incubated at appropriate growth conditions to the time points recorded on result tables. End points were chosen when the positive control well was turbid.

The MIC point was taken as the lowest concentration at which no growth was evident.

Results

The MICs were as follows for the following organisms:
*Bacillus subtilis:* 0.06125% *Vibrio*
*cholerae:* 0.06125% *Pseudomonas*
*aeruginosa:* 0.125%
*Salmonella enterica* serovar *Typhimurium:* 0.06125%
*Escherichia coli:* 0.125%
Methicillin-resistant *Staphylococcus aureus:* 0.06125%

For other MIC tests—Potato dextrose broth was used instead of nutrient broth and the tests were done in the same manner. The results were:
*Erwinia amylovora:* 0.0612%
*Lactobacillus* sp.: 0.0625%
*Erwinia carotovora:* 0.125%

The results demonstrate that the S-3 and S-4 are useful for the treatment of diseases in plants, animals and humans caused by microorganisms. These diseases include plant diseases caused by *Erwinia* and the problem in grain fermentation to produce ethanol caused by *Lactobacillus* spp. biofilms produced by *Pseudomonas*. Additional diseases include food ailments caused by *Salmonella, E. coli* and general major diseases caused by MRSA.

Example 14

Raspberry Treatments

Figures 26, 26A, 26B:
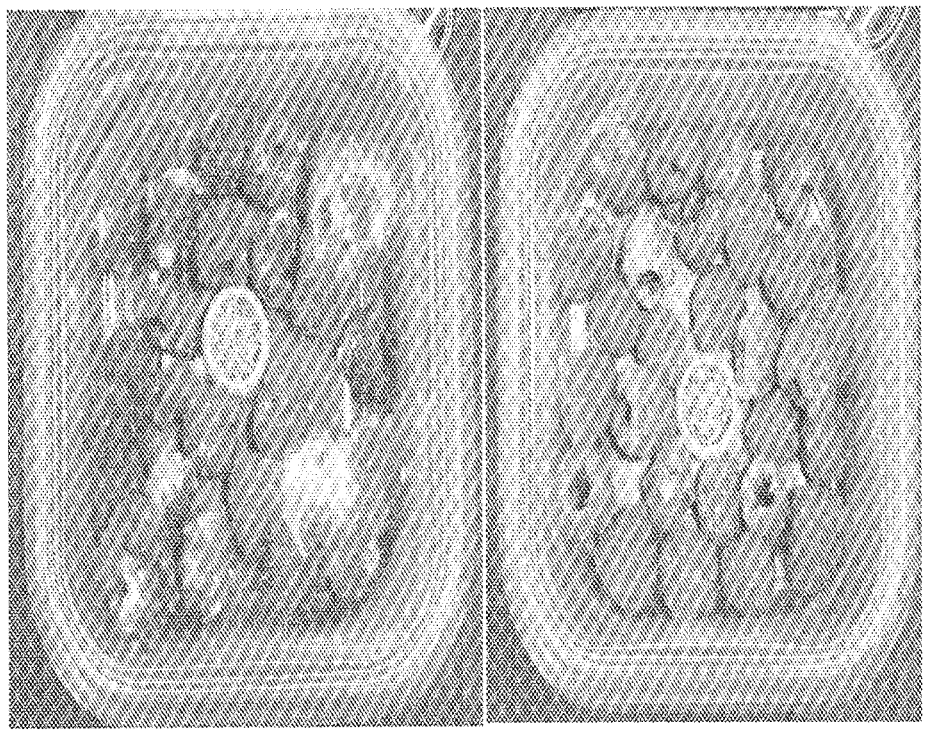
FIG. 26, comprising
FIGS. 26A-26B, depicts images of raspberries before and after treatment.
Figures 28, 28A, 28B, 28C, 28D:
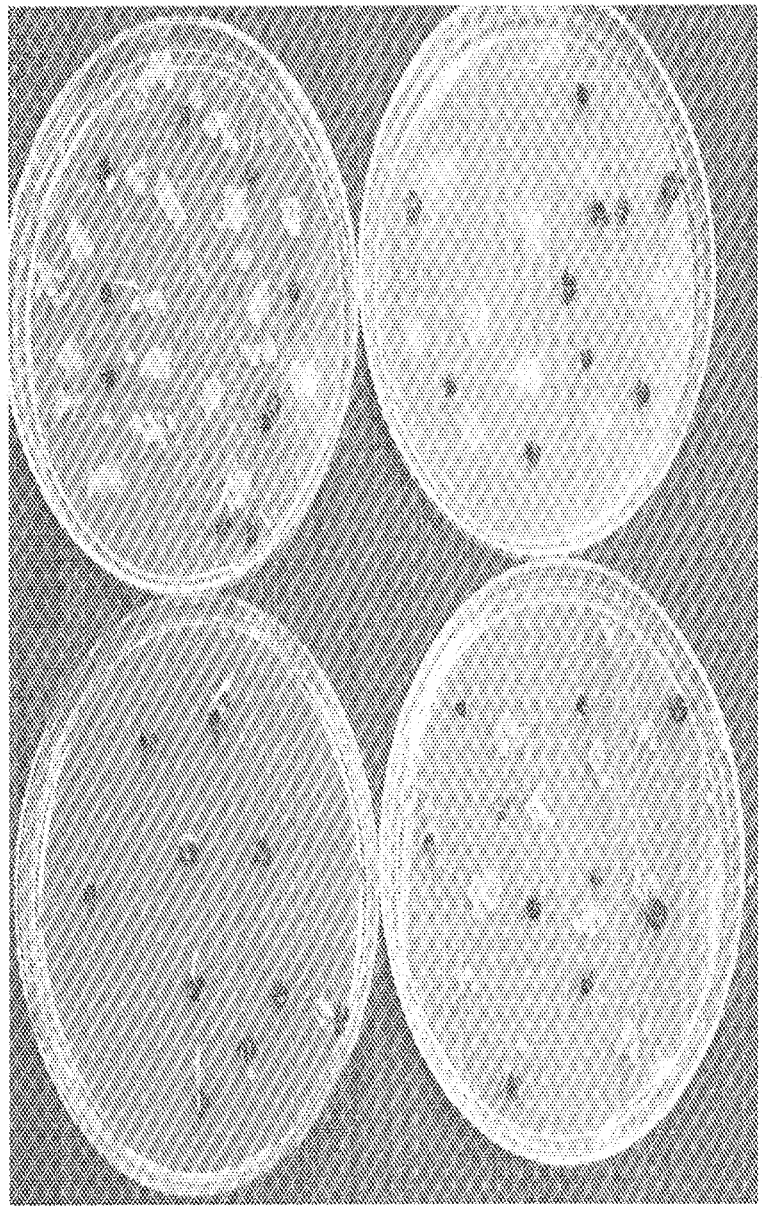
FIG. 28, comprising
FIGS. 28A-28D, depicts images of water agar plates for testing of S-3 with red beet seed.

The results described herein demonstrate that the S-X technology is useful for the preservation of fruit and vegetables during shipment and storage. The S-3 formula was mixed to form two formulations: 1 ml of S-3 per 10 g of bentonite (the 1:10 mixture); 1 ml of S-3 to 20 g bentonite (the 1:20 mixture) or other carrier. 1 gram of the mixture was placed in a small plastic cup in the presence of store purchased raspberries. The materials were placed in a small clear plastic box, which was sealed and held at room temperature for 1 week, followed by examination for the presence of contaminating fungi. The results demonstrate that the normal flora of the fruit quickly brings about its decay after 1 week at room temperature (FIG. 26A). However, use of the 1:10 mixture resulted in no decay (FIG. 26B). However, the 1:20 mixture did not perform quite as well as the 1:10 mixture, as at least 1 berry showed decay. Nonetheless, the 1:20 mixture was useful for preventing decay in the berries, and the treated berries were edible. A similar experiment was conducted with store purchased Thompson delicious grapes and the results were similar, wherein the control grapes were observed to show decay, while the treated grapes were not decayed. The grapes were also edible, as 4 people ate them and provided an evaluation of their acceptability.

Example 15

Treatment of Food Poisoning and/or Stomach Flu in Humans Using S-X

The symptoms and conditions of food poisoning and/or stomach flu in humans re similar to those occurring in animals suffering with scours. For example, possible symptoms include: abdominal cramps, diarrhea (may be bloody), fever and chills, headache, nausea, vomiting, and weakness (may be serious). Most people simply suffer through the experience (12-48 hr) by doing their best to rest, and drink replacement fluids and minerals being lost through diarrhea and vomiting. It appears that no product is available that provides instant relief However, in ten volunteers suffering with one or more of these symptoms, at least 10-15 ml of a 1% S-3 formula was taken orally at the onset of symptoms or within a few hours of the appearance of symptoms. In all cases, the patients described feeling better within one to two hours after treatment. Fever, stomach pain, diarrhea and vomiting all ceased, and the patients fully recovered. All patients were adults, white and represented both male and female classes. One patient, however reported that there was no difference noted in the stomach condition after taking a 10 ml dose of a 1% S-3 formula. Although not wishing to be bound by any particular theory, it is suspected that the patient was experiencing a viral induced stomach infection that would not have responded to S-X treatment. Nevertheless, the fact that 90% of the people treated having such an immediate and complete recovery, combined with all of the animal studies on scouring, supports the hypothesis that the S-3 is useful for treating humans suffering from stomach flu and stomach poisoning caused by bacteria. This hypothesis is further supported by the impressive MIC values of S-3 against $E$ $coli$ and $S. aureus$, which are two known causal agents of food poisoning in people (Example 13).

Example 16

Mastitis in Dairy Cattle and the S-X Technology
Treatment:

A formula containing 2% of the S-3 formulation in the presence of 5 mg of a non-ionic solubilizer sold under the trademark CREMOPHOR® in pure water is thoroughly mixed and is used as the treatment agent. Eight dairy cattle suffering with preclinical to sub-clinical mastitis were treated with 12 ml of the formula per teat. In seven cases the treatment was repeated during the course of one day. In all cases the animals were fully recovered the following day. Although not wishing to be bound by any particular theory, the recovery of the animals is likely due to the fact that the common bacterial causes of mastitis, such as $E. coli$ and $S. aureus$, are organisms that are extremely sensitive to the S-X formulations described herein (see Example 13.)

Example 17

S-3 Detergent Testing

Several detergents that were obtained through sample orders were tested with the S-3 solution for effectiveness on surfaces that are notoriously ridden with a variety of pathogens. These surfaces included a laboratory floor, and the women's bathroom floor, toilet bowl, and door handle. For the floor testing, about 5 ml of each of the detergent solutions (with 1 ml of S-3 per 100 ml of deionized water) was poured on different sections of the floor and wiped dry with a paper towel. When this section of the floor was dried then it was wiped with a Kimwipe and this was then wiped across the surface of a potato dextrose broth petri plate. For the toilet bowl testing, a paper towel was wet with the detergent solutions and a section of the surface was wiped. Kimwipes were used again once the surface dried and further streaked across a potato dextrose broth plate. The procedure for the door handle was the same as that for the sink except only one of the detergents was tested along with a control. The results are depicted in Tables 9 and 10 below.

TABLE 9

Laboratory floor results

| | Amount of detergent | Experiment 1 Number of Colonies | Experiment 2 Number of Colonies |
|---|---|---|---|
| Control | | 22 | 23 |
| Sucragel CF | 1 milliliter | 1 | 0 |
| Chemoxide CAW | 2 milliliter | 1 | 2 |
| BioSoft D40 | 0.5 milliliter | 0 | 3 |
| Lathanol LAL | 1 gram | 2 | 1 |
| BioTerge AS-40 | 1 milliliter | 1 | 2 |
| Nacconol 90G | 1 gram | 1 | 4 |
| Potassium cocoate | 2 milliliter | 1 | 1 |

Table 9 shows the number of bacterial or fungal columns that grew on potato dextrose broth plates that were streaked from samples wiped with the various detergents or with just the Kimwipe as a control after 48 hours. One milliliter of S-3 was used per 100 milliliters of deionized water.

TABLE 10

Detergent Testing in Women's Bathroom

| | Amount of detergent | Floor Colonies | Toilet Bowl Colonies | Door Handle Colonies |
|---|---|---|---|---|
| Control | | 12 | 6 | 2 |
| Sucragel CF | 1 milliliter | 1 | 0 | 0 |
| Chemoxide CAW | 2 milliliter | 0 | 1 | |
| BioSoft D40 | 0.5 milliliter | 0 | 0 | |
| Lathanol LAL | 1 gram | 2 | 16 | |
| BioTerge AS-40 | 1 milliliter | 4 | 21 | |
| Potassium cocoate | 1 gram | 0 | 4 | |
| Nacconol 90G | 2 milliliter | 1 | 0 | |

Table 10 shows the results from women's bathroom testing on a variety of surfaces (floor, toilet bowl, and door handle), and the number of bacterial or fungal colonies swiped from the surfaces with a Kimwipe that grew after 48 hours on a potato dextrose broth plate.

Example 17

$Verticillium$ Experiment

Thirty pea seeds were inoculated with $Verticillium$ sp. after being placed on a petri dish growing the fungus. The seeds were rolled around liberally and then samples of the fungus were scraped up and placed with the pea seeds in a petri dish that was sealed with parafilm and left for three days. After the three days had passed, potato dextrose agar plates with sterilized caps placed in their centers were either filled with 50 microliters of S-3, 20 microliters of S-3, or left empty as a control. Ten pea seeds from the inoculated group were placed in each of the three petri dishes containing potato dextrose agar, and filled or unfilled caps. The peas were left for two days and then checked for fungal growth and germination. The results of the experiment are depicted in Table 11.

TABLE 11

Verticillium Inoculated Pea seeds

| Treatment | Percent with Fungal Growth |
|---|---|
| Control | 100 |
| 20 microliters S-3 | 0 |
| 50 microliters S-3 | 0 |

The percent of pea seeds inoculated with *Verticillium* sp. that germinated and showed fungal growth after 48 hours in the control (no S-3), with 20 microliters S-3, and with 50 microliters S-3.

Example 17

Camelina Experiment

Camelina seeds known to be contaminated with various fungal and bacterial pathogens were taken and placed with S3 to see if fungal and bacterial growth could be halted. Several potato dextrose broth plates were obtained along with caps for S-3 placement. About forty seeds were placed on one of the plates and an empty, sterilized cap was placed in the center as the control group. This plate was parafilmed and left for two days to determine germination and fungal and bacterial growth. Over one hundred seeds were placed on another petri dish with a sterilized cap filled with 50 microliters of S-3. These seeds were left to sit with the S-3 in a tightly parafilmed dish for the following hourly intervals, at which point twenty to thirty seeds were taken out and plated individually on a dish: 1 hours, 2 hours, 4 hours, 8 hours, 16 hours, 24 hours, and 48 hours. For each of the intervals, the plates were left for 48 hours and then checked for germination and pathogen growth.

TABLE 12

*Camelina* Seeds Germination and Pathogen Growth

| | Seeds Per Plate | Percent Germinated | Percent with Pathogen Growth |
|---|---|---|---|
| Control | 39 | 100 | 56 |
| 50 microliters S-3: | | | |
| 1 Hour | 29 | 97 | 45 |
| 2 Hour | 25 | 96 | 40 |
| 4 Hour | 22 | 100 | 9 |

Table 12 shows the number of infected camelina seeds' percent germination and percent with pathogen growth that were either plated with no S-3 (control), or plated with 50 microliters of S-3 at hourly intervals. All samples were recorded 48 hours after being put on potato dextrose broth plates.

The disclosures of each and every U.S. patent and published U.S. patent application cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. An antibacterial component having antibacterial activity, and consisting of an antibacterially effective amount of
    a combination of isoamyl hexanoates and an acid selected from the group consisting of propanoic acid, isobutyric acid, and combinations thereof,
    wherein the volume ratio of the acid to the isoamyl hexanoates in the combination is about 7:2.

2. A human or animal food composition comprising the antibacterial component of claim 1.

3. A human or animal nutritional supplement comprising the antibacterial component of claim 1.

4. A human food or animal feed supplement comprising the antibacterial component of claim 1.

5. A human or animal health supplement comprising the antibacterial component of claim 1.

6. An antibacterial human or animal waste treatment composition comprising the antimicrobial component of claim 1.

7. A formulation comprising the antibacterial component of claim 1, wherein the antibacterial effect of the component is present in the formulation regardless of whether any additional antimicrobial agent or other ingredient is included in the formulation.

8. A cleaning composition for reducing microbial growth on surfaces or instruments, or in areas, consisting of the formulation of claim 7.

9. The cleaning composition of claim 8, where the surfaces, instruments, or areas are located in one or more locations selected from the following: a medical facility; an agricultural plant; and a livestock facility.

10. The cleaning composition of claim 8, suitable for use as a solution or spray for treating surfaces, instruments, or areas in one or more of the following: hospitals; home or restaurant or grocery food preparation areas; industrial food processing centers; and other locations where food is processed, stored, transported, or sold, and in which bacterial contamination may be a problem.

11. A cleaning composition for degrading, or deodorizing human or animal waste, comprising the component of claim 1.

12. A cleaning composition for treatment of waste in one or more locations selected from the following: a latrine, cat litter box, animal stall, barn, chicken-raising facility, pig barn, pet station in a home, and zoo, comprising the antibacterial component of claim 1.

13. A cleaning composition for treatment of waste in one or more locations selected from the following: a latrine, cat litter box, animal stall, barn, chicken-raising facility, pig barn, pet station in a home, and zoo, consisting of the formulation of claim 7.

14. A pharmaceutical composition for treating a human or animal having a bacterial infection, comprising the antibacterial component of claim 1.

15. A pharmaceutical composition for treating a human or animal having a microbial infection, consisting of the formulation of claim 7.

16. A method of treating a human or animal having a bacterial infection, comprising the steps of
    identifying a human or animal in need of such treatment, and administering to that human or animal an oral or topical formulation comprising an effective amount of the antibacterial component of claim 1.

17. A method of treating a human or animal having a bacterial infection, comprising the steps of
    identifying a human or animal in need of such treatment, and administering to that human or animal an effective amount of the formulation of claim 7 in the form of an oral or topical preparation.

18. The method of claim 16, wherein the bacterial infection is caused by *Escherichia coli, Staphylococcus aureus*, or *Salmonella*.

19. The method of claim 17, wherein the bacterial infection is caused by *Escherichia coli, Staphylococcus aureus*, or *Salmonella*.

20. The method of claim 17, wherein the at least one acid in the combination is propanoic acid and isobutyric acid combined at a ratio of about 1:1 by volume.

* * * * *

SEQUENCE LISTING

<160> NUMBER OF SEQ ID NOS: 10

<210> SEQ ID NO 1
<211> LENGTH: 480
<212> TYPE: DNA
<213> ORGANISM: Fusarium subglutinans

<400> SEQUENCE: 1
aacataccaa ttgttgcctc ggcggatcag cccgctcccg gtaaaacggg acggcccgcc 60
agaggacccc taaactctgt ttctatatgt aacttctgag taaaaccata aataaatcaa 120
aactttcaac aacggatctc ttggttctgg catcgatgaa gaacgcagca aaatgcgata 180
agtaatgtga attgcagaat tcagtgaatc atcgaatctt tgaacgcaca ttgcgcccgc 240
cagtattctg gcgggcatgc ctgttcgagc gtcatttcaa ccctcaagcc cagcttggtg 300
ttgggactcg cgagtcaaat cgcgttcccc aaattgattg gcggtcacgt cgagcttcca 360
tagcgtagta gtaaaaccct cgttactggt aatcgtcgcg gccacgccgt taaaccccaa 420
cttctgaatg ttgacctcgg atcaggtagg aatacccgct gaacttaagc atatcaataa 480

<210> SEQ ID NO 2
<211> LENGTH: 478
<212> TYPE: DNA
<213> ORGANISM: Fusarium subglutinans

```
<400> SEQUENCE: 2
cataccaatt gttgcctcgg cggatcagcc cgctcccggt aaaacgggac ggcccgccag      60
aggaccccta aactctgttt ctatatgtaa cttctgagta aaaccataaa taaatcaaaa     120
ctttcaacaa cggatctctt ggttctggca tcgatgaaga acgcagcaaa atgcgataag     180
taatgtgaat tgcagaattc agtgaatcat cgaatctttg aacgcacatt gcgcccgcca     240
gtattctggc gggcatgcct gttcgagcgt catttcaacc ctcaagccca gcttggtgtt     300
gggactcgcg agtcaaatcg cgttccccaa attgattggc ggtcacgtcg agcttccata     360
gcgtagtagt aaaaccctcg ttactggtaa tcgtcgcggc cacgccgtta acccccaact     420
tctgaatgtt gacctcggat caggtaggaa tacccgctga acttaagcat atcaataa      478

<210> SEQ ID NO 3
<211> LENGTH: 488
<212> TYPE: DNA
<213> ORGANISM: Fusarium sp

<400> SEQUENCE: 3
cttaatgttg cctcggcgga tcagcccgcg ccccgtaaaa cgggacggcc cgccagagga      60
cccaaactct aatgtttctt attgtaactt ctgagtaaaa caaacaaata aatcaaaact     120
ttcaacaacg gatctcttgg ttctggcatc gatgaagaac gcagcaaaat gcgataagta     180
atgtgaattg cagaattcag tgaatcatcg aatctttgaa cgcacattgc gcccgctggt     240
attccggcgg gcatgcctgt tcgagcgtca tttcaaccct caagccccgg gtttggtgt      300 tggggatcgg ctctgccttc tggcggtgcc gcccccgaaa tacattggcg gtctcgctgc     360
agcctccatt gcgtagtagc taacaccctcg caactggaac gcggcgcggc catgccgtaa     420
aaccccaact tctgaatgtt gacctcggat caggtaggaa tacccgctga acttaagcat     480
atcaatag                                                              488

<210> SEQ ID NO 4
<211> LENGTH: 477
<212> TYPE: DNA
<213> ORGANISM: Fusarium culmorum

<400> SEQUENCE: 4
cataccttat gttgcctcgg cggatcagcc cgcgccccgt aaaagggac ggcccgccgc       60 aggaccccta aactctgttt ttagtggaac ttctgagtat aaaaaacaaa taaatcaaaa     120
ctttcaacaa cggatctctt ggttctggca tcgatgaaga acgcagcaaa atgcgataag     180
taatgtgaat tgcagaattc agtgaatcat cgaatctttg aacgcacatt gcgcccgcca     240
gtattctggc gggcatgcct gttcgagcgt catttcaacc ctcaagccca gcttggtgtt     300
gggagctgca gtcctgctgc actccccaaa tacattggcg gtcacgtcga gcttccatag     360
cgtagtaatt tacatatcgt tactggtaat cgtcgcggcc acgccgttaa ccccaacttt     420
ctgaatgttg acctcggatc aggtaggaat acccgctgaa cttaagcata tcaatag        477

<210> SEQ ID NO 5
<211> LENGTH: 485
<212> TYPE: DNA
<213> ORGANISM: Fusarium avenaceum

<400> SEQUENCE: 5
cagaagttgg ggttttacgg catggccgcg ccgcgttcca gttgcgaggt gttagctact      60
acgcaatgga ggctgcagcg agaccgccaa tgtatttcgg gggcggcacc gccagaaggc     120
```

```
agagccgatc cccaacacca aacccggggg cttgagggtt gaaatgacgc tcgaacaggc    180
atgcccgccg aataccagc gggcgcaatg tgcgttcaaa gattcgatga ttcactgaat     240
tctgcaattc acattactta tcgcattttg ctgcgttctt catcgatgcc agaaccaaga    300
gatccgttgt tgaaagtttt gatttatttg tttgttttac tcagaagtta caataagaaa    360
cattagagtt tgggtcctct ggcgggccgt cccgttttac ggggcgcggg ctgatccgcc     420
gaggcaacat taaggtatgt tcacaggggt ttgggagttg taaactcggt aatgatccct    480
ccgca                                                                485
```

<210> SEQ ID NO 6
<211> LENGTH: 469
<212> TYPE: DNA
<213> ORGANISM: Fusarium subglutinans

<400> SEQUENCE: 6

```
cagaagttgg ggtttaacgg cgtggccgcg acgattacca gtaacgaggg ttttactact     60
acgctatgga agctcgacgt gaccgccaat caatttgggg aacgcgattt gactcgcgag    120
tcccaacacc aagctgggct tgagggttga atgacgctc gaacaggcat gcccgccaga     180
atactggcgg gcgcaatgtg cgttcaaaga ttcgatgatt cactgaattc tgcaattcac    240
attacttatc gcattttgct gcgttcttca tcgatgccag aaccaagaga tccgttgttg    300
aaagttttga tttatttatg gttttactca gaagttacat atagaaacag agtttagggg    360
tcctctggcg ggccgtcccg ttttaccggg agcgggctga tccgccgagg caacaattgg     420
tatgttcaca ggggtttggg agttgtaaac tcggtaatga tccctccgc                 469
```

<210> SEQ ID NO 7
<211> LENGTH: 480
<212> TYPE: DNA
<213> ORGANISM: Fusarium avenaceum

<400> SEQUENCE: 7

```
gaagttgggg ttttacggca tggccgcgcc gcgttccagt tgcgaggtgt tagctactac     60
gcaatggagg ctgcagcgag accgccaatg tatttcgggg cggcaccgc cagaaggcag    120 agccgatccc caacaccaaa cccgggggct tgagggttga atgacgctc gaacaggcat    180 gcccgccgga ataccagcgg gcgcaatgtg cgttcaaaga ttcgatgatt cactgaattc    240
tgcaattcac attacttatc gcattttgct gcgttcttca tcgatgccag aaccaagaga    300
tccgttgttg aaagttttga tttatttgtt tgttttactc agaagttaca ataagaaaca    360
ttagagtttg gtcctctgg cgggccgtcc cgttttacgg ggcgcgggct gatccgccga     420
ggcaacatta aggtatgttc acaggggttt gggagttgta aactcggtaa tgatccctcc    480
```

<210> SEQ ID NO 8
<211> LENGTH: 468
<212> TYPE: DNA
<213> ORGANISM: Fusarium subglutinans

<400> SEQUENCE: 8

```
gaagttgggg tttaacggcg tggccgcgac gattaccagt aacgagggtt ttactactac     60
gctatggaag ctcgacgtga ccgccaatca atttggggaa cgcgatttga ctcgcgagtc    120
ccaacaccaa gctgggcttg agggttgaaa tgacgctcga acaggcatgc ccgccagaat    180
actggcgggc gcaatgtgcg ttcaaagatt cgatgattca ctgaattctg caattcacat    240
```

```
tacttatcgc attttgctgc gttcttcatc gatgccagaa ccaagagatc cgttgttgaa    300
agttttgatt tatttatggt tttactcaga agttacatat agaaacagag tttaggggtc    360
ctctggcggg ccgtcccgtt ttaccgggag cgggctgatc cgccgaggca acaattggta    420
tgttcacagg ggtttgggag ttgtaaactc ggtaatgatc cctccgca                 468

<210> SEQ ID NO 9
<211> LENGTH: 19
<212> TYPE: DNA
<213> ORGANISM: Artificial sequence
<220> FEATURE:
<223> OTHER INFORMATION: Chemically synthesized

<400> SEQUENCE: 9
tccgtaggtg aacctgcgg                                                 19

<210> SEQ ID NO 10
<211> LENGTH: 20
<212> TYPE: DNA
<213> ORGANISM: Artificial sequence
<220> FEATURE:
<223> OTHER INFORMATION: Chemically synthesized

<400> SEQUENCE: 10
tcctccgctt attgatatgc                                                20
```